US012178908B2

(12) United States Patent
Jhaveri et al.

(10) Patent No.: US 12,178,908 B2
(45) Date of Patent: Dec. 31, 2024

(54) TOLEROGENIC LIPOSOMES AND METHODS OF USE THEREOF

(71) Applicant: AnTolRx, Inc., Cambridge, MA (US)

(72) Inventors: Aditi Jhaveri, Boston, MA (US); Vincent P. Stanton, Jr., Belmont, MA (US)

(73) Assignee: AnTolRx, Inc., Cambridge, MA (US)

( * ) Notice: Subject to any disclaimer, the term of this patent is extended or adjusted under 35 U.S.C. 154(b) by 0 days.

(21) Appl. No.: 16/975,789

(22) PCT Filed: Feb. 26, 2019

(86) PCT No.: PCT/US2019/019609
§ 371 (c)(1),
(2) Date: Aug. 26, 2020

(87) PCT Pub. No.: WO2019/165436
PCT Pub. Date: Aug. 29, 2019

(65) Prior Publication Data
US 2020/0405642 A1    Dec. 31, 2020

Related U.S. Application Data

(60) Provisional application No. 62/755,946, filed on Nov. 5, 2018, provisional application No. 62/635,376, filed on Feb. 26, 2018.

(51) Int. Cl.
*A61K 9/127*        (2006.01)
*A61K 9/107*        (2006.01)
*A61K 31/713*       (2006.01)

(52) U.S. Cl.
CPC .......... *A61K 9/1272* (2013.01); *A61K 9/1075* (2013.01); *A61K 31/713* (2013.01)

(58) Field of Classification Search
CPC .......... A61K 9/1272; A61K 9/51; A61K 9/14; A61K 9/127
See application file for complete search history.

(56) References Cited

U.S. PATENT DOCUMENTS

| 5,801,030 A | 9/1998 | McVey et al. |
| 5,804,413 A | 9/1998 | DeLuca |
| 5,837,511 A | 11/1998 | Falck-Pedersen et al. |
| 5,837,532 A | 11/1998 | Preston et al. |

(Continued)

FOREIGN PATENT DOCUMENTS

| WO | WO-91/02788 A1 | 3/1991 |
| WO | WO-96/04394 A1 | 2/1996 |

(Continued)

OTHER PUBLICATIONS

Silvia Rodriguez-Fernandez et al. "Phosphatidylserine-liposomes Promote Tolerogenic Features on Dendritic cells in human Type 1 Diabetes by apoptotic Mimicry." Frontiers in Immunology, vol. 9, Article 253, Feb. 14, 2018, pp. 1-17. (Year: 2018).*

(Continued)

*Primary Examiner* — Isaac Shomer
(74) *Attorney, Agent, or Firm* — Clark & Elbing LLP

(57) ABSTRACT

The invention provides compositions (e.g., liposomes) for treating diseases and conditions associated with pathologic immune responses and methods for formulating and administering such compositions.

9 Claims, 27 Drawing Sheets

Specification includes a Sequence Listing.

(56) References Cited

U.S. PATENT DOCUMENTS

| | | | |
|---|---|---|---|
| 5,846,782 A | 12/1998 | Wickham et al. | |
| 5,849,561 A | 12/1998 | Falck-Pedersen | |
| 5,849,572 A | 12/1998 | Glorioso et al. | |
| 7,186,699 B2 | 3/2007 | Harding et al. | |
| 7,465,583 B2 | 12/2008 | Samulski et al. | |
| 7,790,449 B2 | 9/2010 | Gao et al. | |
| 7,803,622 B2 | 9/2010 | Engelhardt et al. | |
| 8,338,157 B2 | 12/2012 | Jantz et al. | |
| 8,409,842 B2 | 4/2013 | Clark et al. | |
| 8,445,251 B2 | 5/2013 | Smith et al. | |
| 8,569,253 B2 | 10/2013 | Ando et al. | |
| 8,637,255 B2 | 1/2014 | Wilson et al. | |
| 8,679,837 B2 | 3/2014 | Zolotukhin et al. | |
| 8,697,853 B2 | 4/2014 | Voytas et al. | |
| 8,802,437 B2 | 8/2014 | Tremblay et al. | |
| 8,846,578 B2 | 9/2014 | McCray et al. | |
| 8,921,112 B2 | 12/2014 | Cai et al. | |
| 8,956,828 B2 | 2/2015 | Bonini et al. | |
| 9,005,973 B2 | 4/2015 | Cost et al. | |
| 9,028,978 B2 | 5/2015 | Kim et al. | |
| 2004/0029106 A1 | 2/2004 | Samulski et al. | |
| 2006/0177819 A1 | 8/2006 | Smith et al. | |
| 2007/0036757 A1 | 2/2007 | Kleinschmidt et al. | |
| 2007/0110724 A1 | 5/2007 | Samulski et al. | |
| 2007/0142622 A1* | 6/2007 | Peakman | C07K 14/47 530/324 |
| 2008/0254008 A1 | 10/2008 | Dropulic et al. | |
| 2009/0017543 A1 | 1/2009 | Wilkes et al. | |
| 2009/0088398 A1 | 4/2009 | Gregory et al. | |
| 2009/0118212 A1 | 5/2009 | Davidson et al. | |
| 2009/0148936 A1 | 6/2009 | Stout et al. | |
| 2009/0175897 A1 | 7/2009 | Tang et al. | |
| 2009/0305344 A1 | 12/2009 | Polo et al. | |
| 2010/0008889 A1 | 1/2010 | Mayall | |
| 2010/0216804 A1* | 8/2010 | Zale | A61K 47/60 977/773 |
| 2011/0033935 A1 | 2/2011 | Jantz et al. | |
| 2011/0044902 A1 | 2/2011 | Weiner et al. | |
| 2011/0113509 A1 | 5/2011 | Jantz et al. | |
| 2011/0262457 A1 | 10/2011 | Weiner et al. | |
| 2012/0009161 A1 | 1/2012 | Leboulch et al. | |
| 2012/0100606 A1 | 4/2012 | Zolotukhin et al. | |
| 2012/0276109 A1 | 11/2012 | Fraser et al. | |
| 2012/0283318 A1 | 11/2012 | Mei et al. | |
| 2013/0096182 A1 | 4/2013 | Chatterjee et al. | |
| 2013/0224863 A1 | 8/2013 | Jantz et al. | |
| 2013/0336993 A1 | 12/2013 | Weiner et al. | |
| 2014/0037585 A1 | 2/2014 | Wright et al. | |
| 2014/0087426 A1 | 3/2014 | Liu et al. | |
| 2014/0155469 A1 | 6/2014 | Bahou et al. | |
| 2014/0248305 A1 | 9/2014 | Ertl et al. | |
| 2014/0248306 A1 | 9/2014 | Charneau et al. | |
| 2014/0335607 A1 | 11/2014 | Trono et al. | |
| 2014/0357523 A1 | 12/2014 | Zeiner et al. | |
| 2015/0050243 A1 | 2/2015 | Kaczmarczyk et al. | |
| 2015/0065562 A1 | 3/2015 | Yazicioglu et al. | |
| 2015/0071898 A1 | 3/2015 | Liu et al. | |
| 2015/0071899 A1 | 3/2015 | Liu et al. | |
| 2015/0079064 A1 | 3/2015 | Gersbach et al. | |
| 2015/0079155 A1 | 3/2015 | Jensen et al. | |
| 2015/0093831 A1 | 4/2015 | Brennan et al. | |
| 2015/0118216 A1 | 4/2015 | Liu et al. | |
| 2015/0165054 A1 | 6/2015 | Liu et al. | |
| 2015/0166969 A1 | 6/2015 | Takeuchi et al. | |
| 2015/0166980 A1 | 6/2015 | Liu et al. | |
| 2015/0202231 A1 | 7/2015 | Weiner et al. | |
| 2015/0203870 A1 | 7/2015 | Trono et al. | |
| 2015/0224209 A1 | 8/2015 | Kohn et al. | |
| 2016/0024183 A1 | 1/2016 | Shoenfeld et al. | |
| 2016/0058792 A1 | 3/2016 | Quintana et al. | |
| 2016/0060358 A1* | 3/2016 | Hay | C07K 14/62 530/387.2 |
| 2016/0313324 A1 | 10/2016 | Quintana et al. | |
| 2016/0338955 A1* | 11/2016 | Bredehorst | A61K 9/06 |
| 2017/0121683 A1 | 5/2017 | Kaufman et al. | |
| 2017/0348415 A1* | 12/2017 | Hoge | C07K 16/2875 |
| 2018/0256617 A1 | 9/2018 | Ryazanov et al. | |

FOREIGN PATENT DOCUMENTS

| | | | |
|---|---|---|---|
| WO | WO-97/12986 A2 | 4/1997 | |
| WO | WO-98/15637 A1 | 4/1998 | |
| WO | WO-98/53087 A1 | 11/1998 | |
| WO | WO-99/06583 A1 | 2/1999 | |
| WO | WO-2007/017556 A1 | 2/2007 | |
| WO | WO-2007/123976 A2 | 11/2007 | |
| WO | WO-2008/090360 A1 | 7/2008 | |
| WO | WO-2015/089443 A2 | 6/2015 | |
| WO | WO-2016/077654 A1 | 5/2016 | |
| WO | WO-2016154362 A1 * | 9/2016 | ........... A61K 31/135 |
| WO | WO-2019/099977 A2 | 5/2019 | |
| WO | WO-2019/165436 A1 | 8/2019 | |
| WO | WO-2020/106695 A1 | 5/2020 | |

OTHER PUBLICATIONS

Irma Pujol-Autonell et al. "Use of Autoantigen-Loaded Phosphatidylserine-Liposomes to Arrest Autoimmunity in Type 1 Diabetes." PLOS ONE, DOI:10.1371, Jun. 3, 2015, pp. 1-19. (Year: 2015).*
Extended European Search Report for European Application No. 19758300.8, dated Nov. 12, 2021 (17 pages).
Laouini et al., "Preparation, characterization and applications of liposomes: State of the art," Journal of Colloid Science and Biotechnology 1:147-68 (2012) (23 pages).
Mulero-Navarro et al., "New Trends in Aryl Hydrocarbon Receptor Biology," Front Cell Dev Biol. 4:45 (2016) (14 pages).
Chylinski et al., "The tracrRNA and Cas9 families of type II CRISPR-Cas immunity systems," RNA Biology. 10(5):726-37 (2013).
Cong et al., "Multiplex Genome Engineering Using CRISPR/Cas Systems," available in PMC Oct. 11, 2013, published in final edited form as: Science. 339(6121):819-23 (2013) (9 pages).
Deltcheva et al., "CRISPR RNA maturation by trans-encoded small RNA and host factor RNase III," available in PMC Sep. 30, 2011, published in final edited form as: Nature. 471(7340):602-7 (2011) (54 pages).
DiCarlo et al., "Genome engineering in Saccharomyces cerevisiae using CRISPR-Cas systems," Nucleic Acids Research. 41(7):4336-4343 (2013).
Ferretti et al., "Complete genome sequence of an M1 strain of Streptococcus pyogenes," Proc Natl Acad Sci U.S.A. 98(8):4658-63 (2001).
Ghafary et al., "Novel cinnamic acid-tryptamine hybrids as potent butyrylcholinesterase inhibitors: Synthesis, biological evaluation, and docking study," Arch Pharm (Weinheim). 351(10):e1800115 (2018) (10 pages).
Hwang et al., "Efficient genome editing in zebrafish using a CRISPR-Cas system," available in PMC Sep. 1, 2013 as "Efficient In Vivo Genome Editing Using RNA-Guided Nucleases," published in final edited form as: Nat Biotechnol. 31(3):227-9 (2013) (12 pages).
International Search Report and Written Opinion for International Application No. PCT/US20/42385, mailed Dec. 21, 2020 (10 pages).
Jiang et al., "RNA-guided editing of bacterial genomes using CRISPR-Cas systems," available in PMC Sep. 1, 2013 as "CRISPR-assisted editing of bacterial genomes," published in final edited form as: Nat Biotechnol. 31(3):233-9 (2013) (23 pages).
Jinek et al., "A programmable dual RNA-guided DNA endonuclease in adaptive bacterial immunity," HHMI, published in final edited form as: Science. 337(6096):816-821 (2012) (14 pages).
Jinek et al., "RNA-programmed genome editing in human cells," ELife. 2:e00471 (2013) (9 pages).
Mali et al., "RNA-Guided Human Genome Engineering via Cas9," available in PMC Aug. 15, 2013, published in final edited form as: Science. 339(6121):823-6 (2013) (8 pages).
International Preliminary Report on Patentability for International Patent Application No. PCT/US2019/019609, mailed Sep. 3, 2020 (9 pages).

(56) References Cited

OTHER PUBLICATIONS

International Search Report and Written Opinion for International Application No. PCT/US19/19609, mailed May 6, 2019 (17 pages).
Pujol-Autonell et al., "Liposome-based immunotherapy against autoimmune diseases: therapeutic effect on multiple sclerosis," Nanomedicine (Lond). 12(11):1231-1242 (2017).
Shiizaki et al., "Identification of amino acid residues in the ligand-binding domain of the aryl hydrocarbon receptor causing the species-specific response to omeprazole: possible determinants for binding putative endogenous ligands," Mol Pharmacol. 85(2):279-89 (2014).
Tseng et al., "Liposomes incorporated with cholesterol for drug release triggered by magnetic field," Journal of Medical and Biological Engineering 27(1):29-34 (2007).
Yang et al., "Long-term dietary supplementation with saury oil attenuates metabolic abnormalities in mice fed a high-fat diet: combined beneficial effect of omega-3 fatty acids and long-chain monounsaturated fatty acids," Lipids Health Dis. 14:155 (2015).
Yeste et al., "Tolerogenic nanoparticles inhibit T cell-mediated autoimmunity through SOCS2," Sci Signal. 9(433):ra61 (2016).
Extended European Search Report for European Application No. 20840843.5, dated Jun. 23, 2023 (10 pages).
Li et al., "Role of esterase mediated hydrolysis of simvastatin in human and rat blood and its impact on pharmacokinetic profiles of simvastatin and its active metabolite in rat," J Pharm Biomed Anal. 168:13-22 (May 10, 2019).
Ratnatilaka Na Bhuket et al., "Simultaneous determination of curcumin diethyl disuccinate and its active metabolite curcumin in rat plasma by LC-MS/MS: Application of esterase inhibitors in the stabilization of an ester-containing prodrug," J Chromatogr B Analyt Technol Biomed Life Sci. 1033-1034:301-310 (Oct. 15, 2016).
Yeste et al., "Nanoparticle-mediated codelivery of myelin antigen and a tolerogenic small molecule suppresses experimental autoimmune encephalomyelitis," Proc Natl Acad Sci U.S.A. 109(28):11270-5 (Jul. 10, 2012).
Yuan et al., "Use of a carboxylesterase inhibitor of phenylmethanesulfonyl fluoride to stabilize epothilone D in rat plasma for a validated UHPLC-MS/MS assay," J Chromatogr B Analyt Technol Biomed Life Sci. 969:60-8 (Oct. 15, 2014).
Zeng et al., "Simultaneous determination of a selective adenosine 2A agonist, BMS-068645, and its acid metabolite in human plasma by liquid chromatography-tandem mass spectrometry—evaluation of the esterase inhibitor, diisopropyl fluorophosphate, in the stabilization of a labile ester-containing drug," J Chromatogr B Analyt Technol Biomed Life Sci. 852(1-2):77-84 (Jun. 1, 2007).

* cited by examiner

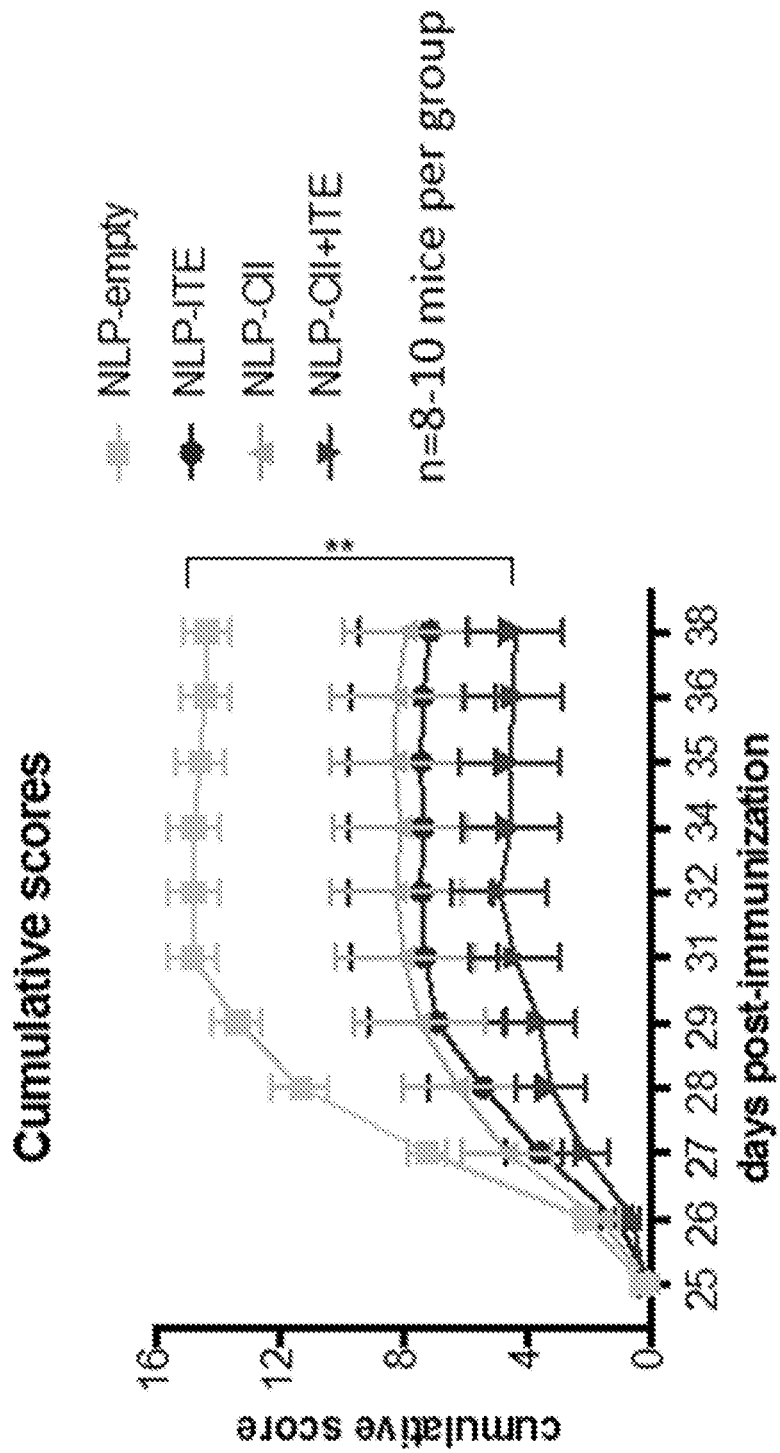

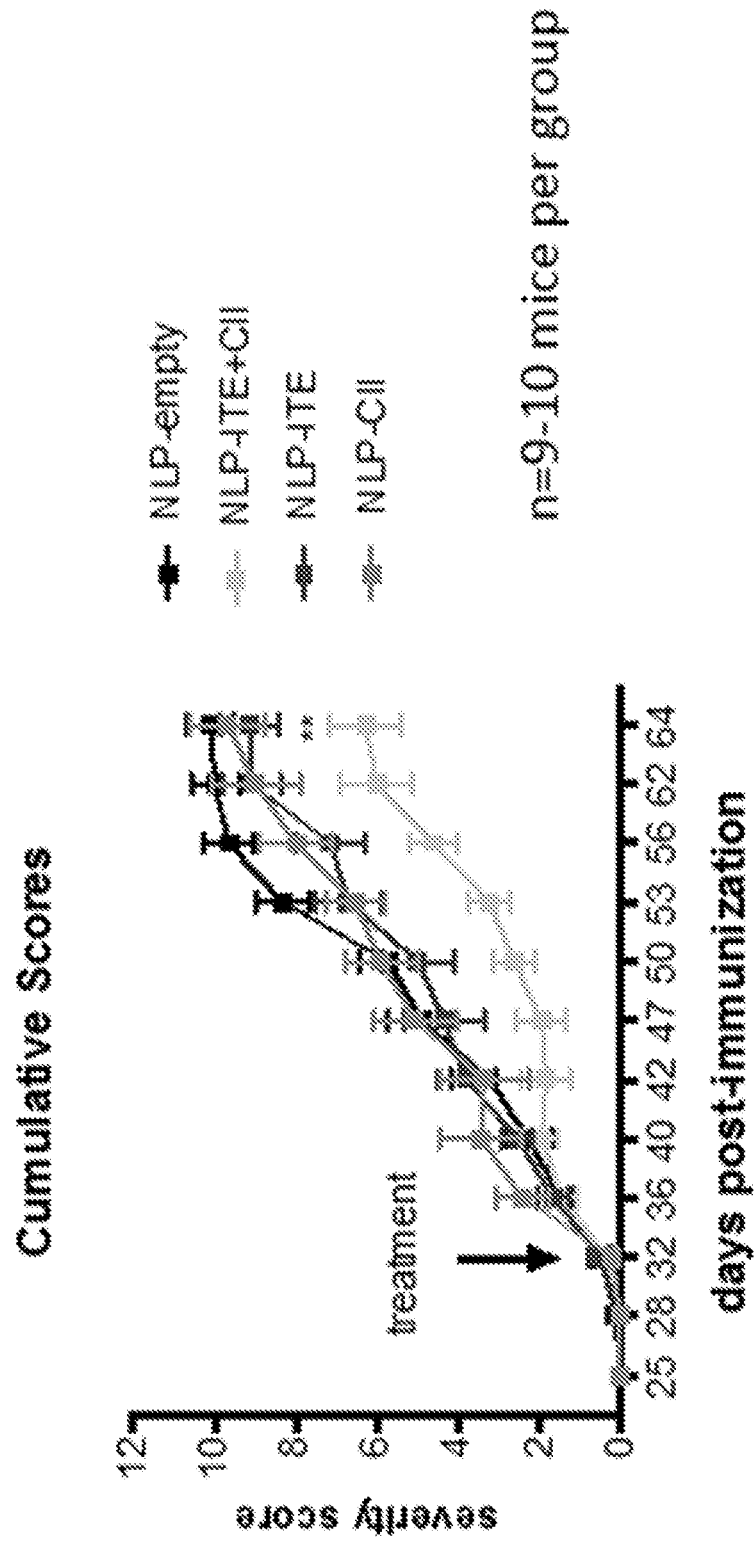

FIG. 13

| Trade name | International Non-proprietary name (INN) | Target | Type | Therapeutic Indication(s) |
|---|---|---|---|---|
| Amjevita® | Adalimumab | TNFα | Human IgG1 | juvenile arthritis; rheumatoid arthritis; psoriatic arthritis; ulcerative colitis; Crohn's disease; psoriasis; ankylosing spondylitis |
| Zinplava™ | Bezlotoxumab | C. difficile toxin B | Human antitoxin antibody | pseudomembranous enterocolitis |
| Bavencio® | Avelumab | PD-L1 | Human IgG1/k | metastatic Merkel cell carcinoma |
| Dupixent® | Dupilumab | IL-4Rα | Human IgG4 | Asthma; dermatitis |
| Imfinzi® | Durvalumab | PD-L1 | Human IgG1/k | Metastatic urothelial carcinoma |
| Ocrevus™ | Ocrelizumab | CD20 | Humanized IgG1k | Multiple sclerosis |
| Siliq | Brodalumab | IL-17RA | Human IgG2/k | Psoriasis |
| Cinqair™ | Reslizumab | IL-5 | Human IgG4/k | Asthma |
| Lartruvo | Olaratumab | PDGFR-α | Human IgG1 | Sarcoma |
| Darzalex® | Daratumumab | CD38 | Human IgG1/k | Multiple myeloma |
| Empliciti | Elotuzumab | SLAMF7 | Human IgG1 | Multiple myeloma |
| Portrazza | Necitumumab | EGFR | Human IgG1 | non-small-cell lung carcinoma |
| Inflectra | Infliximab | TNFα | Chimeric human-murine IgG1 | ankylosing spondylitis; rheumatoid arthritis; ulcerative colitis; psoriatic arthritis; Crohn's Disease; psoriasis |
| Anthim® | Obiltoxaximab | PA component of B. anthracis toxin | Chimeric (mouse/human) IgG1/k | anthrax infection |
| Tecentriq® | Atezolizumab | PD-L1 | Human IgG1 | metastatic non-small cell lung cancer |
| Cosentyx™ | Secukinumab | interleukin-17A | Human IgG1/k | psoriatic arthritis; psoriasis; ankylosing spondylitis |
| Nucala | Mepolizumab | IL-5 | Human IgG1/k | Asthma |
| Opdivo | Nivolumab | PD-1 | Human IgG4 | non-small-cell lung carcinoma; renal cell carcinoma; Hodgkin disease; melanoma |
| Praluent | Alirocumab | PCSK9 | Human IgG1 | dyslipidemias |
| Praxbind® | Idarucizumab | dabigatran etexilate | Human FaB | hemorrhage |
| Repatha® | Evolocumab | LDL-C / PCSK9 | Human IgG2 | dyslipidemias; hypercholesterolemia |
| Unituxin | Dinutuximab | GD2 | Human IgG1/k | neuroblastoma |
| Blincyto® | Bevacizumab | CD19 | BiTEs | precursor cell lymphoblastic leukemia-lymphoma |
| Keytruda® | Pembrolizumab | PD-1 | Human IgG4 | melanoma |
| Cyramza | Ramucirumab | VEGF | Human IgG1 | stomach neoplasms |

FIG. 13 cont.

| Trade name | International Non-proprietary name (INN) | Target | Type | Therapeutic Indication(s) |
|---|---|---|---|---|
| Entyvio® | Vedolizumab | Integrin-α4β7 | Humanized IgG1 | Colitis; ulcerative Crohn's disease |
| Sylvant® | Siltuximab | cCLB8 | Chimeric IgG1k | Giant lymph node hyperplasia |
| Lemtrada® | Alemtuzumab | CD52 | Humanized IgG1 | Multiple sclerosis |
| Kadcyla® | Trastuzumab emtansine | HER2 | Humanized IgG1 as ADC | Breast cancer |
| Perjeta® | Pertuzumab | HER2 | Humanized IgG1 | Breast cancer |
| Remsima® | Infliximab | TNF-alpha | Chimeric IgG1 Ab | Spondylitis; ankylosing arthritis; rheumatoid colitis; ulcerative Crohn's disease; arthritis; psoriatic psoriasis |
| Gazyvaro® | Obinutuzumab | CD20 | Humanized IgG1 | CLL |
| Adcetris® | Brentuximab | CD30 (conjugate of Mab and MMAE) | Chimeric IgG1 as ADC (antibody drug conjugate) | Hodgkin lymphoma (HL), systemic anaplastic large cell lymphoma (ALCL) |
| ABthrax® | Raxibacumab | Bacillus anthracis protective antigen | Human IgG1 | Prevention and treatment of anthrax inhalation |
| Benlysta® | Belimumab | BLyS | Human IgG1 | Systemic lupus erythematosus (SLE) |
| Vervoy® | Ipilimumab | CTLA-4 | Human IgG1 | Melanoma |
| Xgeva® | Denosumab | RANKL | Human IgG2 | Prevention of SREs in patients with bone metastases from solid tumours |
| Prolia® | Denosumab | RANKL | Human IgG2 | Osteoporosis |
| Arzerra® | Ofatumumab | CD20 | Human IgG1 | Chronic lymphocytic leukemia |
| Scintimun® (Diagnostic) | Besilesomab | NCA-95 | Murine IgG1 | In vivo diagnosis of inflammation / infection sites via scintigraphic imaging → non-therapeutic |
| RoActemra® | Tocilizumab | IL-6 receptor | Humanized IgG1 | Rheumatoid arthritis |
| Ilaris® | Canakinumab | IL-1β | Human IgG1 | Cryopyrin-associated periodic syndromes including familial cold autoinflammatory syndrome and Muckle-Wells syndrome; TNF receptor associated periodic syndrome (TRAPS); hyper IgD Syndrome (HIDS) /mevalonate kinase deficiency (MKD) and familial mediterranean fever |
| Simponi® | Golimumab | TNFa | Human IgG1 | Rheumatoid arthritis; psoriatic arthritis; ankylosing spondylitis |
| Stelara® | Ustekinumab | IL-12 / IL-23 | Human IgG1 | Plaque psoriasis |

FIG. 13 cont.

| Trade name | International Non-proprietary name (INN) | Target | Type | Therapeutic Indication(s) |
|---|---|---|---|---|
| Cimzia® | Certolizumab pegol | TNFa | Humanized IgG Fab fragment | Crohn's disease; rheumatoid arthritis |
| Removab® | Catumaxomab | EpCAM and CD3 | Trifunctional Mab IgG2a / IgG2b | Malignant ascites in patients with EpCAM-positive carcinomas |
| Soliris® | Eculizumab | Complement C5 | Humanized IgG2/4 | Paroxysmal nocturnal hemoglobinuria |
| Lucentis® | Ranibizumab | VEGF-A | Humanized IgG1 Fab fragment | Neovascular (wet) age-related macular degeneration; macular edema following retinalvein occlusion |
| Vectibix® | Panitumumab | EGFR | Human IgG2 | Metastatic colorectal carcinoma |
| Tysabri® | Natalizumab | VLA-4 | Humanized IgG4 | Multiple sclerosis (relapsing); Crohn's disease |
| Proxinium® | Calumaxomab | EpCAM | Humanized Mab | Head and neck cancer |
| Avastin® | Bevacizumab | VEGF | Humanized IgG1 | Metastatic colorectal cancer; non-small cell lung cancer; metastatic breast cancer; hlioblastoma multiforme; metastatic renal cell carcinoma |
| Xolair® | Omalizumab | IgE | Humanized IgG1 | Asthma |
| Erbitux® | Cetuximab | EGFR | Chimeric IgG1 | Head and neck cancer; colorectal cancer |
| Zevalin® | Ibritumomab tiuxetan | CD20 | Murine IgG1 | Non-Hodgkin's lymphoma |
| NeutroSpec® (Diagnostic) | Fanolesomab | CD15 | Murine MAb | Imaging of equivocal appendicitis → non-therapeutic |
| Humira® | Adalimumab | TNFα | Human IgG1 | Rheumatoid arthritis; juvenile idiopathic arthritis; psoriatic arthritis; ankylosing spondylitis; Crohn's disease; plaque psoriasis |
| Bexxar® | Tositumomab and iodine 131 tositumomab | CD20 | Murine IgG2a | Non-Hodgkin's lymphoma |
| Campath® | Alemtuzumab | CD52 | Humanized IgG1 | B-cell chronic lymphocytic leukemia |
| Herceptin® | Trastuzumab | HER-2 | Humanized IgG1 | Breast cancer; metastatic gastric or gastroesophageal junction adenocarcinoma |
| Remicade® | Infliximab | TNFα | Chimeric IgG1 | Crohn's disease; ulcerative colitis; rheumatoid arthritis; ankylosing spondylitis; psoriatic arthritis; plaque psoriasis |
| Synagis® | Palivizumab | F-protein of RS virus | Humanized IgG1 | Respiratory syncytial virus (RSV) |

FIG. 13 cont.

| Trade name | International Non-proprietary name (INN) | Target | Type | Therapeutic Indication(s) |
|---|---|---|---|---|
| Daclizumab | Necitumumab | CD25 (a chain of IL2 receptor) | Humanized IgG1 | Reversal of transplantation rejection |
| Simulect® | Basiliximab | CD25 (a chain of IL2 receptor) | Chimeric IgG1 | Reversal of transplantation rejection |
| Rituxan® MabThera® | Rituximab | CD20 | Chimeric IgG1 | Non-Hodgkin's lymphoma; chronic lymphocytic leukemia; rheumatoid arthritis |
| LeukoScan® (Diagnostic) | Sulesomab | NCA90 | Murine Fab fragment | Diagnostic imaging for forosteomyelitis → non-therapeutic |
| CEA-scan® (Diagnostic) | Arcitumomab | Human CEA (carcinoembryonic antigen) | Murine Fab fragment | Detection of colorectal cancer → non-therapeutic |
| ProstaScint® (Diagnostic) | Capromab | Tumor surface antigen PSMA | Murine MAb | Detection of prostate adenocarcinoma → non-therapeutic |
| Verluma® (Diagnostic) | Nofetumomab | Carcinoma-associated antigen | Murine Fab fragment | Diagnostic imaging of small celllung cancer → non-therapeutic |
| ReoPro® | Abciximab | GPIIb/IIIa | Chimeric IgG1 Fab | High risk angioplasty (prevention of blood clots) |

```
                            SEQUENCE LISTING

<160> NUMBER OF SEQ ID NOS: 82

<210> SEQ ID NO 1
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is Citrulline
<220> FEATURE:
<221> NAME/KEY: MISC_FEATURE
<222> LOCATION: (13)..(13)
<223> OTHER INFORMATION: Xaa is Citrulline
<220> FEATURE:
<221> NAME/KEY: MISC_FEATURE
<222> LOCATION: (15)..(15)
<223> OTHER INFORMATION: Xaa is Citrulline

<400> SEQUENCE: 1

Xaa Pro Ala Pro Pro Pro Ile Ser Gly Gly Gly Tyr Xaa Ala Xaa
1               5                   10                  15

<210> SEQ ID NO 2
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Citrulline
<220> FEATURE:
<221> NAME/KEY: MISC_FEATURE
<222> LOCATION: (7)..(7)
<223> OTHER INFORMATION: Xaa is Citrulline

<400> SEQUENCE: 2

Ala Xaa Gly Leu Thr Gly Xaa Pro Gly Asp Ala Lys
1               5                   10

<210> SEQ ID NO 3
<211> LENGTH: 21
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (9)..(9)
<223> OTHER INFORMATION: Xaa is Citrulline

<400> SEQUENCE: 3

His Gln Cys His Gln Glu Ser Thr Xaa Gly Arg Ser Arg Gly Arg Cys
1               5                   10                  15

Gly Arg Ser Gly Ser
            20

<210> SEQ ID NO 4
<211> LENGTH: 14
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is Citrulline

<400> SEQUENCE: 4

Ser Ala Val Arg Ala Xaa Ser Ser Val Pro Gly Val Arg Lys
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Synthetic Construct

<400> SEQUENCE: 5

Gln Pro Leu Ala Leu Glu Gly Ser Leu Gln Lys
1               5                   10

<210> SEQ ID NO 6
<211> LENGTH: 20
<212> TYPE: PRT
<213> ORGANISM: Artificial Sequence
<220> FEATURE:
<223> OTHER INFORMATION: Synthetic Construct

<400> SEQUENCE: 6

Gly Gly Gly Pro Gly Ala Gly Ser Leu Gln Pro Leu Ala Leu Glu Gly
1               5                   10                  15

Ser Leu Gln Lys
            20

<210> SEQ ID NO 7
<211> LENGTH: 18
<212> TYPE: PRT
<213> ORGANISM: Artificial Sequence
<220> FEATURE:
<223> OTHER INFORMATION: Synthetic Construct

<400> SEQUENCE: 7

Gly Ser Leu Gln Pro Leu Ala Leu Glu Gly Ser Leu Gln Lys Arg Gly
1               5                   10                  15

Ile Val

<210> SEQ ID NO 8
<211> LENGTH: 17
<212> TYPE: PRT
<213> ORGANISM: Artificial Sequence
<220> FEATURE:
<223> OTHER INFORMATION: Synthetic Construct

<400> SEQUENCE: 8

Gln Pro Leu Ala Leu Glu Gly Ser Leu Gln Lys Arg Gly Ile Val Glu
1               5                   10                  15

Gln

<210> SEQ ID NO 9
<211> LENGTH: 9
<212> TYPE: PRT
<213> ORGANISM: Artificial Sequence
<220> FEATURE:
```

<223> OTHER INFORMATION: Synthetic Construct

<400> SEQUENCE: 9

Ala Leu Trp Met Arg Leu Leu Pro Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

His Leu Val Glu Ala Leu Tyr Leu Val
1               5

<210> SEQ ID NO 11
<211> LENGTH: 15
<212> TYPE: PRT
<213> ORGANISM: Artificial Sequence
<220> FEATURE:
<223> OTHER INFORMATION: Synthetic Construct

<400> SEQUENCE: 11

Ser His Leu Val Glu Ala Leu Tyr Leu Val Cys Gly Glu Arg Gly
1               5                   10                  15

<210> SEQ ID NO 12
<211> LENGTH: 9
<212> TYPE: PRT
<213> ORGANISM: Artificial Sequence
<220> FEATURE:
<223> OTHER INFORMATION: Synthetic Construct

<400> SEQUENCE: 12

Asp Leu Gln Val Gly Gln Val Glu Leu
1               5

<210> SEQ ID NO 13
<211> LENGTH: 13
<212> TYPE: PRT
<213> ORGANISM: Artificial Sequence
<220> FEATURE:
<223> OTHER INFORMATION: Synthetic Construct

<400> SEQUENCE: 13

Val Ser Ser Gln Phe Ser Asp Ala Ala Gln Ala Ser Pro
1               5                   10

<210> SEQ ID NO 14
<211> LENGTH: 24
<212> TYPE: PRT
<213> ORGANISM: Artificial Sequence
<220> FEATURE:
<223> OTHER INFORMATION: Synthetic Construct

<400> SEQUENCE: 14

Ser Arg Val Ser Ser Val Ser Ser Gln Phe Ser Asp Ala Ala Gln Ala
1               5                   10                  15

Ser Pro Ser Ser His Ser Ser Thr
            20

<210> SEQ ID NO 15
<211> LENGTH: 15
<212> TYPE: PRT

```
<213> ORGANISM: Artificial Sequence
<220> FEATURE:
<223> OTHER INFORMATION: Synthetic Construct

<400> SEQUENCE: 15

Ser Ser Val Ser Ser Gln Phe Ser Asp Ala Ala Gln Ala Ser Pro
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic Construct

<400> SEQUENCE: 16

Ser Val Ser Ser Gln Phe Ser Asp Ala Ala Gln Ala Ser Pro Ser
1               5                   10                  15

<210> SEQ ID NO 17
<211> LENGTH: 19
<212> TYPE: PRT
<213> ORGANISM: Artificial Sequence
<220> FEATURE:
<223> OTHER INFORMATION: Synthetic Construct

<400> SEQUENCE: 17

Ser Val Ser Ser Gln Phe Ser Asp Ala Ala Gln Ala Ser Pro Ser Ser
1               5                   10                  15

His Ser Ser

<210> SEQ ID NO 18
<211> LENGTH: 24
<212> TYPE: PRT
<213> ORGANISM: Artificial Sequence
<220> FEATURE:
<223> OTHER INFORMATION: Synthetic Construct

<400> SEQUENCE: 18

Ser Val Ser Ser Gln Phe Ser Asp Ala Ala Gln Ala Ser Pro Ser Ser
1               5                   10                  15

His Ser Ser Thr Pro Ser Trp Cys
            20

<210> SEQ ID NO 19
<211> LENGTH: 15
<212> TYPE: PRT
<213> ORGANISM: Artificial Sequence
<220> FEATURE:
<223> OTHER INFORMATION: Synthetic Construct

<400> SEQUENCE: 19

Val Ser Ser Gln Phe Ser Asp Ala Ala Gln Ala Ser Pro Ser Ser
1               5                   10                  15

<210> SEQ ID NO 20
<211> LENGTH: 21
<212> TYPE: PRT
<213> ORGANISM: Artificial Sequence
<220> FEATURE:
<223> OTHER INFORMATION: Synthetic Construct

<400> SEQUENCE: 20

Val Ser Ser Val Ser Ser Gln Phe Ser Asp Ala Ala Gln Ala Ser Pro
1               5                   10                  15
```

Ser Ser His Ser Ser
        20

<210> SEQ ID NO 21
<211> LENGTH: 24
<212> TYPE: PRT
<213> ORGANISM: Artificial Sequence
<220> FEATURE:
<223> OTHER INFORMATION: Synthetic Construct

<400> SEQUENCE: 21

Val Ser Ser Gln Phe Ser Asp Ala Ala Gln Ala Ser Pro Ser Ser His
1               5                   10                  15

Ser Ser Thr Pro Ser Trp Cys Glu
            20

<210> SEQ ID NO 22
<211> LENGTH: 7
<212> TYPE: PRT
<213> ORGANISM: Artificial Sequence
<220> FEATURE:
<223> OTHER INFORMATION: Synthetic Construct

<400> SEQUENCE: 22

Thr Gln Glu Thr Arg Thr Leu
1               5

<210> SEQ ID NO 23
<211> LENGTH: 19
<212> TYPE: PRT
<213> ORGANISM: Artificial Sequence
<220> FEATURE:
<223> OTHER INFORMATION: Synthetic Construct

<400> SEQUENCE: 23

Ser Phe Tyr Leu Lys Asn Val Gln Thr Gln Glu Thr Arg Thr Leu Thr
1               5                   10                  15

Gln Phe His

<210> SEQ ID NO 24
<211> LENGTH: 19
<212> TYPE: PRT
<213> ORGANISM: Artificial Sequence
<220> FEATURE:
<223> OTHER INFORMATION: Synthetic Construct

<400> SEQUENCE: 24

Phe Tyr Leu Lys Asn Val Gln Thr Gln Glu Thr Arg Thr Leu Thr Gln
1               5                   10                  15

Phe His Phe

<210> SEQ ID NO 25
<211> LENGTH: 13
<212> TYPE: PRT
<213> ORGANISM: Artificial Sequence
<220> FEATURE:
<223> OTHER INFORMATION: Synthetic Construct

<400> SEQUENCE: 25

Tyr Leu Lys Asn Val Gln Thr Gln Glu Thr Arg Thr Leu
1               5                   10

<210> SEQ ID NO 26
<211> LENGTH: 15
<212> TYPE: PRT

<213> ORGANISM: Artificial Sequence
<220> FEATURE:
<223> OTHER INFORMATION: Synthetic Construct

<400> SEQUENCE: 26

Tyr Leu Lys Asn Val Gln Thr Gln Glu Thr Arg Thr Leu Thr Gln
1               5                   10                  15

<210> SEQ ID NO 27
<211> LENGTH: 15
<212> TYPE: PRT
<213> ORGANISM: Artificial Sequence
<220> FEATURE:
<223> OTHER INFORMATION: Synthetic Construct

<400> SEQUENCE: 27

Leu Lys Asn Val Gln Thr Gln Glu Thr Arg Thr Leu Thr Gln Phe
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic Construct

<400> SEQUENCE: 28

Lys Asn Val Gln Thr Gln Glu Thr Arg Thr Leu Thr Gln Phe His
1               5                   10                  15

<210> SEQ ID NO 29
<211> LENGTH: 14
<212> TYPE: PRT
<213> ORGANISM: Artificial Sequence
<220> FEATURE:
<223> OTHER INFORMATION: Synthetic Construct

<400> SEQUENCE: 29

Val Gln Thr Gln Glu Thr Arg Thr Leu Thr Gln Phe His Phe
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Synthetic Construct

<400> SEQUENCE: 30

Thr Gln Glu Thr Arg Thr Leu Thr Gln Phe His Phe
1               5                   10

<210> SEQ ID NO 31
<211> LENGTH: 8
<212> TYPE: PRT
<213> ORGANISM: Artificial Sequence
<220> FEATURE:
<223> OTHER INFORMATION: Synthetic Construct

<400> SEQUENCE: 31

Ala Tyr Gln Ala Glu Pro Asn Thr
1               5

<210> SEQ ID NO 32
<211> LENGTH: 17
<212> TYPE: PRT
<213> ORGANISM: Artificial Sequence

```
<220> FEATURE:
<223> OTHER INFORMATION: Synthetic Construct

<400> SEQUENCE: 32

Leu Ala Lys Glu Trp Gln Ala Leu Cys Ala Tyr Gln Ala Glu Pro Asn
1               5                   10                  15

Thr

<210> SEQ ID NO 33
<211> LENGTH: 24
<212> TYPE: PRT
<213> ORGANISM: Artificial Sequence
<220> FEATURE:
<223> OTHER INFORMATION: Synthetic Construct

<400> SEQUENCE: 33

Leu Ala Lys Glu Trp Gln Ala Leu Cys Ala Tyr Gln Ala Glu Pro Asn
1               5                   10                  15

Thr Cys Ala Thr Ala Gln Gly Glu
            20

<210> SEQ ID NO 34
<211> LENGTH: 18
<212> TYPE: PRT
<213> ORGANISM: Artificial Sequence
<220> FEATURE:
<223> OTHER INFORMATION: Synthetic Construct

<400> SEQUENCE: 34

Trp Gln Ala Leu Cys Ala Tyr Gln Ala Glu Pro Asn Thr Cys Ala Thr
1               5                   10                  15

Ala Gln

<210> SEQ ID NO 35
<211> LENGTH: 16
<212> TYPE: PRT
<213> ORGANISM: Artificial Sequence
<220> FEATURE:
<223> OTHER INFORMATION: Synthetic Construct

<400> SEQUENCE: 35

Leu Cys Ala Tyr Gln Ala Glu Pro Asn Thr Cys Ala Thr Ala Gln Gly
1               5                   10                  15

<210> SEQ ID NO 36
<211> LENGTH: 13
<212> TYPE: PRT
<213> ORGANISM: Artificial Sequence
<220> FEATURE:
<223> OTHER INFORMATION: Synthetic Construct

<400> SEQUENCE: 36

Ala Tyr Gln Ala Glu Pro Asn Thr Cys Ala Thr Ala Gln
1               5                   10

<210> SEQ ID NO 37
<211> LENGTH: 19
<212> TYPE: PRT
<213> ORGANISM: Artificial Sequence
<220> FEATURE:
<223> OTHER INFORMATION: Synthetic Construct

<400> SEQUENCE: 37

Ala Tyr Gln Ala Glu Pro Asn Thr Cys Ala Thr Ala Gln Gly Glu Gly
1               5                   10                  15
```

Asn Ile Lys

<210> SEQ ID NO 38
<211> LENGTH: 8
<212> TYPE: PRT
<213> ORGANISM: Artificial Sequence
<220> FEATURE:
<223> OTHER INFORMATION: Synthetic Construct

<400> SEQUENCE: 38

Cys Thr Val Ile Val Met Leu Thr
1               5

<210> SEQ ID NO 39
<211> LENGTH: 18
<212> TYPE: PRT
<213> ORGANISM: Artificial Sequence
<220> FEATURE:
<223> OTHER INFORMATION: Synthetic Construct

<400> SEQUENCE: 39

Asp Phe Trp Gln Met Val Trp Glu Ser Gly Cys Thr Val Ile Val Met
1               5                   10                  15

Leu Thr

<210> SEQ ID NO 40
<211> LENGTH: 20
<212> TYPE: PRT
<213> ORGANISM: Artificial Sequence
<220> FEATURE:
<223> OTHER INFORMATION: Synthetic Construct

<400> SEQUENCE: 40

Phe Trp Gln Met Val Trp Glu Ser Gly Cys Thr Val Ile Val Met Leu
1               5                   10                  15

Thr Pro Leu Val
            20

<210> SEQ ID NO 41
<211> LENGTH: 16
<212> TYPE: PRT
<213> ORGANISM: Artificial Sequence
<220> FEATURE:
<223> OTHER INFORMATION: Synthetic Construct

<400> SEQUENCE: 41

Trp Gln Met Val Trp Glu Ser Gly Cys Thr Val Ile Val Met Leu Thr
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: Synthetic Construct

<400> SEQUENCE: 42

Met Val Trp Glu Ser Gly Cys Thr Val Ile Val Met Leu Thr Pro Leu
1               5                   10                  15

<210> SEQ ID NO 43
<211> LENGTH: 21
<212> TYPE: PRT
<213> ORGANISM: Artificial Sequence
<220> FEATURE:

<223> OTHER INFORMATION: Synthetic Construct

<400> SEQUENCE: 43

Met Val Trp Glu Ser Gly Cys Thr Val Ile Val Met Leu Thr Pro Leu
1               5                   10                  15

Val Glu Asp Gly Val
            20

<210> SEQ ID NO 44
<211> LENGTH: 17
<212> TYPE: PRT
<213> ORGANISM: Artificial Sequence
<220> FEATURE:
<223> OTHER INFORMATION: Synthetic Construct

<400> SEQUENCE: 44

Glu Ser Gly Cys Thr Val Ile Val Met Leu Thr Pro Leu Val Glu Asp
1               5                   10                  15

Gly

<210> SEQ ID NO 45
<211> LENGTH: 18
<212> TYPE: PRT
<213> ORGANISM: Artificial Sequence
<220> FEATURE:
<223> OTHER INFORMATION: Synthetic Construct

<400> SEQUENCE: 45

Glu Ser Gly Cys Thr Val Ile Val Met Leu Thr Pro Leu Val Glu Asp
1               5                   10                  15

Gly Val

<210> SEQ ID NO 46
<211> LENGTH: 18
<212> TYPE: PRT
<213> ORGANISM: Artificial Sequence
<220> FEATURE:
<223> OTHER INFORMATION: Synthetic Construct

<400> SEQUENCE: 46

Ser Gly Cys Thr Val Ile Val Met Leu Thr Pro Leu Val Glu Asp Gly
1               5                   10                  15

Val Lys

<210> SEQ ID NO 47
<211> LENGTH: 14
<212> TYPE: PRT
<213> ORGANISM: Artificial Sequence
<220> FEATURE:
<223> OTHER INFORMATION: Synthetic Construct

<400> SEQUENCE: 47

Gly Cys Thr Val Ile Val Met Leu Thr Pro Leu Val Glu Asp
1               5                   10

<210> SEQ ID NO 48
<211> LENGTH: 14
<212> TYPE: PRT
<213> ORGANISM: Artificial Sequence
<220> FEATURE:
<223> OTHER INFORMATION: Synthetic Construct

<400> SEQUENCE: 48

Cys Thr Val Ile Val Met Leu Thr Pro Leu Val Glu Asp Gly

-continued

```
1               5                   10

<210> SEQ ID NO 49
<211> LENGTH: 11
<212> TYPE: PRT
<213> ORGANISM: Artificial Sequence
<220> FEATURE:
<223> OTHER INFORMATION: Synthetic Construct

<400> SEQUENCE: 49

Phe Glu Phe Ala Leu Thr Ala Val Ala Glu Glu
1               5                   10

<210> SEQ ID NO 50
<211> LENGTH: 18
<212> TYPE: PRT
<213> ORGANISM: Artificial Sequence
<220> FEATURE:
<223> OTHER INFORMATION: Synthetic Construct

<400> SEQUENCE: 50

Ser Lys Asp Gln Phe Glu Phe Ala Leu Thr Ala Val Ala Glu Glu Val
1               5                   10                  15

Asn Ala

<210> SEQ ID NO 51
<211> LENGTH: 21
<212> TYPE: PRT
<213> ORGANISM: Artificial Sequence
<220> FEATURE:
<223> OTHER INFORMATION: Synthetic Construct

<400> SEQUENCE: 51

Ser Lys Asp Gln Phe Glu Phe Ala Leu Thr Ala Val Ala Glu Glu Val
1               5                   10                  15

Asn Ala Ile Leu Lys
            20

<210> SEQ ID NO 52
<211> LENGTH: 13
<212> TYPE: PRT
<213> ORGANISM: Artificial Sequence
<220> FEATURE:
<223> OTHER INFORMATION: Synthetic Construct

<400> SEQUENCE: 52

Asp Gln Phe Glu Phe Ala Leu Thr Ala Val Ala Glu Glu
1               5                   10

<210> SEQ ID NO 53
<211> LENGTH: 17
<212> TYPE: PRT
<213> ORGANISM: Artificial Sequence
<220> FEATURE:
<223> OTHER INFORMATION: Synthetic Construct

<400> SEQUENCE: 53

Asp Gln Phe Glu Phe Ala Leu Thr Ala Val Ala Glu Glu Val Asn Ala
1               5                   10                  15

Ile

<210> SEQ ID NO 54
<211> LENGTH: 18
<212> TYPE: PRT
<213> ORGANISM: Artificial Sequence
```

```
<220> FEATURE:
<223> OTHER INFORMATION: Synthetic Construct

<400> SEQUENCE: 54

Phe Glu Phe Ala Leu Thr Ala Val Ala Glu Glu Val Asn Ala Ile Leu
1               5                   10                  15

Lys Ala

<210> SEQ ID NO 55
<211> LENGTH: 11
<212> TYPE: PRT
<213> ORGANISM: Artificial Sequence
<220> FEATURE:
<223> OTHER INFORMATION: Synthetic Construct

<400> SEQUENCE: 55

Lys Val Glu Ser Ser Pro Ser Arg Ser Asp Tyr
1               5                   10

<210> SEQ ID NO 56
<211> LENGTH: 17
<212> TYPE: PRT
<213> ORGANISM: Artificial Sequence
<220> FEATURE:
<223> OTHER INFORMATION: Synthetic Construct

<400> SEQUENCE: 56

Lys Leu Lys Val Glu Ser Ser Pro Ser Arg Ser Asp Tyr Ile Asn Ala
1               5                   10                  15

Ser

<210> SEQ ID NO 57
<211> LENGTH: 24
<212> TYPE: PRT
<213> ORGANISM: Artificial Sequence
<220> FEATURE:
<223> OTHER INFORMATION: Synthetic Construct

<400> SEQUENCE: 57

Lys Leu Lys Val Glu Ser Ser Pro Ser Arg Ser Asp Tyr Ile Asn Ala
1               5                   10                  15

Ser Pro Ile Ile Glu His Asp Pro
            20

<210> SEQ ID NO 58
<211> LENGTH: 12
<212> TYPE: PRT
<213> ORGANISM: Artificial Sequence
<220> FEATURE:
<223> OTHER INFORMATION: Synthetic Construct

<400> SEQUENCE: 58

Leu Lys Val Glu Ser Ser Pro Ser Arg Ser Asp Tyr
1               5                   10

<210> SEQ ID NO 59
<211> LENGTH: 19
<212> TYPE: PRT
<213> ORGANISM: Artificial Sequence
<220> FEATURE:
<223> OTHER INFORMATION: Synthetic Construct

<400> SEQUENCE: 59

Leu Lys Val Glu Ser Ser Pro Ser Arg Ser Asp Tyr Ile Asn Ala Ser
1               5                   10                  15
```

Pro Ile Ile

<210> SEQ ID NO 60
<211> LENGTH: 12
<212> TYPE: PRT
<213> ORGANISM: Artificial Sequence
<220> FEATURE:
<223> OTHER INFORMATION: Synthetic Construct

<400> SEQUENCE: 60

Lys Val Glu Ser Ser Pro Ser Arg Ser Asp Tyr Ile
1               5                   10

<210> SEQ ID NO 61
<211> LENGTH: 22
<212> TYPE: PRT
<213> ORGANISM: Artificial Sequence
<220> FEATURE:
<223> OTHER INFORMATION: Synthetic Construct

<400> SEQUENCE: 61

Lys Val Glu Ser Ser Pro Ser Arg Ser Asp Tyr Ile Asn Ala Ser Pro
1               5                   10                  15

Ile Ile Glu His Asp Pro
            20

<210> SEQ ID NO 62
<211> LENGTH: 9
<212> TYPE: PRT
<213> ORGANISM: Artificial Sequence
<220> FEATURE:
<223> OTHER INFORMATION: Synthetic Construct

<400> SEQUENCE: 62

Ser Leu Ser Pro Leu Gln Ala Glu Leu
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic Construct

<400> SEQUENCE: 63

Leu Leu Pro Pro Leu Leu Glu His Leu
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic Construct

<400> SEQUENCE: 64

Gly Leu Leu Tyr Leu Ala Gln Glu Leu
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic Construct

```
<400> SEQUENCE: 65

Val Leu Ala Gly Tyr Gly Val Glu Leu
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic Construct

<400> SEQUENCE: 66

Thr Leu Leu Thr Leu Leu Gln Leu Leu
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic Construct

<400> SEQUENCE: 67

Ser Leu Ala Ala Gly Val Lys Leu Leu
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic Construct

<400> SEQUENCE: 68

Val Leu Leu Thr Leu Val Ala Leu Ala
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic Construct

<400> SEQUENCE: 69

Leu Leu Leu Leu Leu Leu Leu Leu Leu
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic Construct

<400> SEQUENCE: 70

Leu Leu Leu Leu Leu Pro Pro Arg Val
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic Construct

<400> SEQUENCE: 71
```

```
Gly Met Ala Glu Leu Met Ala Gly Leu
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic Construct

<400> SEQUENCE: 72

Leu Met Ala Gly Leu Met Gln Gly Val
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic Construct

<400> SEQUENCE: 73

Arg Leu Tyr Gln Glu Val His Arg Leu
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic Construct

<400> SEQUENCE: 74

Ser Leu Leu Asp Phe Arg Arg Lys Val
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic Construct

<400> SEQUENCE: 75

Phe Leu Trp Ser Val Phe Met Leu Ile
1               5

<210> SEQ ID NO 76
<211> LENGTH: 8
<212> TYPE: PRT
<213> ORGANISM: Artificial Sequence
<220> FEATURE:
<223> OTHER INFORMATION: Synthetic Construct

<400> SEQUENCE: 76

Phe Leu Phe Ala Val Gly Phe Tyr
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic Construct

<400> SEQUENCE: 77
```

Arg Leu Leu Cys Ala Leu Thr Ser Leu
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic Construct

<400> SEQUENCE: 78

Lys Leu Gln Val Phe Leu Ile Val Leu
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic Construct

<400> SEQUENCE: 79

Phe Leu Ile Val Leu Ser Val Ala Leu
1               5

<210> SEQ ID NO 80
<211> LENGTH: 14
<212> TYPE: PRT
<213> ORGANISM: Artificial Sequence
<220> FEATURE:
<223> OTHER INFORMATION: Synthetic Construct

<400> SEQUENCE: 80

Thr Val Tyr Gly Ala Phe Asp Pro Leu Leu Ala Val Ala Asp
1               5                   10

<210> SEQ ID NO 81
<211> LENGTH: 14
<212> TYPE: PRT
<213> ORGANISM: Artificial Sequence
<220> FEATURE:
<223> OTHER INFORMATION: Synthetic Construct

<400> SEQUENCE: 81

Trp Ser Lys Met Asp Gln Leu Ala Lys Glu Leu Thr Ala Glu
1               5                   10

<210> SEQ ID NO 82
<211> LENGTH: 21
<212> TYPE: PRT
<213> ORGANISM: Artificial Sequence
<220> FEATURE:
<223> OTHER INFORMATION: Synthetic Construct

<400> SEQUENCE: 82

Met Glu Val Gly Trp Tyr Arg Ser Pro Phe Ser Arg Val Val His Leu
1               5                   10                  15

Tyr Arg Asn Gly Lys
            20

TOLEROGENIC LIPOSOMES AND METHODS OF USE THEREOF

FIELD OF THE INVENTION

The invention features tolerogenic liposomes (e.g., nano-size liposomes) for treating diseases and conditions associated with pathologic immune responses and methods for formulating and administering such compositions.

SEQUENCE LISTING

The instant application contains a Sequence Listing which has been submitted electronically in ASCII format and is hereby incorporated by reference in its entirety. Said ASCII copy, created on Feb. 13, 2023, is named "51172-002003_Sequence_Listing_2_13_23_ST25.txt" and is 20,560 bytes in size.

BACKGROUND

The human immune system includes the innate arm and the adaptive arm, the latter consisting of humoral (antibody-mediated) and cellular components. The adaptive immune response must distinguish between antigens associated with disease-causing microorganisms, such as parasites, bacteria, and viruses, which are the proper targets of immune responses, and antigens associated with self, which should not be targeted by the immune system. The diversity-generating mechanisms of the adaptive immune system do not make this distinction. Rather, a process referred to as tolerization causes auto-reactive immune cells to be deleted early in development. Failure of tolerance to occur, or subsequent loss of tolerance to host (self) antigens is associated with autoimmune diseases, a diverse collection of conditions which can affect one or many organs (e.g., brain, peripheral nervous system, liver, kidney, pancreas, gastrointestinal tract, joints, skin, eye, and ear).

Restoration of tolerance to self antigens in patients with autoimmune diseases is a long-sought, but so far elusive therapeutic goal. Administration of disease-associated autoantigens in a variety of formulations and routes of administration is effective at suppressing disease in animal models of autoimmune disease (e.g. experimental autoimmune encephalomyelitis in mice and rats; the NOD mouse model of autoimmune diabetes), but has been disappointing when tested in human patients.

Delivery of a tolerogenic signal to immune cells, or co-delivery of antigen and a tolerogenic signal, are promising approaches, supported by animal data, but they have not yet been adequately tested in humans to draw conclusions about their potential therapeutic utility.

Existing therapies for autoimmune diseases either globally suppress immunity (e.g. anti-proliferative agents like methotrexate, azathioprine or leflunomide), target one arm of the adaptive immune system (e.g. the B-cell depleting antibody rituximab), or globally suppress proinflammatory signals (e.g. anti-tumor necrosis factor alpha antibodies like infliximab and adalimumab). Thus, there is a need in the field for improved therapeutic strategies for selectively restoring tolerance to one or more autoantigens in cases of pathogenic immunity, such as autoimmune disease, transplant rejection, and graft-versus host disease.

A variety of innovative medical treatments, including peptide and protein therapeutics and gene therapies (often delivered using viral vectors), entail exposing a patient's immune system to new antigens (neoantigens), which are often recognized as foreign. Repeated administration of such non-native therapeutic compositions to patients can elicit immune recognition and subsequent loss of therapeutic effectiveness, and may induce dangerous side effects like anaphylaxis. There is a need for improved methods and compositions to prevent immune recognition of neoantigens and/or selectively enforce immunologic tolerance to such immunogenic therapeutic compositions.

SUMMARY

The present invention features tolerogenic liposomes (e.g., nano-size liposomes) for treatment of pathologies of the immune system, such as autoimmunity; for preventing or reversing immune recognition of neoantigens associated with therapeutic proteins or gene therapy vectors; and for induction or maintenance of tolerance to otherwise potentially immunogenic therapeutic compositions, by efficient delivery of a lipophilic aryl hydrocarbon receptor agonist (e.g., ITE), which can be formulated for uptake by antigen-presenting cells (e.g., antigen-presenting cells of the immune system, such as dendritic cells), or co-delivered with one or more antigen(s), selected according to the disease being treated, or according to the therapeutic protein or viral vector against which immune tolerance is to be induced to potentiate efficacy.

In a first aspect, the invention features a composition including a population of liposomes. The population of liposomes can have an average diameter from 50 to 250 nanometers (nm; e.g., from 50 to 250 nm, from 50 to 200 nm, from 50 to 150 nm, from 75 to 125 nm, from 80 to 120 nm, from 90 to 110 nm, or from 95 to 105 nm, e.g., about 60 nm, about 70 nm, about 80 nm, about 90 nm, about 95 nm, about 100 nm, about 105 nm, about 110 nm, about 120 nm, or about 125 nm). The population of liposomes can further have an average desaturation index of 0.3 or greater (e.g., 0.4 or greater) and an average from 200-15,000 molecules of 2-(1H-Indol-3-ylcarbonyl)-4-thiazolecarboxylic acid methyl ester (ITE), or salt thereof, per liposome. In some embodiments, the population of liposomes has an average phase transition temperature from 0° C. to 70° C. In some embodiments, the population of liposomes includes a lipid mixture comprising a saturated lipid species and an unsaturated lipid species (e.g., a monounsaturated lipid species), wherein the unsaturated lipid species has an unsaturated bond and accounts for at least 50% of the lipid mixture (e.g., at least 55%, at least 60%, at least 65%, at least 70% or at least 75% by molar percentage). In some embodiments, the unsaturated lipid species has two lipid tails, wherein one or both lipid tails includes a single unsaturated bond. In some embodiments, the unsaturated lipid species is derived from natural sources such as egg or soy, and may comprise a mixture of lipids (e.g. differing in fatty acid chain length). In alternative embodiments, the unsaturated lipid species is produced synthetically and consists of a single defined phospholipid compound.

In some embodiments, the population of liposomes has an average phase transition temperature from −60° C. to 80° C. In some embodiments, the population of liposomes includes a lipid mixture comprising a saturated lipid species and an unsaturated lipid species (e.g., a monounsaturated lipid species), wherein the unsaturated lipid species has an unsaturated bond and accounts for at least 20% of the lipid mixture (e.g., at least 20%, at least 25%, at least 30%, at least 35%, at least 40%, at least 45%, at least 50% or more, by mass or by molar percentage). In some embodiments, the unsaturated lipid species has two lipid tails, wherein one or both lipid tails includes a single unsaturated bond. In some embodiments, the unsaturated lipid species is derived from natural sources such as egg or soy, and may comprise a mixture of lipids. In alternative embodiments, the unsaturated lipid species is produced synthetically and consists of a single defined phospholipid compound.

In another aspect, the invention features a composition including a population of liposomes having an average diameter from 50 to 250 nm (e.g., 75-125 nm, or 90-120 nm), wherein the population of liposomes has an average phase transition temperature from 0° C. to 70° C.; and an average from 150-15,000 (e.g., 200-15,000) molecules of ITE, or salt thereof, per liposome. In some embodiments, the population of liposomes has an average desaturation index of 0.3 or greater (e.g., 0.4 or greater). In one embodiment, the population of liposomes is produced from a lipid mixture comprising a saturated lipid species and an unsaturated lipid species, wherein the unsaturated lipid species comprises an unsaturated bond and accounts for at least 20% (e.g., at least 50%) of the lipid mixture. In some embodiments, the unsaturated lipid species comprises two lipid tails, wherein one or both lipid tails comprise a single unsaturated bond. In some embodiments, the head group of at least one phospholipid species is modified by covalent attachment of a poly(ethylene glycol) chain of at least 20 ethylene glycol units.

In yet another aspect, the invention features a composition including a population of liposomes having an average diameter from 50 to 250 nm (e.g., 75-125 nm, or 90-120 nm). This population of liposomes can include a lipid mixture having a saturated lipid species and an unsaturated lipid species, wherein the unsaturated lipid species comprises an unsaturated bond and accounts for at least 50% of the lipid mixture. This population of liposomes may have an average from 150-15,000 molecules of ITE per liposome. In some embodiments, the population of liposomes has an average phase transition temperature from 0° C. to 70° C. Additionally or alternatively, the population of liposomes may have an average desaturation index of 0.3 or greater. In some embodiments, the unsaturated lipid species comprises two lipid tails, wherein one or both lipid tails has a single unsaturated bond. In some embodiments, the unsaturated carbon-carbon bond is at least the third carbon-carbon bond (e.g., the third, fourth, fifth, seventh, eighth, ninth, tenth, eleventh, or twelfth carbon-carbon bond) from the free end of the lipid (e.g. the end not covalently bound to glycerol). In some embodiments, the unsaturated carbon-carbon bond is the ninth carbon-carbon bond from the free end of the lipid, as in egg PC.

In some embodiments of any of the preceding aspects, the population of liposomes may further include an antigen at a mass ratio of antigen-to-ITE from 1:10 to 100:1 (e.g., from 1:10 to 10:1). Additionally or alternatively, the population of liposomes may further include an antigen at a molar ratio of antigen-to-ITE from 25:1 to 1:200 (if the antigen is a peptide 8-50 amino acids in length) or a molar ratio from 4:1 to 1:5000 (if the antigen is a protein). For multi-protein assemblies (e.g. viral capsids) the mass and molar ratios may exceed these ranges.

In another aspect, the invention features a composition of a population of liposomes having an average diameter from 50 to 250 nanometers (nm; e.g., 75-125 nm, or 90-120 nm), wherein the population of liposomes has (i) an average from 150-15,000 molecules of ITE, or salt thereof per liposome, and (ii) an antigen at a mass ratio of antigen-to-ITE from 1:10 to 100:1 (e.g., 1:10 to 10:1). In some embodiments, the population of liposomes has an average desaturation index of 0.3 or greater. Additionally or alternatively, the population of liposomes comprises an average phase transition temperature from 0° C. to 70° C. In some embodiments, the population of liposomes comprises a lipid mixture having a saturated lipid species and an unsaturated lipid species, wherein the unsaturated lipid species has an unsaturated bond and accounts for at least 50% of the lipid mixture. In some embodiments, the unsaturated lipid species comprises two lipid tails, wherein each lipid tail comprises a single unsaturated bond.

In some embodiments, the antigen is a peptide antigen (e.g., a peptide antigen associated with an autoimmune disorder, such as rheumatoid arthritis, multiple sclerosis, type I diabetes, myasthenia gravis, inflammatory bowel disease, or celiac disease). The peptide may comprise one or more post-translational changes such as glycosylation, lipidation, or modification of an amino acid side change (e.g. changing arginine or lysine to citrulline). For example, in some embodiments, the peptide antigen includes an amino acid sequence of any of SEQ ID NOs: 1-81. In some embodiments, the peptide antigen includes an amino acid sequence having at least 90%, at least 91%, at least 92%, at least 93%, at least 94%, at least 95%, at least 96%, at least 97%, at least 98%, or at least 99% sequence identity to any of SEQ ID NOs: 1-81. In some embodiments, the peptide is associated with rheumatoid arthritis (e.g., a citrullinated beta fibrinogen peptide, citrullinated collagen type II peptide, citrullinated filaggrin peptide, or citrullinated vimentin peptide, e.g., having the amino acid sequence of any of SEQ ID NOs: 1-4). In some embodiments, the antigen and/or peptide is associate with type 1 diabetes or latent autoimmune diabetes of adults (LADA) (e.g., preproinsulin peptide, IA-2 peptide, phogrin peptide, IGRP peptide, GAD65 peptide, or chromogranin A peptide, e.g., antigens having amino acid sequences of any of SEQ ID NOs: 5-81).

In some embodiments, the invention provides methods of tolerizing a subject to a therapeutic agent (e.g. a recombinant protein such as factor VIII). In some embodiments, the invention provides methods of reducing the immune response (e.g., cytokine secretion, antibody generation, etc.) directed to a therapeutic agent. In some embodiments, the antigen against which tolerance is to be established is a therapeutic agent, e.g., a therapeutic recombinant protein or a portion thereof.

In some embodiments, the antigen is derived from a vector used to deliver a nucleic acid (i.e., a gene therapy vector). Gene therapy vectors include natural and engineered viral vectors as well as non-viral proteins, glycoproteins, lipids, polysaccharides and other natural or non-natural polymers used to package and protect nucleic acids from nucleases, and/or to target nucleic acids to specific organs or cell types. The nucleic acid may encode a gene or part of a gene, or it may comprise DNA fragments used to correct an endogenous gene, for example, as in CRISPR (clustered regularly interspaced short palindromic repeats) gene editing technology. Any component of a gene therapy vector which can be recognized by the immune system of a patient receiving treatment (i.e., any neoantigen) constitutes an antigen against which induction of immune tolerance may improve the utility of gene therapy.

In some embodiments, the therapeutic agent is immunogenic. In some embodiments, the therapeutic agent is a therapeutic protein or peptide. In some embodiments, the therapeutic agent is a virus or capsid protein thereof. In other embodiments, the therapeutic agent is a polynucleotide encoding the therapeutic protein or peptide and/or the virus or capsid protein thereof.

In some embodiments, the therapeutic agent is a viral vector, e.g., an AAV, or capsid protein thereof. In some embodiments, the viral vector, e.g., AAV, includes DNA. In some embodiments, the DNA is a single stranded DNA (ssDNA), such as, a cDNA or fragment thereof (e.g., a human cDNA or fragment thereof). In other embodiments, the viral vector, e.g., AAV includes RNA. In some embodiments, the RNA is a microRNA (miRNA).

In any of the preceding embodiments, the population of liposomes has an average zeta potential between −10 and −50 mv. In alternative embodiments, the population of liposomes has an average zeta potential between +10 and +40 mv. Alternatively, the population of liposomes has an average zeta potential from −50 and +40 mv.

In another aspect, the invention features a method of treating a subject having an autoimmune disorder. The method may include administering to the subject the composition of any of the preceding embodiments in a therapeutically effective amount. The administration may be an oral, intravenous, subcutaneous, intradermal (e.g., intra-epidermal), transdermal, intra-articular, pulmonary, or mucosal administration. In some embodiments, a dose of the composition administered comprises from 50 µg to 15 mg ITE, (e.g., from 75 µg to 10 mg, from 75 µg to 7.5 mg, from 100 µg to 7.5 mg, from 150 µg to 5 mg, from 200 µg to 5 mg, or from 250 µg to 2.5 mg ITE, e.g., from 50 µg to 100 µg, from 100 µg to 150 µg, from 150 µg to 200 µg, from 200 µg to 250 µg, from 250 µg to 300 µg, from 300 µg to 350 µg, form 350 µg to 400 µg, from 400 µg to 450 µg, from 450 µg to 500 µg, from 500 µg to 600 µg, from 600 µg to 700 µg, from 700 µg to 800 µg, from 800 µg to 900 µg, from 900 µg to 1.0 mg, from 1.0 mg to 5.0 mg, from 5.0 mg to 10 mg or from 10 mg to 15 mg ITE). In some embodiments, the subject has, or is at risk of developing, (e.g. based on genetic predisposition, family history or serologic biomarkers), an autoimmune disease such as, for example, type I diabetes, rheumatoid arthritis or celiac disease, or will be treated with a potentially antigenic therapeutic peptide, protein, viral vector, nucleic acid or cell composition. In any of these embodiments, the liposome or composition thereof may include the therapeutic protein or peptide (e.g., antibody), or portion thereof (e.g., a therapeutic protein described in FIG. 13 or a portion thereof).

In some embodiments, a dose of the composition administered comprises from 1 µg to 10 mg ITE, (e.g., from 10 µg to 10 mg, from 50 µg to 5 mg, from 100 µg to 1 mg, from 150 µg to 500 µg, from 200 µg to 400 µg, or from 250 µg to 250 µg ITE, e.g., from 1 µg to 10 µg, from 10 µg to 50 µg, from 50 µg to 100 µg, from 100 µg to 150 µg, from 150 µg to 200 µg, from 200 µg to 250 µg, from 250 µg to 300 µg, from 300 µg to 350 µg, form 350 µg to 400 µg, from 400 µg to 450 µg, from 450 µg to 500 µg, from 500 µg to 600 µg, from 600 µg to 700 µg, from 700 µg to 800 µg, from 800 µg to 900 µg, from 900 µg to 1.0 mg, from 1.0 mg to 5.0 mg, or from 5.0 mg to 10 mg ITE). In some embodiments, the subject has, or is at risk of developing, rheumatoid arthritis or type 1 diabetes.

In another aspect, the invention features methods for improving the efficacy and safety of peptide, protein or gene therapy by inducing immune tolerance to one or more neoantigens associated with the therapeutic composition (e.g., any of the compositions listed in FIG. 13), and thereby improving the pharmacokinetics (e.g. prolonging the half life), the delivery (e.g., increasing the efficiency of viral transduction), the efficacy of multiple dose treatment regimens (which would otherwise induce blocking immune responses) and the safety (e.g. preventing allergic reactions) of the treatment (e.g., any of the compositions listed in FIG. 13), among other benefits. The methods may include administering to the subject the composition of any of the preceding embodiments, via the routes of administration of any of the preceding embodiments, in a therapeutically effective amount.

In another aspect, the invention features a method of synthesizing or manufacturing a population of tolerogenic liposomes (e.g., nano-sized liposomes). The method may include the following steps: (i) mixing two or more lipid species to form a lipid mixture, wherein the lipid mixture has (a) an average desaturation index of 0.3 or greater; (b) an average phase transition temperature from 0° C. to 70° C.; or (c) a saturated lipid species and an unsaturated lipid species, wherein the unsaturated lipid species comprises an unsaturated bond and accounts for at least 50% of the lipid mixture. Step (ii) includes adding ITE to the lipid mixture, either as a dry powder, or wherein the ITE is dissolved in a solvent, such as dimethylsulfoxide (DMSO), and is added to the lipid mixture (dissolved in ethanol) at an amount of ITE from 0.4% to 1% by mass of lipid, e.g. from 0.5% to 1%, from 0.55% to 0.95%, from 0.6% to 0.85%, or from 0.65% to 0.75%. Step (iii) includes adding the lipid mixture containing ITE (dissolved in an ethanolic solution) to an aqueous phase and mixing to form crude liposomes. Next, step (iv) involves extruding the crude liposomes (e.g., through filters of selected pore size) to form a population of tolerogenic nanoparticulate liposomes (e.g., in a defined size range, e.g., 50-250 nm in diameter). In some embodiments, the population of tolerogenic nanoparticulate liposomes is the composition of any of the preceding aspects. In some embodiments, the aqueous interior of the liposomes comprises one or more antigens.

BRIEF DESCRIPTION OF THE DRAWINGS

FIGS. 9A and 9B are graphs showing the cumulative severity scores and number of arthritic limbs of mice with collagen-induced arthritis to disease prevention with liposomes (plain, loaded with collagen type II, loaded with ITE and loaded with ITE+collagen type II loaded) started on day −1 of disease initiation (disease prevention model).

FIGS. 11A, 11B, and 11C are a set graphs showing responses of mice with collagen-induced arthritis to therapy with liposomes (plain, loaded with collagen type II, loaded with ITE and loaded with ITE+collagen type II loaded) started on day 32 post disease initiation (disease therapy model). Cumulative severity scores (11A), number of arthritic limbs (11B) and average paw thickness (11C) are shown.

FIG. 13 is a tabulated summary of various approved therapeutic antibodies.

DETAILED DESCRIPTION

Figure 1A:
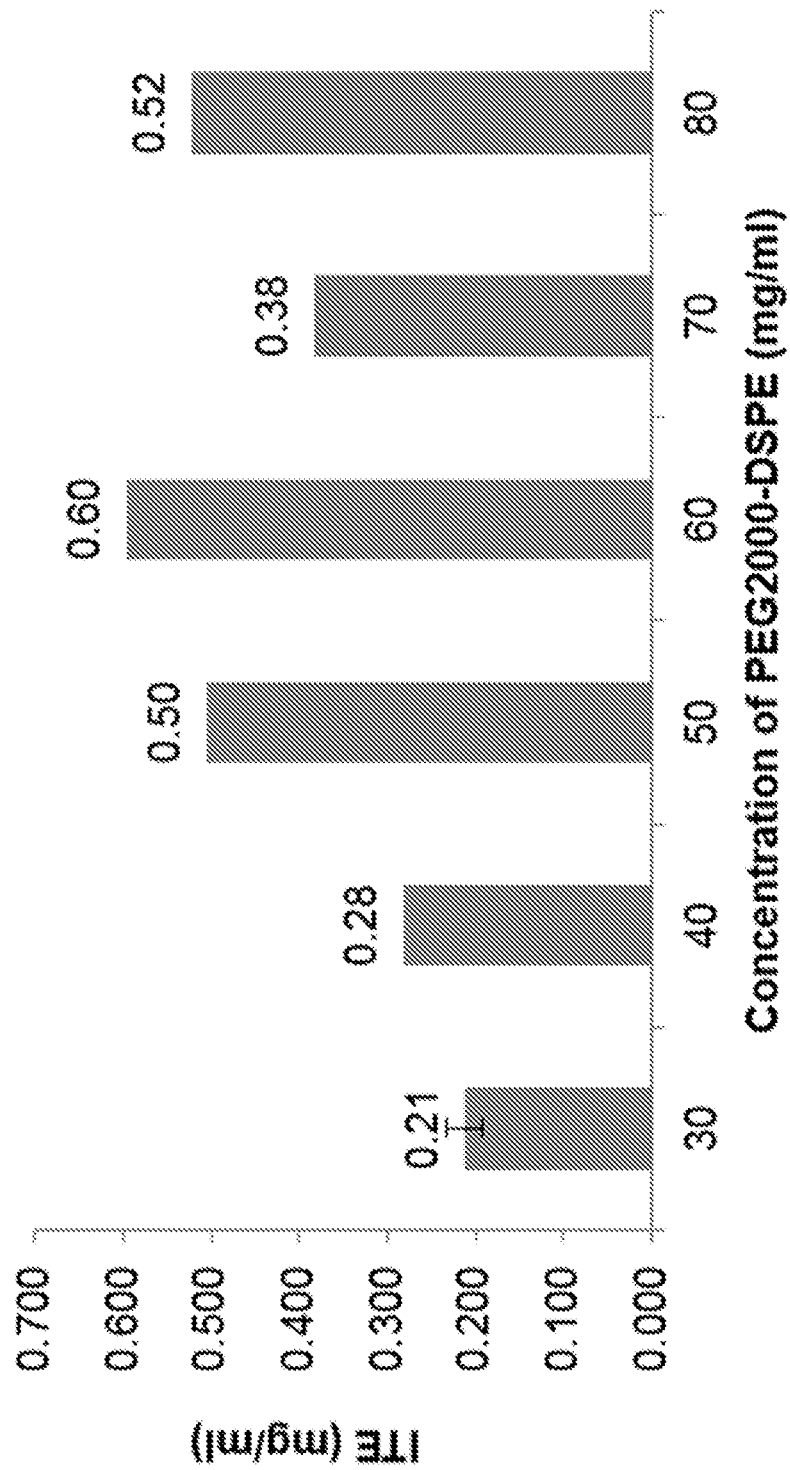
FIG. 1A is a chart showing ITE encapsulation efficiency in PEG2000-DSPE micelles over various concentrations of PEG2000-DSPE.

The present invention features tolerogenic liposomes (e.g., nanoparticulate liposomes) useful as treatment for diseases, such as autoimmune diseases (e.g., rheumatoid arthritis, multiple sclerosis, type I diabetes, myasthenia gravis, inflammatory bowel disease, and celiac disease). Further, the invention provides safe and efficient administration (including repeated administration) of potentially immunogenic therapeutic compositions, including therapeutic peptides and proteins, viral gene therapy vectors, nucleic acid therapeutics and cell therapies (e.g., via blood transfusion). Tolerogenic liposomes can also be used to reduce or prevent rejection of transplanted organs (e.g., kidney, liver, lung, heart, or bone marrow transplants) and to prevent or treat graft versus host disease. In particular, the invention features liposomes having a lipid composition configured to efficiently carry the tolerance-inducing aryl hydrocarbon receptor ligand 2-(1H-Indol-3-ylcarbonyl)-4-thiazolecarboxylic acid methyl ester (ITE), or salt thereof, as a tolerogenic agent to antigen-presenting cells, such as dendritic cells, along with relevant antigens.

Definitions

Unless defined otherwise, technical and scientific terms used herein have the same meaning as commonly understood by one of ordinary skill in the art to which this invention belongs and by reference to published texts, which provide one skilled in the art with a general guide to many of the terms used in the present application. In the event of any conflicting definitions between those set forth herein and those of a referenced publication, the definition provided herein shall control.

As used herein, the terms "nano-size liposome" and "liposome" refer to a spherical membrane-bound vesicle having a diameter of between 50 and 250 nanometers (nm). In particular embodiments, the liposome is unilamellar; however, multilamellar liposomes are also useful and encompassed by the present invention. The diameter of liposomes can be measured using any suitable method known in the art, such as dynamic light scattering (DLS; e.g., using a ZetaSizer instrument; Malvern Panalytical, Malvern, UK), Brownian motion analysis (e.g., nanoparticle tracking analysis, as provided by NanoSight instruments; Malvern Panalytical, Malvern, UK), etc.

As used herein, the term "micelle" refers to a substantially spherical particle characterized by a hydrophobic core and a hydrophilic shell formed by assembly of amphiphilic molecules (e.g., amphiphilic polymers). In certain embodiments, micelles self-assemble into the core-shell configuration when the amphiphilic polymer exceeds a critical threshold concentration in a suitable solvent (e.g., an aqueous solution). The exterior (hydrophilic) moiety may be a polyethylene glycol (e.g., PEG-500, PEG-1000, PEG-2000, PEG-3000, PEG-5000, where the number refers to the approximate molecular weight. (Each ethylene glycol unit of poly[ethylene glycol] contributes 44 Daltons, plus a non-repeating terminal group, so PEG-1000 contains about 22 ethylene glycol units). The interior moiety of the amphiphile can be a lipid, a polymer, an amino acid, an aromatic compound, or a combination. Examples of micelles include polymer-lipid micelles (e.g., with polyethylene glycol on the outside and a fatty acid, such as oleic acid, on the inside), polymer-phospholipid-micelles (e.g., hybrid polymeric micelles (e.g. with a hydrophilic polymer, such as polyethylene glycol on the outside and a relatively hydrophobic polymer, such as poly(D,L-lactide) in the interior). The hydrophilic and hydrophobic moieties of the amphiphile can be joined by a variety of chemical groups using standard attachment chemistry. For example, PEG may be joined to a lipid via phosphoglycerol. Amide, ester, and other linkages are also known in the art. Amphiphiles suitable for forming micelles are commercially available from a variety of vendors (e.g. Avanti Polar Lipids, Millipore-Sigma).

As used herein, the term "cholesterol" refers broadly to cholesterol, related sterols and derivatives thereof that can be combined with phospholipids to form liposomes. That is, "cholesterol" encompasses cholesterol-like molecules such as phytosterols (for example β-sitosterol or stigmasterol). The term "cholesterol" also encompasses sterol-modified phospholipids in which the sn-1 or sn-2 position of glycerol is covalently attached to cholesterol (via a linker) and the other position is attached to a fatty acid chain. See Huang and Szoka, *J. Am. Chem. Soc.* 2008, 130(46): 15702-15712, which is hereby incorporated herewith in its entirety. Sterol-modified phospholipids suitable for forming liposomes are commercially available from Avanti Polar Lipids (Alabaster, Alabama).

As used herein, the term "lipid mixture" refers to a mixture of mono- and/or diacylphospholipids (collectively phospholipids) with cholesterol, used in a liposome recipe. Phospholipids with different headgroups (attached to glycerol) or different acyl chains (esterified to glycerol) may be combined with cholesterol in different ratios to produce liposomes with desired characteristics (e.g., efficient and stable ITE loading). The lipid components in a lipid mixture can be characterized in terms of the molar ratio of the lipid species, expressed in percent terms (i.e., where the lipid components of a liposome sum to 100%). For example, a liposome mixture consisting of 39 mM phospholipid A (65%), 3 mM phospholipid B (5%) and 18 mM cholesterol (30%) is a 65:5:30 mixture. Ranges for useful lipid mixtures are provided herein.

As used herein, the term "desaturation index" refers to the weighted average of the number of double bonds per fatty acid, taking into account all phospholipid species as well as cholesterol (i.e. all components of a lipid mixture). A first double bond in a fatty acid chain is assigned full weight (1). The second double bond is assigned 0.4 weight if present in the second fatty acid of the same phospholipid, or 0.5 weight if present in a different phospholipid. Additional double bonds in the same fatty acid are given $\frac{1}{4}$, $\frac{1}{8}$, $\frac{1}{16}$, and so forth, the weight of the first unsaturated bond (i.e. $\frac{1}{4}$, $\frac{1}{8}$, $\frac{1}{16}$, etc. of 1, 0.5 or 0.4). For example, a liposome having an equimolar amount of two phospholipid species, wherein one species has two saturated fatty acid tails, and the other species has one saturated tail and one monounsaturated tail (i.e., 1 in 4 fatty acid tails are unsaturated at a single bond) has a desaturation index of 0.25. A liposome made from the same two phospholipids, combined with cholesterol at 30%, making a molar ratio of 35:35:30, has a desaturation index of 0.175. A liposome having an equimolar amount of two lipid species, wherein one species has two saturated fatty acid tails, and the other species has two monounsaturated tails, has a desaturation index of 0.35 (0.25+0.10; i.e., the first unsaturated fatty acid tail contributes 1×0.25 weight and the second 0.4×0.25 weight). A liposome having an equimolar amount of two lipid species, wherein one species has two saturated fatty acid tails, and the other species has one monounsaturated tail and one diunsaturated tail, has a desaturation index of 0.375 (0.25+0.10+0.025). Additional examples are provided in the Detailed Description.

As used herein, the term "subject" includes any mammal in need of the methods of treatment or prophylaxis described herein. In some embodiments, the subject is a human. Other mammals in need of such treatment or prophylaxis include dogs, cats, or other domesticated animals, horses, livestock, laboratory animals, including non-human primates, etc. The subject may be male or female. In one embodiment, the subject has an autoimmune disease. In other embodiments the subject is to receive potentially immunogenic peptide, protein or gene therapy. The subject may be any age during which treatment or prophylactic therapy may be beneficial. For example, in some embodiments, the subject is 0-5 years of age, 5-10 years of age, 10-20 years of age, 20-30 years of age, 30-50 years of age, 50-70 years of age, or more than 70 years of age.

As used herein, the term "neoantigen" refers to a molecule or portion of a molecule associated with a therapeutic agent (e.g. peptide, protein or gene therapy) that is recognized by the immune system and is capable of inducing an immune response. The nature of the immune response may be humoral (e.g., neutralizing antibodies against the neoantigen that inhibit function, shorten half-life or trigger degradation), cellular (e.g., T cell receptor recognition of peptides derived from the neoantigen), or both. Immune responses to neoantigens generally interfere with therapeutic efficacy.

As used herein, the term "gene therapy" refers to any nucleic acid-based therapeutic (whether composed of natural nucleotides or non-natural nucleotides) designed to replace, correct (e.g., by gene editing or targeted recombination) or alter the expression of (e.g., by oligonucleotide-induced exon skipping or RNA interference) an endogenous gene, or, in the case of cancer therapy, provide a novel function designed to exploit a vulnerability of cancer cells.

As used herein, the term "gene therapy vector" refers to components of a gene therapy composition designed to protect (e.g., from nucleases), steer (e.g., to targeted cells or tissues), enhance cell penetrance of (e.g., by viral transduction), or otherwise improve the efficacy of gene therapy. Often one or more components of a gene therapy vector comprise non-native elements capable of inducing an immune response. Viral gene therapy vectors comprise one important category of gene therapy vectors. The most widely used viral vectors include adenoviruses, adeno-associated viruses (AAV), herpes simplex viruses, lentiviruses, poxviruses, retroviruses and vaccinia viruses, all of which have multiple variants.

As used herein, an "effective amount" or "effective dose" of a composition thereof refers to an amount sufficient to achieve a desired biological (e.g., immunological) and/or pharmacological effect, e.g., when delivered to a cell or organism according to a selected administration form, route, and/or schedule. As will be appreciated by those of ordinary skill in this art, the absolute amount of a particular composition that is effective can vary depending on such factors as the desired biological or pharmacological endpoint (e.g., improved therapeutic efficacy or prolongation of therapeutic effect), the agent to be delivered, the target tissue, the route of administration, the age and size of the subject being treated, the stage of disease, etc. Those of ordinary skill in the art will further understand that an "effective amount" can be contacted with cells or administered to a subject in a single dose or through use of multiple doses.

As used herein, the term "treatment," or a grammatical derivation thereof, is defined as reducing the progression of a disease, reducing the severity of a disease symptom, retarding progression of a disease symptom, removing a disease symptom, or delaying onset of a disease and the like.

As used herein, the term "prevention" of a disease or disorder, or a grammatical derivation thereof, is defined as either reducing the risk of onset of a disease, delaying the onset of a disease, or reducing the severity of a disease, or any combination thereof. Preventive therapy is typically administered to a subject who is at increased risk (compared to the general population) of developing a disorder, e.g., an autoimmune disorder, but does not yet meet the criteria for a disease diagnosis. A subject can be characterized as "at risk" of developing a disorder by identifying a DNA variant (including a mutation) associated with the disorder (e.g. an HLA haplotype), according to any suitable method known in the art or described herein. Alternatively, a subject can be characterized as "at risk" of developing a disorder if the subject is positive for any biomarker (e.g. an autoantibody) associated with the future development of the disorder. Additionally or alternatively, a subject can be characterized as "at risk" of developing a disorder if the subject has a family history of the disorder. "Prevention" of an immune response to a therapeutic peptide, protein, viral gene therapy vector, nucleic acid or cell means either blocking, reducing or delaying the immune response to the therapeutic agent, or any combination thereof.

The term "pharmaceutically acceptable" means safe for administration to a mammal, such as a human. In some embodiments, a pharmaceutically acceptable composition is approved by a regulatory agency of the Federal government (e.g. the United States Food and Drug Administration) or a state government or listed in the U. S. Pharmacopeia or other generally recognized pharmacopeia for use in animals, and more particularly in humans.

The term "carrier" refers to a diluent, adjuvant, preservative, or other excipient, or vehicle with which a liposomal composition of the invention is stored and/or administered. Examples of suitable pharmaceutical carriers are described in "Remington's Pharmaceutical Sciences," Mack Publishing Co., Easton, PA., 2nd edition, 2005.

The terms "a" and "an" mean "one or more of." For example, "a gene" is understood to represent one or more such genes. As such, the terms "a" and "an," "one or more of a (or an)," and "at least one of a (or an)" are used interchangeably herein.

As used herein, the term "about" refers to a value within ±10% variability from the reference value, unless otherwise specified.

For any conflict in definitions between various sources or references, the definition provided herein shall control.

Compositions

The invention provides liposomes in the nanometer size range having a lipid composition configured for efficient loading of ITE for tolerization of a subject's immune system, which can carry one or more antigens to which tolerance is to be induced. In some embodiments, the compositions of the present invention enable delivery of less total ITE to a subject relative to that which would be therapeutically effective as delivered by a different means (e.g., as a free drug). In some embodiments, the population of liposomes has an average of 150-15,000 molecules of ITE per liposome (e.g., from 200-12,500 molecules of ITE, from 250-10,000 molecules of ITE, from 300-7,500 molecules of ITE, from 350-5,000 molecules of ITE, from 400-2,500 molecules of ITE, or from 450-1,000 molecules of ITE, e.g., from 100-200 molecules of ITE, from 200-500 molecules of ITE, from 500-1,000 molecules of ITE, from 1,000-2,500 molecules of ITE, from 2,500-5,000 molecules of ITE, from 5,000-7,500 molecules of ITE, from 7,500-10,000 molecules of ITE, or from 10,000-15,000 molecules of ITE).

Liposomes of the invention can be nano-sized liposomes. In particular embodiments, a population of liposomes has an average (e.g., mean or median) diameter from 50 to 500 nm (e.g., from 60 to 250 nm, from 70 to 200 nm, from 80 to 150 nm, from 85 to 125 nm, from 90 to 110 nm, or from 95 to 105 nm, e.g., about 60 nm, about 70 nm, about 80 nm, about 90 nm, about 95 nm, about 100 nm, about 105 nm, about 110 nm, about 120 nm, or about 125 nm).

Tolerogenic liposomes may have a surface charge (i.e., zeta potential) from −10 mv to −50 mv (e.g., from −15 mv to −45 mv, from −20 mv to −40 mv, or from −25 mv to −35 mv, e.g., from −10 mv to −15 mv, from −15 mv to −20 mv, from −20 mv to −25 mv, from −25 mv to −30 mv, from −30 mv to −35 mv, from −35 mv to −40 mv, from −40 mv to −45 mv, or from −45 mv to −50 mv, e.g., about −10 mv, about −15 mv, about −20 mv, about −25 mv, about −30 mv, about −35 mv, about −40 mv, about −45 mv, or about −50 mv). Alternatively, tolerogenic liposomes may have a positive surface charge from +10 mv to +50 mv (e.g., from +15 mv to +45 mv, from +20 mv to +40 mv, or from +25 mv to +35 mv, e.g., from +10 mv to +15 mv, from +15 mv to +20 mv, from +20 mv to +25 mv, from +25 mv to +30 mv, from +30 mv to +35 mv, from +35 mv to +40 mv, from +−40 mv to +45 mv, or from +45 mv to +50 mv, e.g., about +10 mv, about +15 mv, about +20 mv, about +25 mv, about +30 mv, about +35 mv, about +40 mv, about +45 mv, or about +50 mv). Tolerogenic liposomes may also be in the neutral range, with zeta potential between −10 mv to +10 mv.

Lipids

Liposomes of the invention are characterized by lipid compositions that enable efficient loading and delivery of ITE (e.g., to dendritic cells of the immune system). The present inventors have discovered that liposomes made from lipid mixtures having (i) a high fraction of one or more unsaturated (e.g., monounsaturated) fatty acid tails (e.g., wherein one or both tails contain at least one carbon-carbon double bond), and (ii) cholesterol within a narrow concentration range, uniquely provide for therapeutically effective concentrations of ITE within the lipid bilayer, while also compatible with prolonged (e.g. for three months or longer) liposomal stability. Such lipids having unsaturated fatty acid tails include, for example, egg phosphocholine (egg PC), soy phosphocholine (soy PC), 1,2-dioleoyl-sn-glycero-3-phosphocholine (DOPC), 1,2-dioleoyl-sn-glycero-3-phospho-L-serine (DOPS), as well as phospholipids containing, for example, oleic acid, palmitoleic acid, and cis-vaccenic acid. Egg PC has a double bond on one of its two fatty acid tails, whereas DOPC, DOPS, oleic acid, palmitoleic acid, and cis-vaccenic acid each have one double bond on both of its two fatty acid tails. Soy PC has two double bonds on one fatty acid chain. Representative structures of egg PC, DOPC, and DOPS are shown below.

Egg PC

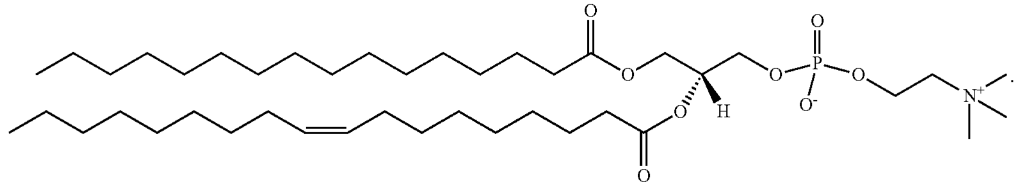

Representative structure only

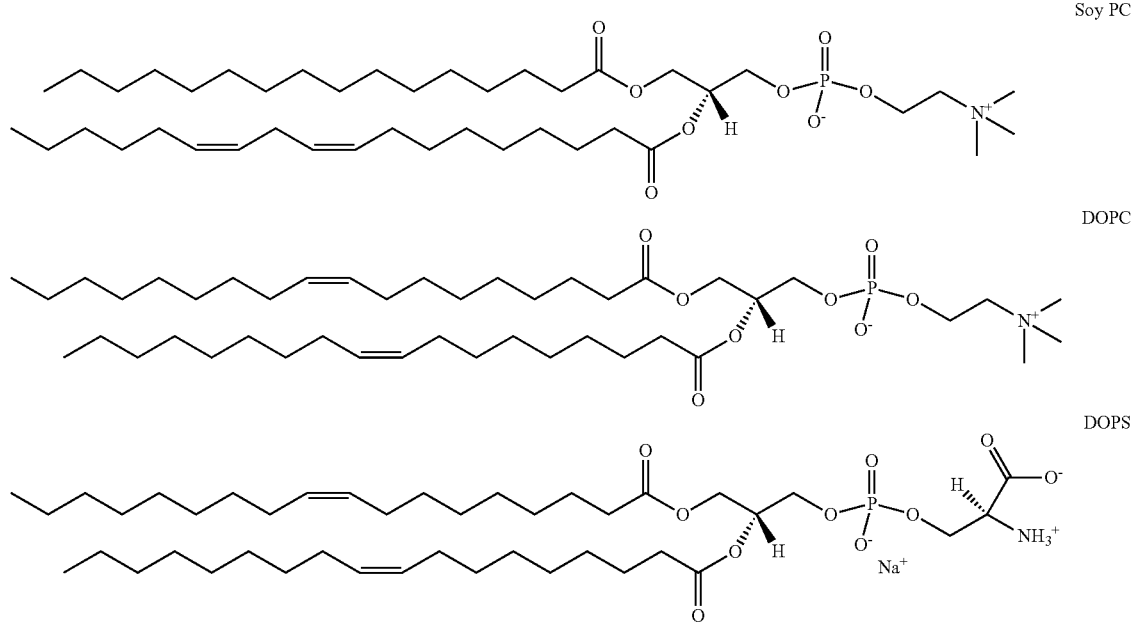

Lipids useful in the synthesis of ITE-loaded tolerogenic liposomes include those having fatty acid tails from 10-25 carbons in length (e.g., from 10-20, from 12-18, or from 14-16 carbons in length, e.g., from 10-12, 12-14, 14-16, 16-18, 18-20, or 20-25 carbons in length, e.g., greater than 10, 11, 12, 13, 14, 15, 16, 17, 18, 19, 20, 21, 22, 23, 24, or 25 carbons in length). In some embodiments, lipids of the present liposomes having one or two fatty acid tails, each greater than 14 carbons in length. In preferred embodiments, at least 50% of the lipid mixture comprises unsaturated lipids (i.e. with at least one carbon-carbon double bond in at least one of its fatty acid tails). Such unsaturated lipids include, for example, egg PC, soy PC, DOPC, and DOPS.

Unsaturated single fatty acid chain phospholipids are also useful for formulating ITE, including, for example, mono-unsaturated lyso-phosphatidylcholine (lyso PC) species such as 1-(10Z-heptadecenoyl)-2-hydroxy-sn-glycero-3-phos-phocholine (17:1 lyso PC) and 1-hydroxy-2-oleoyl-sn-glycero-3-phosphocholine (2-18:1 Lyso PC).

The desaturation index of a liposome is a term used herein to quantify the amount of unsaturated lipids in a lipid mixture, based on all the lipids present, including phospholipids (mono- or di-acyl) and cholesterol or cholesterol alternatives. The desaturation index is based on the fraction of unsaturated bonds present in the mixture, but: (i) weighs the first unsaturated bond more heavily than subsequent unsaturated bonds; (ii) weighs single unsaturated bonds in both fatty acids of the same phospholipid more than two unsaturated bonds in the same fatty acid chain; and (iii) weighs unsaturated bonds in different phospholipids more than in a single phospholipid. The weighting factors for calculating the phospholipid contribution to the desaturation index are summarized in the table below. Phospholipids 1 and 2 refer to two hypothetical diacylphospholipids combined in a 1:1 ratio to make a liposome (ignoring any contribution from cholesterol). FA1 and FA2 refer to the two fatty acyl chains of each phospholipid. A monoacyl phospholipid (e.g. a lyso PC) would be scored with FA2=0. The scoring weights in the table can be extended to other phospholipid compositions.

| Phospholipid 1 | | | Phospholipid 2 | | | desaturation sub-score |
|---|---|---|---|---|---|---|
| FA1 | FA2 | Weights of 1, 2 or 3 C=C bonds in FA1 of PL1 | FA1 | FA2 | Weights of 1, 2 or 3 C=C bonds in FA1 of PL2 | for PL1 and PL2, assuming a 1:1 ratio (no cholesterol) |
| 1 | 0 | 1 | 0 | 0 | 0 | (1 + 0)/2 = 0.5 |
| 2 | 0 | 1 + 0.25 | 0 | 0 | 0 | (1.25 + 0)/2 = 0.625 |
| 3 | 0 | 1 + 0.25 + 0.125 | 0 | 0 | 0 | (1.375 + 0)/2 = 0.6875 |
| 1 | 0 | 1 | 1 | 0 | 0.5 | (1 + .5)/2 = 0.75 |
| 1 | 0 | 1 | 2 | 0 | 0.5 + 0.125 | (1 + 0.625)/2 = 0.8125 |
| 1 | 0 | 1 | 3 | 0 | 0.5 + 0.125 + 0.0625 | (1 + 0.6875)/2 = 0.84375 |
| 1 | 1 | 1 + 0.4 | 0 | 0 | 0 | (1.4 +0)/2 = 0.7 |
| 1 | 2 | 1 + (0.4 + 0.1) | 0 | 0 | 0 | (1.5 +0)/2 = 0.75 |
| 1 | 3 | 1 + (0.4 + 0.1 + 0.05) | 0 | 0 | 0 | (1.55 +0)/2 = 0.775 |

The desaturation index takes into account all lipid components of the lipid mixture used to make liposomes. In preferred embodiments liposomes contain cholesterol, in addition to one or more phospholipids. The table below shows how the desaturation index is computed for several exemplary liposome recipes, all at 30% cholesterol (molar ratio). Weighting factors for unsaturated C=C bonds are shown above. For example, in the first row of the table DSPE has no unsaturated bonds (score: 0), egg PC has a single unsaturated bond in one of two fatty acid chains (score 1×0.5=0.5) and is present at a molar ratio of 65%, while cholesterol counts toward the lipid total but does not contribute to the desaturation index (score: 0). Multiplying 0.5 (egg PC score)×0.65 (egg PC molar ratio)=0.325, which is the desaturation index of the lipid mixture in row 1.

| Phospholipid 1 | | | | Phospholipid 2 | | | | choles- | desaturation index | | |
|---|---|---|---|---|---|---|---|---|---|---|---|
| name | FA 1 | FA 2 | % | name | FA 1 | FA 2 | % | terol % | PL1 | PL 2 | total |
| DSPE | 18:0 | 18:0 | 5 | egg PC | 16:0 | 18:1 | 65 | 30 | 0 | 32.5 | 32.5 |
| DSPE | 18:0 | 18:0 | 5 | soy PC | 16:0 | 18:2 | 65 | 30 | 0 | 40.625 | 40.625 |
| DSPE | 18:0 | 18:0 | 5 | DOPC | 18:1 | 18:1 | 65 | 30 | 0 | 48.75 | 48.75 |

A summary of monounsaturated fatty acids useful as part of the liposomes described herein are summarized below.

| Common name | Structure | Chemical name |
|---|---|---|
| Monounsaturated omega-7 fatty acids | | |
| None | 14:1 (n-7) | 7-Tetradecenoic acid |
| Palmitoleic acid | 16:1 (n-7) | 9-Hexadecenoic acid |
| Vaccenic acid | 18:1 (n-7) | 11-Octadecenoic acid |
| Paullinic acid | 20:1 (n-7) | 13-Eicosenoic acid |
| None | 22:1 (n-7) | 15-Docosenoic acid |
| Monounsaturated omega-9 fatty acids | | |
| Oleic acid | 18:1 (n-9) | (Z)-octadec-9-enoic acid |
| Elaidic acid | 18:1 (n-9) | (E)-octadec-9-enoic acid |
| Gondoic acid | 20:1 (n-9) | (Z)-eicos-11-enoic acid |
| Erucic acid | 22:1 (n-9) | (Z)-docos-13-enoic acid |

Other lipids that may be useful in formulating liposomes of the present invention include 1,2-dimyristoyl-sn-glycero-3-phosphocholine (DMPC); 1,2-distearoyl-sn-glycero-3-phosphocholine (DSPC); 1,2-distearoyl-sn-glycero-3-phosphoethanolamine-N-[methoxy(poly-ethylene glycol)-2000] (PEG2000-DSPE); and D-alpha-tocopherol poly(ethylene glycol)-1000 succinate (TPGS-1000).

The outward-facing phospholipid head group can affect interactions with immune cells. For example, phospholipids which terminate in L-serine (phosphatidylserine species) can induce tolerance in immune cells. This property reflects the natural role of phospho-L-serine phospholipids in apoptosis. Ordinarily phosphatidylserine is located in the inner leaflet (layer) of the cell membrane. However, it appears in the outer leaflet of apoptotic cells or cell fragments, where it induces a tolerogenic response in phagocytic cells. Thus, in certain embodiments, phospholipids terminating in L-serine, such as 1,2-dioleoyl-sn-glycero-3-phospho-L-serine (DOPS), are useful components of tolerogenic liposomes.

Certain lyso-phospholipids (lyso PLs, e.g., lyso phosphatidylcholine, or lyso PC), can provide tolerogenic signals to DCs (Kabarowski et al., *Biochem. Pharmacol.* 2002, 64: 161-167; Peter et al., *J. Biol. Chem.* 2008, 283: 5296-5305, each of which is herein incorporated by reference in its entirety). Thus, in certain embodiments, lyso PLs are also useful in formulating tolerogenic liposomes, particularly lyso PLs with unsaturated side chains.

One or more unsaturated (e.g., monounsaturated) lipid species may account for at least 50% of the total lipids (on a molar basis). In some embodiments, the unsaturated (e.g., monounsaturated) lipid species may account for at least 55%, at least 60%, at least 65%, at least 70%, or at least 75% of the total lipids of the liposome (e.g., from 50% to 60%, from 60% to 65%, from 65% to 70%, from 70% to 75%, or from 75% to 80%, e.g., about 50%, about 55%, about 60%, about 65%, about 70%, about 75%, or about 80% of the total lipids of the liposome). In some embodiments, an unsaturated lipid species accounts for at least 25% of the total lipids.

The desaturation index is an alternative measure of the extent of unsaturated bonds in a lipid mixture. In some embodiments, the population of liposomes has an average desaturation index of 0.3 or greater (e.g., at least 0.3, at least 0.35, at least 0.4, at least 0.45, at least 0.5, at least 0.55, at least 0.6, or at least 0.65, e.g., from 0.3 to 0.4, from 0.4 to 0.5, from 0.5 to 0.6, from 0.6 to 0.7, e.g., about 0.3, about 0.35, about 0.4, about 0.45, about 0.5, about 0.55, about 0.6, or about 0.65.

Additionally or alternatively, the liposomes can have a lipid composition characterized by a particular phase-transition temperature amenable for loading and delivery of ITE, and for long-term stability of ITE-loaded liposomes. In some embodiments, the average phase transition temperature of a lipid composition of a population of liposomes is from 0° C. to 70° C. (e.g., from 0° C. to 5° C., from 5° C. to –10° C., from 10° C. to 20° C., from 20° C. to 30° C., from 30° C. to 40° C., from 40° C. to 50° C., from 50° C. to 60° C., or from 60° C. to 65° C., e.g., about 0° C., about 5° C., about 10° C., about 20° C., about 30° C., about 40° C., about 50° C., about 60° C., about 65° C., or about 70° C.).

Tolerogenic liposomes can be made using any suitable method known in the art or described herein. In some embodiments, ITE is loaded into liposomes by micelle transfer (e.g., as described in Example 2). In other embodiments, ITE is formulated in liposomes by ethanol injection (e.g., as described in Example 3). For example, lipids can be combined in the desired ratio and dissolved in ethanol prior to addition of ITE in DMSO. The volume of added ITE, in some embodiments, does not exceed 10% (e.g., does not exceed 9%, 8%, 7%, 6%, or 5%) of the volume of lipid/ethanol solution. ITE is able to dissolve into the lipid mixture in 10-30 minutes by heating at 35-65° C. (temperature selected based on the lipid mixture) with agitation. The resulting lipid/ITE/ethanol solution can then be transferred into a pre-warmed HBS solution containing antigen (e.g., at a concentration from 0.001 to 10 mg/mL, e.g., from 0.005 to 5 mg/mL, e.g., about 0.05 mg/mL, 0.10 mg/mL, 0.15 mg/mL, 0.20 mg/mL, 0.25 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 2.0 mg/mL, 3.0 mg/mL, 4.0 mg/mL, 5.0 mg/mL, 6.0 mg/mL, 7.0 mg/mL, 8.0 mg/mL, 9.0 mg/mL, or 10 mg/mL). After stirring at 35-65° C. (based on lipid mixture) while allowing liposomes to form around (i.e. encapsulating) the aqueous antigen solution, the mixture is passed through a series of polycarbonate membranes using conventional extrusion techniques to convert multi-lamellar membranes into unilamellar liposomes of defined size (based on the pore size of the membranes) and uniform size distribution. Passing the liposomes successively through multiple 200 nm- and/or 100 nm-pore size membranes can yield nanoparticulate liposomes having a narrow distribution (polydispersity index <0.05) around 90-110 nm in diameter. Soluble antigen residing outside of the liposome core can be washed out of the liposome suspension by any suitable method (e.g., filtration, dialysis, or centrifugation).

Antigens for Autoimmune Diseases

In some embodiments, the liposomes provided herein include an antigen co-formulated with ITE (e.g., within the aqueous core of the liposome) to focus tolerization on one or a few specific antigens. Antigens that elicit disease-causing or otherwise undesirable immune responses consist of peptides or proteins (including post-translational modifications), lipids, viral gene therapy vectors and nucleic acids. One or more antigens can be co-formulated with ITE in a liposome, or alternatively, if two antigens are chemically incompatible, two or more populations of liposomes can be produced, each with at least one antigen, and all with ITE.

Rheumatoid Arthritis Antigens

Liposomes may include any antigen associated with the pathogenic immune response which the composition is configured to treat. For example, proteins which initiate autoimmune T and B cell reactions in rheumatoid arthritis patients include vimentin (including mutated vimentin), fibrinogen, alpha enolase, and collagen, any of which may be contain post-translationally created citrulline in place of arginine or lysine. Immune responses are frequently directed against post-translationally modified variants of these proteins. These most common protein modifications result from the enzymatic deimination of arginine (by peptidylarginine deiminases) to the non-standard amino acid citrulline, or the carbamylation of lysine. The use of citrullinated peptides for diagnosis of rheumatoid arthritis is well known. For example WO 2007/123976 discloses vimentin peptides, including citrullinated peptides, for diagnosis of rheumatoid arthritis, WO 2007/017556, discloses collagen type II peptides, including citrullinated peptides, for diagnosis of rheumatoid arthritis, and WO 2008/090360 discloses the use of enolase peptides, including citrullinated peptides, for diagnosis of rheumatoid arthritis. Rheumatoid arthritis-associated antigens that may be used as antigens of the present invention include the proteins aggrecan, alpha enolase, collagen type II, beta fibrinogen, filaggrin and vimentin. As an alternative to formulating these proteins immunogenic peptides identified as the target of T cell responses can be formulated in tolerogenic liposomes. Relevant peptide sequences are provided in the literature (e.g. U.S. Patent Publication No. 2016/0024183. Each of the aforementioned publications are incorporated herein by reference in their entirety.

Specific rheumatoid arthritis peptides disclosed in US 2016/0024183 include the citrullinated beta fibrinogen peptide CitPAPPPISGGGYCitACit (SEQ ID NO: 1), the citrullinated collagen type II peptide ACitGLTGCitPGDAK (SEQ ID NO: 2), the citrullinated filaggrin peptide HQCHQESTCitGRSRGRCGRSGS (SEQ ID NO: 3), the citrullinated vimentin peptide SAVRACitSSVPGVRK (SEQ ID NO: 4) and fragments and combinations thereof.

Type 1 Diabetes Antigens

Antigens associated with type 1 diabetes and latent autoimmune diabetes of adults (LADA), include the proteins preproinsulin and its processed forms proinsulin and insulin; glutamic decarboxylase 65 and 67 (GAD65 and GAD67); imogen-38; islet-specific glucose-6-phosphatase catalytic subunit-related protein (IGRP); tyrosine phosphatase like autoantigen or insulinoma antigen-2 (synonyms: IA-2; ICA512, PTPRN); IA-2β (synonyms: Phogrin, ICA512, PTPRN2); islet cell antigen-69 (ICA69); carboxypeptidase H; zinc transporter 8 (ZnT8); chromogranin A.

In addition to, or as an alternative to the proteins listed above, some of which may be difficult to express in recombinant systems, or to formulate in liposomes, peptides can be used in tolerizing liposomes for the treatment of type 1 diabetes and LADA.

Useful preproinsulin peptides are disclosed in U.S. Pat. No. 6,562,943 and include QPLALEGSLQK (SEQ ID NO: 5), as well as peptides overlapping that sequence, e.g., GGGPGAGSLQPLALEGSLQK (SEQ ID NO: 6), GSLQPLALEGSLQKRGIV (SEQ ID NO: 7), known as C19-A3, or QPLALEGSLQKRGIVEQ (SEQ ID NO: 8).

Additional preproinsulin peptides are disclosed in U.S. 2007/129307 and include ALWMRLLPL (SEQ ID NO: 9); HLVEALYLV (SEQ ID NO: 10); SHLVEALYLVCGERG (SEQ ID NO: 11), known as B9-23; or DLQVGQVEL (SEQ ID NO: 12).

Useful IA-2 peptides are disclosed in U.S. Pat. No. 6,562,943 and include VSSQFSDAAQASP (SEQ ID NO: 13), as well as peptides containing VSSQFSDAAQASP (SEQ ID NO: 13) flanked by up to five N-terminal amino acids and/or up to eleven C-terminal amino acids, e.g., SRVSSVSSQFSDAAQASPSSHSST (SEQ ID NO: 14); SSVSSQFSDAAQASP (SEQ ID NO: 15); SVSSQFSDAAQASPS (SEQ ID NO: 16); SVSSQFSDAAQASPSSHSS (SEQ ID NO: 17); SVSSQFSDAAQASPSSHSSTPSWC (SEQ ID NO: 18); VSSQFSDAAQASPSS (SEQ ID NO: 19); VSSVSSQFSDAAQASPSSHSS (SEQ ID NO: 20); VSSQFSDAAQASPSSHSSTPSWCE (SEQ ID NO: 21).

The IA-2 peptide can alternatively be TQETRTL (SEQ ID NO: 22), or TQETRTL (SEQ ID NO: 22) flanked by up to eight N-terminal amino acids and/or up to five C-terminal amino acids, e.g., SFYLKNVQTQETRTLTQFH (SEQ ID NO: 23); FYLKNVQTQETRTLTQFHF (SEQ ID NO: 24); YLKNVQTQETRTL (SEQ ID NO: 25); YLKNVQTQETRTLTQ (SEQ ID NO: 26); LKNVQTQETRTLTQF (SEQ ID NO: 27); KNVQTQETRTLTQFH (SEQ ID NO:28); VQTQETRTLTQFHF (SEQ ID NO: 29); or TQETRTLTQFHF (SEQ ID NO: 30).

The IA-2 peptide can alternatively be AYQAEPNT (SEQ ID NO: 31), or AYQAEPNT (SEQ ID NO: 31) flanked by up to nine N-terminal amino acids and/or up to eleven C-terminal amino acids, e.g., LAKEWQALCAYQAEPNT (SEQ ID NO: 32); LAKEWQALCAYQAEPNTCATAQGE (SEQ ID NO: 33); WQALCAYQAEPNTCATAQ (SEQ ID NO: 34); LCAYQAEPNTCATAQG (SEQ ID NO: 35); AYQAEPNTCATAQ (SEQ ID NO: 36); or AYQAEPNTCATAQGEGNIK (SEQ ID NO: 37).

The IA-2 peptide can alternatively be CTVIVMLT (SEQ ID NO: 38), or CTVIVMLT (SEQ ID NO: 38) flanked by up to ten N-terminal amino acids and/or up to eight C-terminal amino acids, e.g., DFWQMVWESGCTVIVMLT (SEQ ID NO: 39); FWQMVWESGCTVIVMLTPLV (SEQ ID NO: 40); WQMVWESGCTVIVMLT (SEQ ID NO: 41); MVWESGCTVIVMLTPL (SEQ ID NO: 42); MVWESGCTVIVMLTPLVEDGV (SEQ ID NO: 43); ESGCTVIVMLTPLVEDG (SEQ ID NO: 44); ESGCTVIVMLTPLVEDGV (SEQ ID NO: 45); SGCTVIVMLTPLVEDGVK (SEQ ID NO: 46); GCTVIVMLTPLVED (SEQ ID NO: 47); or CTVIVMLTPLVEDG (SEQ ID NO: 48).

The IA-2 peptide can alternatively be FEFALTAVAEE (SEQ ID NO: 49), or FEFALTAVAEE (SEQ ID NO: 49) flanked by up to four N-terminal amino acids and/or up to seven C-terminal amino acids, e.g. SKDQFEFALTA-VAEEVNA (SEQ ID NO: 50); SKDQFEFALTA-VAEEVNAILK (SEQ ID NO: 51); DQFEFALTAVAEE (SEQ ID NO: 52); DQFEFALTAVAEEVNAI (SEQ ID NO: 53); or FEFALTAVAEEVNAILKA (SEQ ID NO: 54).

The IA-2 peptide can alternatively be KVESSPSRSDY (SEQ ID NO: 55), or KVESSPSRSDY (SEQ ID NO: 55) flanked by up to two N-terminal amino acids and/or up to eleven C-terminal amino acids, e.g., KLKVESSPSRSDYI-NAS (SEQ ID NO: 56); KLKVESSPSRSDYINAS-PIIEHDP (SEQ ID NO: 57); LKVESSPSRSDY (SEQ ID NO: 58); LKVESSPSRSDYINASPII (SEQ ID NO: 59); KVESSPSRSDYI (SEQ ID NO: 60); and KVESSPSRSDYINASPIIEHDP (SEQ ID NO: 61).

The IA-2 peptide can alternatively be one of the peptides disclosed in U.S. 2007/0129307A1, including SLSPLQAEL (SEQ ID NO: 62); LLPPLLEHL (SEQ ID NO: 63); GLLY-LAQEL (SEQ ID NO: 64); VLAGYGVEL (SEQ ID NO: 65); TLLTLLQLL (SEQ ID NO: 66); SLAAGVKLL (SEQ ID NO: 67); or VLLTLVALA (SEQ ID NO: 68).

The peptide can also be a phogrin peptide, an IGRP peptide, an IAPP peptide, a GAD65 peptide, or a chromogranin A peptide. Useful phogrin peptides are disclosed in U.S. 2007/0129307A1 and include LLLLLLLL (SEQ ID NO: 69); LLLLLPPRV (SEQ ID NO: 70); GMAELMAGL (SEQ ID NO: 71); LMAGLMQGV (SEQ ID NO: 72); RLYQEVHRL (SEQ ID NO: 73), and SLLDFRRKV (SEQ ID NO: 74). Useful IGRP peptides are disclosed in U.S. 2007/0129307A1 and include FLWSVFMLI (SEQ ID NO: 75); FLFAVGFY (SEQ ID NO: 76); and RLLCALTSL (SEQ ID NO: 77). Useful IAPP peptides are disclosed in U.S. 2007/0129307A1 and include KLQVFLIVL (SEQ ID NO: 78) and FLIVLSVAL (SEQ ID NO: 79). A useful GAD65 peptide is disclosed in WO2016162495: TVYGAFDPLLA-VAD (SEQ ID NO: 80), as well as the chromogranin A peptide WSKMDQLAKELTAE (SEQ ID NO: 81), known as WE-14.

Each of the aforementioned publications are hereby incorporated by reference in their entireties.

Antigens can also be proteins containing polypeptides at least 80%, 85%, 90%, 95%, 96%, 97%, 98% or 99% identical to any of the above antigens, or fragments thereof.

The above antigens (also listed in the table below) can be co-formulated with ITE in liposomes and used to treat patients at high risk of developing, or with the recent onset of, type 1 diabetes, or with LADA.

| Peptide | Sequence | SEQ ID NO: |
|---|---|---|
| citrullinated beta fibrinogen peptide | CitPAPPPISGGGYCitACit | SEQ ID NO: 1 |
| citrullinated collagen type II peptide | ACitGLTGCitPGDAK | SEQ ID NO: 2 |
| citrullinated filaggrin peptide | HQCHQESTCitGRSRGRCGRSGS | SEQ ID NO: 3 |
| citrullinated vimentin peptide | SAVRACitSSVPGVRK | SEQ ID NO: 4 |
| preproinsulin peptide | QPLALEGSLQK | SEQ ID NO: 5 |
| preproinsulin peptide | GGGPGAGSLQPLALEGSLQK | SEQ ID NO: 6 |
| preproinsulin peptide | GSLQPLALEGSLQKRGIV | SEQ ID NO: 7 |
| preproinsulin peptide | QPLALEGSLQKRGIVEQ | SEQ ID NO: 8 |
| preproinsulin peptide | ALWMRLLPL | SEQ ID NO: 9 |
| preproinsulin peptide | HLVEALYLV | SEQ ID NO: 10 |
| preproinsulin peptide | SHLVEALYLVCGERG | SEQ ID NO: 11 |
| preproinsulin peptide | DLQVGQVEL | SEQ ID NO: 12 |
| IA-2 peptide | VSSQFSDAAQASP | SEQ ID NO: 13 |
| IA-2 peptide | SRVSSVSSQFSDAAQASPSSHSST | SEQ ID NO: 14 |
| IA-2 peptide | SSVSSQFSDAAQASP | SEQ ID NO: 15 |
| IA-2 peptide | SVSSQFSDAAQASPS | SEQ ID NO: 16 |
| IA-2 peptide | SVSSQFSDAAQASPSSHSS | SEQ ID NO: 17 |
| IA-2 peptide | SVSSQFSDAAQASPSSHSSTPSWC | SEQ ID NO: 18 |
| IA-2 peptide | VSSQFSDAAQASPSS | SEQ ID NO: 19 |
| IA-2 peptide | VSSVSSQFSDAAQASPSSHSS | SEQ ID NO: 20 |
| IA-2 peptide | VSSQFSDAAQASPSSHSSTPSWCE | SEQ ID NO: 21 |
| IA-2 peptide | TQETRTL | SEQ ID NO: 22 |
| IA-2 peptide | SFYLKNVQTQETRTLTQFH | SEQ ID NO: 23 |

-continued

| Peptide | Sequence | SEQ ID NO: |
|---|---|---|
| IA-2 peptide | FYLKNVQTQETRTLTQFHF | SEQ ID NO: 24 |
| IA-2 peptide | YLKNVQTQETRTL | SEQ ID NO: 25 |
| IA-2 peptide | YLKNVQTQETRTLTQ | SEQ ID NO: 26 |
| IA-2 peptide | LKNVQTQETRTLTQF | SEQ ID NO: 27 |
| IA-2 peptide | KNVQTQETRTLTQFH | SEQ ID NO: 28 |
| IA-2 peptide | VQTQETRTLTQFHF | SEQ ID NO: 29 |
| IA-2 peptide | TQETRTLTQFHF | SEQ ID NO: 30 |
| IA-2 peptide | AYQAEPNT | SEQ ID NO: 31 |
| IA-2 peptide | LAKEWQALCAYQAEPNT | SEQ ID NO: 32 |
| IA-2 peptide | LAKEWQALCAYQAEPNTCATAQGE | SEQ ID NO: 33 |
| IA-2 peptide | WQALCAYQAEPNTCATAQ | SEQ ID NO: 34 |
| IA-2 peptide | LCAYQAEPNTCATAQG | SEQ ID NO: 35 |
| IA-2 peptide | AYQAEPNTCATAQ | SEQ ID NO: 36 |
| IA-2 peptide | AYQAEPNTCATAQGEGNIK | SEQ ID NO: 37 |
| IA-2 peptide | CTVIVMLT | SEQ ID NO: 38 |
| IA-2 peptide | DFWQMVWESGCTVIVMLT | SEQ ID NO: 39 |
| IA-2 peptide | FWQMVWESGCTVIVMLTPLV | SEQ ID NO: 40 |
| IA-2 peptide | WQMVWESGCTVIVMLT | SEQ ID NO: 41 |
| IA-2 peptide | MVWESGCTVIVMLTPL | SEQ ID NO: 42 |
| IA-2 peptide | MVWESGCTVIVMLTPLVEDGV | SEQ ID NO: 43 |
| IA-2 peptide | ESGCTVIVMLTPLVEDG | SEQ ID NO: 44 |
| IA-2 peptide | ESGCTVIVMLTPLVEDGV | SEQ ID NO: 45 |
| IA-2 peptide | SGCTVIVMLTPLVEDGVK | SEQ ID NO: 46 |
| IA-2 peptide | GCTVIVMLTPLVED | SEQ ID NO: 47 |
| IA-2 peptide | CTVIVMLTPLVEDG | SEQ ID NO: 48 |
| IA-2 peptide | FEFALTAVAEE | SEQ ID NO: 49 |
| IA-2 peptide | SKDQFEFALTAVAEEVNA | SEQ ID NO: 50 |
| IA-2 peptide | SKDQFEFALTAVAEEVNAILK | SEQ ID NO: 51 |
| IA-2 peptide | DQFEFALTAVAEE | SEQ ID NO: 52 |
| IA-2 peptide | DQFEFALTAVAEEVNAI | SEQ ID NO: 53 |
| IA-2 peptide | FEFALTAVAEEVNAILKA | SEQ ID NO: 54 |
| IA-2 peptide | KVESSPSRSDY | SEQ ID NO: 55 |
| IA-2 peptide | KLKVESSPSRSDYINAS | SEQ ID NO: 56 |
| IA-2 peptide | KLKVESSPSRSDYINASPIIEHDP | SEQ ID NO: 57 |
| IA-2 peptide | LKVESSPSRSDY | SEQ ID NO: 58 |
| IA-2 peptide | LKVESSPSRSDYINASPII | SEQ ID NO: 59 |
| IA-2 peptide | KVESSPSRSDYI | SEQ ID NO: 60 |
| IA-2 peptide | KVESSPSRSDYINASPIIEHDP | SEQ ID NO: 61 |

-continued

| Peptide | Sequence | SEQ ID NO: |
|---|---|---|
| IA-2 peptide | SLSPLQAEL | SEQ ID NO: 62 |
| IA-2 peptide | LLPPLLEHL | SEQ ID NO: 63 |
| IA-2 peptide | GLLYLAQEL | SEQ ID NO: 64 |
| IA-2 peptide | VLAGYGVEL | SEQ ID NO: 65 |
| IA-2 peptide | TLLTLLQLL | SEQ ID NO: 66 |
| IA-2 peptide | SLAAGVKLL | SEQ ID NO: 67 |
| IA-2 peptide | VLLTLVALA | SEQ ID NO: 68 |
| phogrin peptide | LLLLLLLLL | SEQ ID NO: 69 |
| phogrin peptide | LLLLLPPRV | SEQ ID NO: 70 |
| phogrin peptide | GMAELMAGL | SEQ ID NO: 71 |
| phogrin peptide | LMAGLMQGV | SEQ ID NO: 72 |
| phogrin peptide | RLYQEVHRL | SEQ ID NO: 73 |
| phogrin peptide | SLLDFRRKV | SEQ ID NO: 74 |
| IGRP peptide | FLWSVFMLI | SEQ ID NO: 75 |
| IGRP peptide | FLFAVGFY | SEQ ID NO: 76 |
| IGRP peptide | RLLCALTSL | SEQ ID NO: 77 |
| IAPP peptide | KLQVFLIVL | SEQ ID NO: 78 |
| IAPP peptide | FLIVLSVAL | SEQ ID NO: 79 |
| GAD65 peptide | TVYGAFDPLLAVAD | SEQ ID NO: 80 |
| chromogranin A peptide | WSKMDQLAKELTAE | SEQ ID NO: 81 |

Antigens for Tolerizing to Peptide, Protein, and Gene Therapies

In some embodiments, the compositions and methods described herein feature liposomes that include (e.g., encapsulate) an antigen (e.g., an antigen associated with a therapeutic agent, such as a therapeutic protein, viral vector or nanoparticle). Such embodiments can be used, e.g., to tolerize a subject to an antigen to which the subject may otherwise develop an adverse immune response.

In some embodiments, the antigen encapsulated in the liposomes featured herein is a neoantigen. In some embodiments, the immunity to the neoantigen may pre-date therapeutic exposure. For example, adenoviruses, adeno-associated viruses (AAVs) and herpes viruses are ubiquitous. Thus when these viruses, or modified versions thereof, are used as gene therapy vectors, they may encounter pre-existing immunity, which can interfere with viral transduction. Also, re-exposure to the virus (in the form of gene therapy) often elicits a more robust immune response.

In some embodiments, the neoantigens can be a derived from any portion of a therapeutic agent (e.g., any portion of a peptide, protein, gene therapy or nanoparticle). When the specific structure (e.g., peptide sequence) of a neoantigen is not fully defined, a larger fragment of the therapeutic agent may be formulated in the liposome to provide the neoantigen. Alternatively, the entire therapeutic peptide, protein, viral coat protein or virus may be encapsulated in the liposome.

In some embodiments, diseases or disorders that can be treated by a therapeutic agent described herein (e.g., a therapeutic agent comprising an antigen encapsulated in a liposome of the present invention, which also carries ITE) may include, but are not limited to, autoimmune diseases, allergic diseases (e.g., allergies to environmental agents such as animal dander, pollen, dust mites, insect bites, and so forth, as well as food allergies to nuts, egg products, seafood, grains and so forth), hereditary diseases (treated by protein replacement therapy or gene therapy), organ transplantation (associated with immune rejection, or, in the case of bone marrow transplantation, with graft versus host disease), and a wide variety of other diseases treated by peptide or protein therapeutics (e.g., diabetes).

In some embodiments, autoimmune diseases that can be treated by a therapeutic agent (e.g., a therapeutic agent comprising an antigen encapsulated in a liposome of the present invention, which also carries ITE), the compositions (e.g., liposomal composition of the present invention) or methods described herein include, but are not limited to, diseases that affect the joints and connective tissues (e.g., ankylosing spondylitis, rheumatoid arthritis, juvenile idiopathic arthritis, psoriatic arthritis and mixed connective tissue disease), as well as diseases that affect the brain (e.g., multiple sclerosis and neuromyelitis optica), diseases that affect endocrine organs (e.g., type I diabetes, latent autoimmune diabetes in adults (LADA), autoimmune thyroid disease, Grave's disease, Hashimoto's thyroiditis and Addison's disease), diseases that affect the gastrointestinal tract (e.g., autoimmune atrophic gastritis, pernicious anemia, celiac disease, and inflammatory bowel disease (including Crohn's disease and ulcerative colitis)), diseases that affect the skin (e.g., psoriasis, scleroderma, alopecia areata, atopic dermatitis, pemphigus vulgaris and bullous pemphigoid), diseases that affect the muscle (e.g., myasthenia gravis, Guillain-Barre syndrome and poly/dermatomyositis), diseases that affect the heart (e.g., rheumatic fever), diseases that affect the liver (e.g., autoimmune hepatitis and primary sclerosing cholangitis), diseases that affect the sensory organs (e.g., autoimmune uveitis and Behcet's disease), diseases that affect the blood or bone marrow (e.g., autoimmune haemolytic anemia, idiopathic thrombocylopenic purpura and idiopathic leucopenia), diseases that affect the lungs (e.g., Goodpasture's syndrome), diseases that affect the kidney (e.g., autoimmune nephritis, including glomerulonephritis), diseases that affect the vasculature (e.g., Wegener's granulomatosis), diseases that affect the peripheral nervous system (e.g., chronic inflammatory demyelinating polyradiculoneuropathy), and diseases characterized by multi-organ involvement (e.g., systemic lupus erythematosus and Sjogren's syndrome).

Diseases for Treatment by Gene Therapy

In some embodiments, diseases or disorders that may be treated by gene therapy (e.g., by administration of a viral gene therapy vector), and therefore may benefit from pre-treatment or concurrent treatment, or post therapy treatment with a tolerizing liposomal composition comprising ITE and an antigen include, but are not limited to, lysosomal storage diseases/disorders, such as Santavuori-Haltia disease (Infantile Neuronal Ceroid Lipofuscinosis Type 1), Jansky-Bielschowsky Disease (late infantile neuronal ceroid lipofuscinosis, Type 2), Batten disease (juvenile neuronal ceroid lipofuscinosis, Type 3), Kufs disease (neuronal ceroid lipofuscinosis, Type 4), Von Gierke disease (glycogen storage disease, Type Ia), glycogen storage disease, Type Ib, Pompe disease (glycogen storage disease, Type II), Forbes or Cori disease (glycogen storage disease, Type III), mucolipidosis II (I-Cell disease), mucolipidosis III (Pseudo-Hurler polydystrophy), mucolipidosis IV (sialolipidosis), cystinosis (adult nonnephropathic type), cystinosis (infantile nephropathic type), cystinosis (juvenile or adolescent nephropathic), Salla disease/infantile sialic acid storage disorder, and saposin deficiencies; disorders of lipid and sphingolipid degradation, such as GM1 gangliosidosis (infantile, late infantile/juvenile, and adult/chronic), Tay-Sachs disease, Sandhoff disease, GM2 gangliodisosis, Ab variant, Fabry disease, Gaucher disease, Types I, II and III, metachromatic leukidystrophy, Krabbe disease (early and late onset), Neimann-Pick disease, Types A, B, C1, and C2, Farber disease, and Wolman disease (cholesteryl esther storage disease); disorders of mucopolysaccharide degradation, such as Hurler syndrome (MPSI), Scheie syndrome (MPS IS), Hurler-Scheie syndrome (MPS IH/S), Hunter syndrome (MPS II), Sanfillippo A syndrome (MPS IIIA), Sanfillippo B syndrome (MPS IIIB), Sanfillippo C syndrome (MPS IIIC), Sanfillippo D syndrome (MPS IIID), Morquio A syndrome (MPS IVA), Morquio B syndrome (MPS IVB), Maroteaux-Lamy syndrome (MPS VI), and Sly syndrome (MPS VII); disorders of glycoprotein degradation, such as alpha mannosidosis, beta mannosidosis, fucosidosis, asparylglucosaminuria, mucolipidosis I (sialidosis), galactosialidosis, Schindler disease, and Schindler disease, Type II/Kanzaki disease; and leukodystrophy diseases/disorders, such as abetalipoproteinemia, neonatal adrenoleukodystrophy, Canavan disease, cerebrotendinous xanthromatosis, Pelizaeus Merzbacher disease, Tangier disease, Refum disease (infantile and classic forms), acid maltase deficiency (e.g., Pompe disease, glycogenosis type 2, lysosomal storage disease), carnitine deficiency, camitine palmityl transferase deficiency, debrancher enzyme deficiency (e.g., Cori or Forbes disease, glycogenosis type 3), lactate dehydrogenase deficiency (e.g., glycogenosis type 11), myoadenylate deaminase deficiency, phosphofructokinase deficiency (e.g., Tarui disease, glycogenosis type 7), phosphogylcerate kinase deficiency (e.g., glycogenosis type 9), phosphogylcerate mutase deficiency (e.g., glycogenosis type 10), phosphorylase deficiency (e.g., McArdle disease, myophosphorylase deficiency, glycogenosis type 5), Gaucher's Disease (e.g., chromosome 1, enzyme glucocerebrosidase affected), Achondroplasia (e.g., chromosome 4, fibroblast growth factor receptor 3 affected), Huntington's Disease (e.g., chromosome 4, huntingtin), Hemochromatosis (e.g., chromosome 6, HFE protein), Cystic Fibrosis (e.g., chromosome 7, CFTR), Friedreich's Ataxia (chromosome 9, frataxin), Best Disease (chromosome 11, VMD2), Sickle Cell Disease (chromosome 11, hemoglobin), Phenylketoniuria (chromosome 12, phenylalanine hydroxylase), Marfan's Syndrome (chromosome 15, fibrillin), Myotonic Dystophy (chromosome 19, dystophia myotonica protein kinase), Adrenoleukodystrophy (x-chromosome, lignoceroyl-CoA ligase in peroxisomes), Duchene's Muscular Dystrophy (x-chromosome, dystrophin), Rett Syndrome (x-chromosome, methylCpG-binding protein 2), Leber's Hereditary Optic Neuropathy (mitochondria, respiratory proteins), Mitochondria Encephalopathy, Lactic Acidosis and Stroke (MELAS) (mitochondria, transfer RNA), enzyme deficiencies of the Urea Cycle, Sickle Cell Anemia, Myotubular Myopathy, Hemophilia B, Lipoprotein lipase deficiency, Omithine Transcarbamylase Deficiency, Crigler-Najjar Syndrome, Mucolipidosis IV, Niemann-Pick A, San-filippo A, Sanfilippo B, Sanfilippo C, Sanfilippo D, beta-thalassaemia, Duchenne Muscular Dystrophy, and diseases or disorders that are the result of defects in lipid and sphingolipid degradation, muco-polysaccharide degradation, glycoprotein degradation, leukodystrophies, etc.

Viral Vectors

Liposomes provided by the present invention can include (e.g., encapsulate) one or more viruses (e.g., viral vectors), or portion(s) thereof, such as capsid proteins or immunogenic peptide fragments of capsid proteins. Examples of viral vectors that may be used (e.g., in therapeutic agents to which methods of the invention provide tolerance in a subject) are known in the art and/or described herein. Suitable viral vectors include, for instance, retroviral vectors, lentiviral vectors, herpes simplex virus (HSV)-based vectors, adenovirus-based vectors, adeno-associated virus (AAV)-based vectors, AAV-adenoviral chimeric vectors, vaccinia virus-based vectors and Sendai virus-based vectors.

In some embodiments, the viral vector described herein may be based on a retrovirus. Retroviruses (e.g., viruses belonging to the family Retroviridae) have a single-stranded positive sense RNA genome and are capable of infecting a wide variety of host cells. Upon infection, the retroviral genome integrates into the genome of its host cell, using its own reverse transcriptase enzyme to produce DNA from its RNA genome. The viral DNA is then replicated along with host cell DNA, which translates and transcribes the viral and host genes. A retroviral vector can be manipulated to render the virus replication incompetent. As such, retroviral vectors are thought to be particularly useful for stable gene transfer in vivo. Examples of retroviral vectors useful in the present invention can be found, for example, in U.S. Publication Nos. 20120009161, 20090118212, and 20090017543, the viral vectors and methods of their making being incorporated by reference herein in their entirety.

Lentiviral vectors are examples of retroviral vectors that can be used for the production of a viral vector as provided herein. Lentiviruses have the ability to infect non dividing cells, a property that constitute a more efficient method of a gene delivery vector (see, e.g., Durand et al., Viruses. 2011 February; 3(2): 132-159). Examples of lentiviruses include HIV (humans), simian immunodeficiency virus (SIV), feline immunodeficiency virus (FIV), equine infectious anemia virus (EIAV) and visna virus (ovine lentivirus). Unlike other retroviruses, HIV-based vectors are known to incorporate their passenger genes into non-dividing cells. Examples of lentiviral vectors useful in the present invention can be found, for example, in U.S. Publication Nos. 20150224209, 20150203870, 20140335607, 20140248306, 20090148936, and 20080254008, the viral vectors and methods of their making being incorporated by reference herein in their entirety.

In some embodiments, Herpes simplex virus (HSV)-based viral vectors are suitable for use as provided herein. Many replication deficient HSV vectors contain a deletion to remove one or more intermediate-early genes to prevent replication. Advantages of the herpes vector are its ability to enter a latent stage that can result in long-term DNA expression, and its large viral DNA genome that can accommodate exogenous DNA up to 25 kb. For a description of HSV-based vectors useful in the present invention, see, for example, U.S. Pat. Nos. 5,837,532, 5,846,782, 5,849,572, and 5,804,413, and International Patent Applications WO 91/02788, WO 96/04394, WO 98/15637, and WO 99/06583, the description of which viral vectors and methods of their making being incorporated by reference in its entirety.

In some embodiments, the viral vector described herein may be based on Adenoviruses (Ads). Adenoviruses are non-enveloped viruses that can transfer DNA in vivo to a variety of different target cell types. The virus can be made replication-deficient by deleting select genes required for viral replication. The expendable non-replication-essential E3 region is also frequently deleted to allow additional room for a larger DNA insert. Adenoviral vectors can be produced in high titers and can efficiently transfer DNA to replicating and non-replicating cells. Unlike lentivirus, adenoviral DNA does not integrate into the genome and therefore is not replicated during cell division, instead they replicate in the nucleus of the host cell using the host's replication machinery.

The adenovirus on which a viral vector featured herein may be based, may be from any origin, any subgroup, any subtype, mixture of subtypes, or any serotype. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. Adenoviral serotypes 1 through 51 are available from the American Type Culture Collection (ATCC, Manassas, VA). Non-group C adenoviruses, and even non-human adenoviruses, can be used to prepare replication deficient adenoviral vectors. Non-group C adenoviral vectors, methods of producing non-group C adenoviral vectors, and methods of using non-group C adenoviral vectors useful in the present invention are disclosed in, for example, U.S. Pat. Nos. 5,801,030, 5,837,511, and 5,849,561, and International Patent Applications WO 97/12986 and WO 98/53087. Any adenovirus, even a chimeric adenovirus, can be used as the source of the viral genome for an adenoviral vector. For example, a human adenovirus can be used as the source of the viral genome for a replication deficient adenoviral vector. Further examples of adenoviral vectors useful in the present invention can be found in U.S. Publication Nos. 20150093831, 20140248305, 20120283318, 20100008889, 20090175897 and 20090088398, the description of which viral vectors and methods of their making being incorporated by reference in its entirety.

In some embodiments, the viral vectors provided herein can also be based on AAVs. AAV vectors have been of particular interest for use in therapeutic applications such as those described herein. AAV is a DNA virus, which is not known to cause human disease. Generally, AAV requires co-infection with a helper virus (e.g., an adenovirus or a herpes virus), or expression of helper genes, for efficient replication. AAVs have the ability to stably infect host cell genomes at specific sites, making them more predictable than retroviruses; however, generally, the cloning capacity of the vector is 4.9 kb. AAV vectors that have been used in gene therapy applications generally have had approximately 96% of the parental genome deleted, such that only the terminal repeats (ITRs), which contain recognition signals for DNA replication and packaging, remain. For a description of AAV-based vectors useful in the present invention, see, for example, U.S. Pat. Nos. 8,679,837, 8,637,255, 8,409,842, 7,803,622, and 7,790,449, and U.S. Publication Nos. 0150065562, 20140155469, 20140037585, 20130096182, 20120100606, and 20070036757, the viral vectors of which and methods for their making being incorporated herein by reference in their entirety. The AAV vectors may be recombinant AAV vectors. The AAV vectors may also be self-complementary (sc) AAV vectors, which are described, for example, in U.S. Patent Publications 2007/01110724 and 2004/0029106, and U.S. Pat. Nos. 7,465,583 and 7,186,699, the vectors and methods of production of which are herein incorporated by reference.

In some embodiments, the viral vector (e.g., AAV vector) included in the methods and compositions described herein is configured to deliver a RNA molecule. In some embodiments, the viral vector is configured to deliver a small interfering RNA (siRNA). In other embodiments, the viral vector is configured to deliver a microRNA (miRNA), a short hairpin RNA (shRNA), an mRNA, or a small activating RNA (saRNA). In alternative embodiments, the viral vector is configured to deliver a DNA molecule, including a single stranded DNA (ssDNA), with may encode a cDNA or a fragment thereof.

The AAV on which a viral vector may be based can be of any serotype or a mixture of serotypes. AAV serotypes include AAVl, AAV 2, AAV3, AAV4, AAV5, AAV6, AAV7, AAV8, AAV9, AAVl0, and AAVll. For example, when the viral vector is based on a mixture of serotypes, the viral vector may contain the capsid signal sequences taken from one AAV serotype (for example, selected from any one of AAV serotypes 1, 2, 3, 4, 5, 6, 7, 8, 9, 10, and 11) and packaging sequences from a different serotype (for example, selected from any one of AAV serotypes 1, 2, 3, 4, 5, 6, 7, 8, 9, 10, and 11). In some embodiments of any one of the methods or compositions provided herein, therefore, the AAV vector is an AAV 2/8 vector. In other embodiments of any one of the methods or compositions provided herein, the AAV vector is an AAV 2/5 vector.

In some embodiments, the viral vectors provided herein may be based on an alphavirus. Alphaviruses include Sindbis (and VEEV) virus, Aura virus, Babanki virus, Barmah Forest virus, Bebaru virus, Cabassou virus, Chikungunya virus, Eastern equine encephalitis virus, Everglades virus, Fort Morgan virus, Getah virus, Highlands J virus, Kyzylagach virus, Mayaro virus, Me Tri virus, Middelburg virus, Masso das Pedras virus, Mucambo virus, Ndumu virus, O'nyong-nyong virus, Pixuna virus, Rio Negro virus, Ross River virus, Salmon pancreas disease virus, Semliki Forest virus, Southern elephant seal virus, Tonate virus, Trocara virus, Una virus, Venezuelan equine encephalitis virus, Western equine encephalitis virus, and Whataroa virus. Generally, the genome of such viruses encode nonstructural (e.g., replicon) and structural proteins (e.g., capsid and envelope) that can be translated in the cytoplasm of the host cell. Ross River virus, Sindbis virus, Semliki Forest virus (SFV), and Venezuelan equine encephalitis virus (VEEV) have all been used to develop viral vectors for transgene delivery. Pseudotyped viruses may be formed by combining alphaviral envelope glycoproteins and retroviral capsids. Examples of alphaviral vectors can be found in U.S. Publication Nos. 20150050243, 20090305344, and 20060177819; the vectors and methods of their making are incorporated herein by reference in their entirety. Viral vectors can be used to deliver transgenes for a variety of purposes, including for gene editing, the methods and compositions provided herein are also so applicable.

Viral Vector: Therapeutic Protein or Portion Thereof

In some embodiments, a viral vector may include a transgene that encodes a therapeutic protein or portion thereof as provided herein. Examples of such proteins include, but are not limited to, infusible or injectable therapeutic proteins, enzymes, enzyme cofactors, hormones, blood or blood coagulation factors, cytokines and interferons, growth factors, adipokines, monoclonal antibodies, etc.

In some embodiments, a viral vector may include a transgene that encodes an enzyme (e.g., for an enzyme replacement therapy). Examples of such enzymes include, but are not limited to, lysozyme, oxidoreductases, transferases, hydrolases, lyases, isomerases, asparaginases, uricases, glycosidases, proteases, nucleases, collagenases, hyaluronidases, heparinases, heparanases, kinases, phosphatases, lysins and ligases. Other examples of enzymes include those that used for enzyme replacement therapy including, but not limited to, imiglucerase (e.g., CEREZYME™), a-galactosidase A (a-gal A) (e.g., agalsidase beta, FABRYZYME), acid a-glucosidase (GAA) (e.g., alglucosidase alfa, LUMIZYME™, MYOZYME™), and arylsulfatase B (e.g., laronidase, ALDURAZYME™, idursulfase, ELAPRASE™, arylsulfatase B, NAGLAZYME™).

In some embodiments, a viral vector may include a transgene that encodes a blood or blood coagulation factor. Examples of such blood or blood coagulation factors include, but are not limited to, Factor I (fibrinogen), Factor II (prothrombin), tissue factor, Factor V (proaccelerin, labile factor), Factor VII (stable factor, proconvertin), Factor VIII (antihemophilic globulin), Factor IX (Christmas factor or plasma thromboplastin component), Factor X (Stuart-Prower factor), Factor Xa, Factor XI, Factor XII (Hageman factor), Factor XIII (fibrin-stabilizing factor), von Willebrand factor, von Heldebrant Factor, prekallikrein (Fletcher factor), high-molecular weight kininogen (HMWK) (Fitzgerald factor), fibronectin, fibrin, thrombin, antithrombin, such as antithrombin III, heparin cofactor II, protein C, protein S, protein Z, protein Z-related protease inhibitor (ZPI), plasminogen, alpha 2-antiplasmin, tissue plasminogen activator (tPA), urokinase, plasminogen activator inhibitor-I (PAli), plasminogen activator inhibitor-2 (PAI2), cancer procoagulant, and epoetin alfa (Epogen, Procrit).

In some embodiments, a viral vector may include a transgene that encodes a cytokine. Examples of such cytokines include, but are not limited to, lymphokines, interleukins, and chemokines, type 1 cytokines, such as IFN-γ, TGF-b, and type 2 cytokines, such as IL-4, IL-10, and IL-13.

In some embodiments, a viral vector may include a transgene that encodes a growth factor. Examples of such growth factors include, but are not limited to, Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-a), Transforming growth factor beta (TGF-b), Tumor necrosis factor-alpha (TNF-a), Vascular endothelial growth factor (VEGF), Wnt Signaling Pathway, placental growth factor (PIGF), [(Foetal Bovine Somatotrophin)] (FBS), IL-1, IL-2, IL-3, IL-4, IL-5, IL-6, and IL-7.

In some embodiments, a viral vector may include a transgene that encodes an adipokine. Examples of such adipokines, include, but are not limited to, leptin and adiponectin.

In some embodiments, a viral vector may include a transgene that encodes one or more of, receptors, signaling proteins, cytoskeletal proteins, scaffold proteins, transcription factors, structural proteins, membrane proteins, cytosolic proteins, binding proteins, nuclear proteins, secreted proteins, golgi proteins, endoplasmic reticulum proteins, mitochondrial proteins, and vesicular proteins, etc.

Additionally, a viral vector may include a transgene that encodes other therapeutic proteins, such as functional versions of proteins associated with disorders of lipid and sphingolipid degradation (e.g., Galactosidase-1, Hexosaminidase A, Hexosaminidases A and B, GM2 Activator Protein, 8-Galactosidase A, Glucocerebrosidase, Glucocerebrosidase, Glucocerebrosidase, Arylsulfatase A, Galactosylceramidase, Sphingomyelinase, Sphingomyelinase, NPCI, Acid Ceramidase, Lysosomal Acid Lipase); disorders of mucopolysaccharide degradation (e.g., L-Iduronidase, Iduronate Sulfatase, Heparan N-Sulfatase, N-Acetylglucosaminidase, Acetyl-CoA-Glucosaminidase, Acetyltransferase, Acetylglucosamine-6-Sulfatase, Galactosamine-6-Sulfatase, Arylsul-fatase B, Glucuronidase); disorders of glycoprotein degradation (e.g., Mannosidase, mannosidase, 1-fucosidase, Aspartylglycosaminidase, Neuraminidase, Lysosomal protective protein, Lysosomal 8-N-acetylgalactosaminidase, Lysosomal 8-N-acetylgalactosaminidase); lysosomal storage disorders (e.g., Palmitoyl-protein thioesterase, at least 4 subtypes, Lysosomal membrane protein, Unknown, Glucose-6-phosphatase, Glucose-6-phosphate translocase, Acid maltase, Debrancher enzyme amylo-1,6 glucosidase, N-acetylglucosamine-1-phosphotransferase, N-acetylglucosamine-1-phosphotransferase, Ganglioside sialidase (neuraminidase), Lysosomal cystine transport protein, Lysosomal cystine transport protein, Lysosomal cystine transport protein, Sialic acid transport protein Saposins, A, B, C, D) and leukodystrophies (e.g., Microsomal triglyceride transfer protein/apolipoprotein B, Peroxisomal membrane transfer protein, Peroxins, Aspartoacylase, Sterol-27-hydroxlase, Proteolipid protein, ABC transporter, Peroxisome membrane protein 3 or Peroxisome biogenesis factor 1, Phytanic acid oxidase).

Viral Vector: Gene Editing

In some embodiments, the viral vectors described herein (e.g., viral vectors that may be used as therapeutic agents to which tolerance can be induced using the methods and compositions of the present invention) may be used for gene editing. In such embodiments, the transgene of the viral vector is a gene editing transgene. Such a transgene encodes a component that is involved in a gene editing process. Generally, such a process results in long-lasting or permanent modifications to genomic DNA, such as targeted DNA insertion, replacement, mutagenesis or removal. Gene editing may include the delivery of nucleic acids encoding a DNA sequence of interest and inserting the sequence of interest at a targeted site in genomic DNA using endonucleases. Thus, gene editing transgenes may comprise these nucleic acids encoding a DNA sequence of interest for insertion. In some embodiments, the DNA sequence for insertion is a DNA sequence encoding any one of the therapeutic proteins provided herein or a portion thereof. Alternatively, or in addition to, the gene editing transgene may comprise nucleic acids that encode one of more components that carry out the gene editing process. The gene editing transgenes provided herein may encode an endonuclease and/or a guide RNA, etc.

Endonucleases can create breaks in double-stranded DNA at desired locations in a genome and use the host cell's mechanisms to repair the break using homologous recombination, nonhomologous end-joining, etc. Classes of endonucleases that can be used for gene editing include, but are not limited to, meganucleases, zinc-finger nucleases (ZFNs), transcription activator-like effector nucleases (TALENs), clustered regularly interspaced short palindromic repeat(s) (CRISPR) and homing endonucleases. The gene editing transgene of the viral vectors provided herein may encode any one of the endonucleases provided herein.

In some embodiments, a viral vector may include a transgene that encodes a meganuclease. Meganucleases are generally characterized by their capacity to recognize and cut DNA sequences (14-40 base pairs). In addition, known techniques, such as mutagenesis and high-throughput screening and combinatorial assembly, can be used to create custom meganucleases, where protein subunits can be associated or fused. Examples of meganucleases can be found in U.S. Pat. Nos. 8,802,437, 8,445,251 and 8,338,157; and U.S. Publication Nos. 20130224863, 20110113509 and 20110033935, the meganucleases of which are incorporated herein by reference.

In some embodiments, a viral vector may include a transgene that encodes a zinc finger nuclease. A zinc finger nuclease typically comprises a zinc finger domain that binds a specific target site within a nucleic acid molecule, and a nucleic acid cleavage domain that cuts the nucleic acid molecule within or in proximity to the target site bound by the binding domain. Typical engineered zinc finger nucleases comprise a binding domain having between 3 and 6 individual zinc finger motifs and binding target sites ranging from 9 base pairs to 18 base pairs in length. Zinc finger nucleases can be designed to target virtually any desired sequence in a given nucleic acid molecule for cleavage. For example, zinc finger binding domains with a desired specificity can be designed by combining individual zinc finger motifs of known specificity. The structure of the zinc finger protein Zif268 bound to DNA has informed much of the work in this field and the concept of obtaining zinc fingers for each of the 64 possible base pair triplets and then mixing and matching these modular zinc fingers to design proteins with any desired sequence specificity has been described (Pavletich N P, Pabo C O (May 1991). "Zinc finger-DNA recognition: crystal structure of a Zif268-DNA complex at 2.1 Å". Science 252 (5007): 809-17, the entire contents of which are incorporated herein). In some embodiments, bacterial or phage display is employed to develop a zinc finger domain that recognizes a desired nucleic acid sequence, for example, a desired endonuclease target site. Zinc finger nucleases, in some embodiments, comprise a zinc finger binding domain and a cleavage domain fused or otherwise conjugated to each other via a linker, for example, a polypeptide linker. The length of the linker can determine the distance of the cut from the nucleic acid sequence bound by the zinc finger domain. Examples of zinc finger nucleases can be found in U.S. Pat. Nos. 8,956,828; 8,921,112; 8,846,578; 8,569,253, the zinc finger nucleases of which are incorporated herein by reference.

In some embodiments, a viral vector may include a transgene that encodes a transcription activator-like effector nucleases (TALEN). TALENs are artificial restriction enzymes produced by fusing specific DNA binding domains to generic DNA cleaving domains. The DNA binding domains, which can be designed to bind any desired DNA sequence, come from transcription activator-like (TAL) effectors, DNA-binding proteins excreted by certain bacteria that infect plants. Transcription activator-like effectors (TALEs) can be engineered to bind practically any DNA sequence or joined together into arrays in combination with a DNA cleavage domain. TALENs can be used similarly to design zinc finger nucleases. Examples of TALENS can be found in U.S. Pat. No. 8,697,853; as well as U.S. Publication Nos. 20150118216, 20150079064, and 20140087426, the TALENS of which are incorporated herein by reference.

The CRISPR (clustered regularly interspaced short palindromic repeats)/Cas system can also be used as a tool for gene editing. In a CRISPR/Cas system, guide RNA (gRNA) is encoded genomically or episomally (e.g., on a plasmid). The gRNA forms a complex with an endonuclease, such as Cas9 endonuclease, following transcription. The complex is then guided by the specificity determining sequence (SDS) of the gRNA to a DNA target sequence, typically located in the genome of a cell. Cas9 or Cas9 endonuclease refers to an RNA-guided endonuclease comprising a Cas9 protein, or a fragment thereof (e.g., a protein comprising an active or inactive DNA cleavage domain of Cas9 or a partially inactive DNA cleavage domain (e.g., a Cas9 nickase), and/or the gRNA binding domain of Cas9). Cas9 recognizes a short motif in the CRISPR repeat sequences (the PAM or protospacer adjacent motif) to help distinguish self versus non-self. Cas9 endonuclease sequences and structures are well known to those of skill in the art (see, e.g., "Complete genome sequence of an MI strain of *Streptococcus pyogenes*." Ferretti J. J., McShan W. M., Ajdic D. J., Savic D. J., Savic G., Lyon K., Primeaux C., Sezate S., Suvorov A. N., Kenton S., Lai H. S., Lin S. P., Qian Y., Jia H. G., Najar F. Z., Ren Q., Zhu H., Song L. expand/collapse author list McLaughlin R. E., Proc. Natl. Acad. Sci. U.S.A. 98:4658-4663(2001); "CRISPR RNA maturation by trans-encoded small RNA and host factor RNase III." Deltcheva E., Chylinski K., Sharma C. M., Gonzales K., Chao Y., Pirzada Z. A., Eckert M. R., Vogel J., Charpentier E., Nature 471:602-607 (2011); and "A programmable dual-RNA-guidedDNAendo-nuclease in adaptive bacterial immunity." Jinek M., Chylinski K., Fonfara I., Hauer M., Doudna J. A., Charpentier E. Sci-ence 337:816-821(2012)). Single guide RNAs ("sgRNA", or simply "gNRA") can be engineered so as to incorporate aspects of both the crRNA and tracrRNA into a single RNA species. See e.g., Jinek M., Chylinski K., Fonfara I., Hauer M., Doudna J. A., Charpentier E. Science 337:816-821 (2012). In some embodiments, a viral vector may include a transgene that encodes a Cas9 endonuclease.

Cas9 orthologs have been described in various species, including, but not limited to, S. pyogenes and S. thermophilus. Additional suitable Cas9 endonucleases and sequences will be apparent to those of skill in the art, and such Cas9 endonucleases and sequences include Cas9 sequences from the organisms and loci disclosed in Chylinski, Rhun, and Charpentier, "The tracrRNA and Cas9 families of type II CRISPR-Cas immunity systems" (2013) RNA Biology 10:5, 726-737. In some embodiments, a gene editing transgene encodes a wild-type Cas9, fragment or a Cas9 variant. A "Cas9 variant" is any protein with a Cas9 function that is not identical to a Cas9 wild-type endonuclease as it occurs in nature. In some embodiments, a Cas9 variant shares homology to a wild-type Cas9, or a fragment thereof. A Cas9 variant in some embodiments has at least 40% sequence identity to Streptococcus pyogenes or S. thermophilus Cas9 protein and retains the Cas9 functionality. Preferably, the sequence identity is at least 90%, 95%, or more. More preferably, the sequence identity is at least 98% or 99% sequence identity. In some embodiments of any one of the Cas9 variants for use in any one of the methods provided herein the sequence identity is amino acid sequence identity. Cas9 variants also include Cas9 dimers, Cas9 fusion proteins, Cas9 fragments, minimized Cas9 proteins, Cas9 variants without a cleavage domain, Cas9 variants without a gRNA domain, Cas9-recombinase fusions, fCas9, FokI-dCas9, etc. Examples of such Cas9 variants can be found, for example, in U.S. Publication Nos. 20150071898 and 20150071899, the description of Cas9 proteins and Cas9 variants of which is incorporated herein by reference. Cas9 variants also include Cas9 nickases, which comprise mutation(s) which inactivate a single endonuclease domain in Cas9. Such nickases can induce a single strand break in a target nucleic acid as opposed to a double strand break. Cas9 variants also include Cas9 null nucleases, a Cas9 variant in which one nuclease domain is inactivated by a mutation. Examples of additional Cas9 variants and/or methods of identifying further Cas9 variants can be found in U.S. Publication Nos. 20140357523, 20150165054 and 20150166980, the contents of which pertaining to Cas9 proteins, Cas9 variants and methods of their identification being incorporated herein by reference.

Still other examples of Cas9 variants include a mutant form, known as Cas9D10A, with only nickase activity. Cas9D10A is appealing in terms of target specificity when loci are targeted by paired Cas9 complexes designed to generate adjacent DNA nicks. Another example of a Cas9 variant is a nuclease-deficient Cas9 (dCas9). Mutations H840A in the HNH domain and D10A in the RuvC domain inactivate cleavage activity, but do not prevent DNA binding. Therefore, this variant can be used to sequence-specifically target any region of the genome without cleavage. Instead, by fusing with various effector domains, dCas9 can be used either as a gene silencing or activation tool. The gene editing transgene, in some embodiments, may encode any one of the Cas9 variants provided herein.

Methods of using RNA-programmable endonucleases, such as Cas9, for site-specific cleavage (e.g., to modify a genome) are known in the art (see e.g., Cong, L. et al. Multiplex genome engineering using CRISPR/Cas systems. Science 339, 819-823 (2013); Mali, P. et al. RNA-guided human genome engineering via Cas9. Science 339, 823-826 (2013); Hwang, W. Y. et al. Efficient genome editing in zebrafish using a CRISPR-Cas system. Nature biotechnology 31, 227-229 (2013); Jinek, M. et al. RNA-programmed genome editing in human cells. eLife 2, e00471 (2013); Dicarlo, J. E. et al. Genome engineering in Saccharomyces cerevisiae using CRISPR-Cas systems. Nucleic acids research (2013); Jiang, W. et al. RNA-guided editing of bacterial genomes using CRISPR-Cas systems. Nature biotechnology 31, 233-239 (2013)).

In some embodiments, a viral vector may include a transgene that encodes a homing endonuclease. Homing endonucleases can catalyze, at few or singular locations, the hydrolysis of the genomic DNA used to synthesize them, thereby transmitting their genes horizontally within a host, increasing their allele frequency. Homing endonucleases generally have long recognition sequences, they thereby have low probability of random cleavage. One allele carries the gene (homing endonuclease gene+, HEG+), prior to transmission, while the other does not (HEG−), and is susceptible to enzyme cleavage. The enzyme, once synthesized, breaks the chromosome in the HEG−allele, initiating a response from the cellular DNA repair system which takes the pattern of the opposite, using recombination, undamaged DNA allele, HEG+ that contains the gene for the endonuclease. Thus, the gene is copied to another allele that initially did not have it, and it is propagated through successively. Examples of homing endonucleases can be found, for example, in U.S. Publication No. 20150166969; and U.S. Pat. No. 9,005,973, the homing endonucleases of which are incorporated herein by reference.

The sequence of a transgene may also include an expression control sequence. Expression control DNA sequences include promoters, enhancers, and operators, and are generally selected based on the expression systems in which the expression construct is to be utilized. In some embodiments, promoter and enhancer sequences are selected for the ability to increase gene expression, while operator sequences may be selected for the ability to regulate gene expression. The transgene may also include sequences that facilitate, and preferably promote, homologous recombination in a host cell. The transgene may also include sequences that are necessary for replication in a host cell.

Exemplary expression control sequences include promoter sequences, e.g., cytomegalovirus promoter; Rous sarcoma virus promoter; and simian virus 40 promoter; as well as any other types of promoters that are disclosed elsewhere herein or are otherwise known in the art. Generally, promoters are operatively linked upstream (i.e., 5') of the sequence coding for a desired expression product. The transgene also may include a suitable polyadenylation sequence (e.g., the SV40 or human growth hormone gene polyadenylation sequence) operably linked downstream (i.e., 3') of the coding sequence.

Antigen to ITE Stoichiometry

Various antigen-to-ITE ratios can be used, depending on the antigen and type of disease being treated. In some instances, the mass ratio of antigen-to-ITE is from 1:10 to 100:1 (e.g., from 1:5 to 50:1, from 1:4 to 20:1, or from 1:3 to 10:1, e.g., from 1:10 to 1:8, from 1:8 to 1:6, from 1:6 to 1:4, from 1:4 to 1:2, from 1:2 to 1:1, from 1:1 to 2:1, from 2:1 to 3:1, from 3:1 to 4:1, from 4:1 to 5:1, from 5:1 to 10:1, from 10:1 to 20:1, from 20:1 to 30:1, from 30:1 to 40:1, from 40:1 to 50:1, from 50:1 to 60:1, from 60:1 to 80:1, or from 80:1 to 100:1, e.g., about 1:100, 1:90, 1:80, 1:70, 1:60, 1:50, 1:40, 1:30, 1:20, 1:10, 1:5, 1:4, 1:3, 1:2, 1:1, 2:1, 3:1, 4:1, 5:1, 10:1, 20:1, 30:1, 40:1, 50:1, 60:1, 70:1, 80:1, 90:1, or 100:1). In some embodiments, the molar ratio of antigento-ITE is from 1:5000 to 25:1 (e.g., from 1:2000 to 20:1, from 1:1000 to 15:1, or from 1:500 to 10:1, e.g., from 1:2000 to 1:1000, from 1:1000 to 1:500, from 1:500 to 1:200, from 1:200 to 1:50, from 1:50 to 1:30, from 1:30 to 1:20, from 1:20 to 1:10, from 1:10 to 1:5, from 1:5 to 1:4, from 1:4 to 1:3, from 1:3 to 1:2, from 1:2 to 1:1, from 1:1 to 2:1, from 2:1 to 3:1, from 3:1 to 4:1, from 4:1 to 5:1, from 5:1 to 10:1, from 10:1 to 20:1, from 20:1 to 50:1, from 50:1 to 100:1, from 100:1 to 500:1, from 500:1 to 2000:1, or from 2000:1 to 5000:1, e.g., about 1:100, 1:90, 1:80, 1:70, 1:60, 1:50, 1:40, 1:30, 1:20:1:10, 1:5, 1:4, 1:3, 1:2, 1:1, 2:1, 3:1, 4:1, 5:1, 10:1, 20:1, 30:1, 40:1, 50:1, 60:1, 70:1, 80:1, 90:1, or 100:1).

Methods of Treatment and Prevention

The compositions and methods described herein are of particular use for treating a patient (e.g., a human) that would benefit from therapeutic immunomodulation (e.g., a patient in need of a suppressed immune response, e.g., a subject having an autoimmune disorder) or for preventing the onset of development of a disorder (e.g., an autoimmune disorder). In some embodiments, diseases or disorders that can be treated by the compositions (e.g., liposomal composition) and methods described herein may include, but are not limited to, autoimmune diseases, allergic diseases (e.g., allergies to environmental agents such as animal dander, pollen, dust mites, insect bites, and so forth, as well as food allergies to nuts, egg products, seafood, grains and so forth), hereditary diseases (treated by protein replacement therapy or gene therapy), organ transplantation (associated with immune rejection, or, in the case of bone marrow transplantation, with graft versus host disease), and a wide variety of other diseases treated by peptide or protein therapeutics (e.g., diabetes).

In some embodiments, autoimmune diseases that can be treated by the compositions (e.g., liposomal composition of the present invention) or methods described herein include, but are not limited to, diseases that affect the joints and connective tissues (e.g., ankylosing spondylitis, rheumatoid arthritis, juvenile idiopathic arthritis, psoriatic arthritis and mixed connective tissue disease), as well as diseases that affect the brain (e.g., multiple sclerosis and neuromyelitis optica), diseases that affect endocrine organs (e.g., type I diabetes, latent autoimmune diabetes in adults (LADA), autoimmune thyroid disease, Grave's disease, Hashimoto's thyroiditis and Addison's disease), diseases that affect the gastrointestinal tract (e.g., autoimmune atrophic gastritis, pernicious anemia, celiac disease, and inflammatory bowel disease (including Crohn's disease and ulcerative colitis)), diseases that affect the skin (e.g., psoriasis, scleroderma, alopecia areata, atopic dermatitis, pemphigus vulgaris and bullous pemphigoid), diseases that affect the muscle (e.g., myasthenia gravis, Guillain-Barre syndrome and poly/dermatomyositis), diseases that affect the heart (e.g., rheumatic fever), diseases that affect the liver (e.g., autoimmune hepatitis and primary sclerosing cholangitis), diseases that affect the sensory organs (e.g., autoimmune uveitis and Behcet's disease), diseases that affect the blood or bone marrow (e.g., autoimmune haemolytic anemia, idiopathic thrombocylopenic purpura and idiopathic leucopenia), diseases that affect the lungs (e.g., Goodpasture's syndrome), diseases that affect the kidney (e.g., autoimmune nephritis, including glomerulonephritis), diseases that affect the vasculature (e.g., Wegener's granulomatosis), diseases that affect the peripheral nervous system (e.g., chronic inflammatory demyelinating polyradiculoneuropathy), and diseases characterized by multi-organ involvement (e.g., systemic lupus erythematosus and Sjogren's syndrome).

The methods include selecting a patient in need of treatment and administering to the patient one or more of the compositions described herein. A subject in need of treatment can be identified, e.g., by their medical practitioner.

A therapeutically effective amount of one or more of the compositions described herein can be administered by standard methods, for example, by one or more routes of administration, e.g., by one or more of the routes of administration currently approved by the United States Food and Drug Administration (FDA; see, for example world wide web address fda.gov/cder/dsm/DRG/drg00301.htm). Tolerogenic liposomes or pharmaceutical compositions thereof can be administered systemically or locally, e.g., parenterally via intravenous, subcutaneous, intradermal (including intra-epidermal), intra-articular, pulmonary or mucosal (including nasal) routes. In some embodiments, compositions may be administered intrahepatically, intracerebrally, intramuscularly, percutaneously, intraarterially, intraperitoneally, intralesionally, intracranially, intraarticularly, intraprostatically, intrapleurally, intratracheally, intrathecally, intranasally, intravaginally, intrarectally, intratumorally, subcutaneously, subconjunctivally, intravesicularly, mucosally, intrapericardially, intraumbilically, orally, topically, transdermally, by inhalation, by aerosolization, by injection, by implantation, by infusion (e.g., by continuous infusion), by catheter, by lavage, or in creams.

The amount of liposomes administered to the patient may vary depending on the concentration of antigen and/or ITE. In some embodiments, the amount of ITE in a single dose of liposomes is between about 50 µg and 15 mg (e.g., from 75 µg to 100 µg, from 100 µg to 150 µg, from 150 µg to 300 µg, from 300 µg to 500 µg, from 500 µg to 750 µg, from 750 µg to 1500 µg, from 1500 µg to 5000 µg, or from 5000 µg to 15000 µg). For example, the amount of ITE in a single dose of liposomes can be from 100 µg to 1000 µg (e.g., from 200 µg to 800 µg, e.g., about 200 µg, about 300 µg, about 400 µg, about 500 µg, about 600 µg, about 700 µg, about 800 µg, about 1000 µg, or about 1500 µg).

Pharmaceutical compositions of tolerogenic liposomes can be of any suitable concentration for the intended route of administration.

In some embodiments, a single unit dose of tolerogenic liposomes (e.g., a single dose containing any of the aforementioned amounts of ITE) can include from $10^{11}$ to $10^{16}$ liposomes (e.g., from $10^{11}$ to $10^{16}$ liposomes, from $10^{11}$ to $10^{15}$ liposomes, from $10^{12}$ to $10^{14}$ liposomes, or about $10^{13}$ liposomes, e.g., from $10^{11}$ to $10^{12}$ liposomes, from $10^{12}$ to $10^{13}$ liposomes, from $10^{13}$ to $10^{14}$ liposomes, from $10^{14}$ to $10^{15}$ liposomes, or from $10^{15}$ to $10^{16}$ liposomes, e.g., from $10^{12}$ to $10^{15}$ liposomes, from $5.0 \times 10^{13}$ to $1.0 \times 10^{14}$ liposomes, e.g., about $8 \times 10^{13}$ liposomes).

Compositions can be administered once or multiple times over the course of a treatment period of weeks, months or years (e.g., until tolerance to a disease-relevant autoantigen is induced). In some instances, compositions are administered to the subject once per day, five times per week, four times per week, three times per week, twice per week, once every two weeks, once every three weeks, monthly, bimonthly, five times per year, four times per year, three times per year, twice per year, or once per year.

The examples that follow do not limit the scope of the embodiments described herein. One skilled in the art will appreciate that modifications can be made in the following examples which are intended to be encompassed by the spirit and scope of the invention.

EXAMPLES

Various formulations of nanoparticulate liposomes containing ITE and/or myelin oligodendrocyte glycoprotein (MOG) antigen were synthesized, characterized, and tested in animal models of autoimmunity as described in the following Examples:

Example 1. Formulation and Characterization of ITE-Loaded Micelles 2-(1H-Indol-3-ylcarbonyl)-4-thiazolecarboxylic acid methyl ester (ITE) is a potent aryl hydrocarbon receptor agonist which is difficult to formulate in nanoparticulate form (including gold and PLGA nanoparticles and many conventional liposomal compositions, for example). One contributing factor is the low solubility of lipophilic ITE in many conventional solvents, including water (~115 micromolar), methanol (~3 millimolar) and ethanol (~3.3 millimolar). ITE is also highly prone to self-aggregation.

This example provides exemplary methods of loading ITE into micelles using DSPE-PEG, TPGS, and mixtures thereof, and characterization of each is provided herein.

Method 1: DSPE-PEG Micelles 1,2-distearoyl-sn-glycero-3-phosphoethanolamine-N-[methoxy(polyethylene glycol)-2000] (PEG2000-DSPE, Avanti Polar Lipids cat. #880120) was dissolved in chloroform in a borosilicate glass tube to a concentration of either 15, 20, 25, 30, 35, or 40 mM (batches 1-6, respectively). ITE (1 mg powder) was added to 0.5 ml of each of the PEG2000-DSPE/chloroform solutions and mixed by vortexing and intermittent heating at 50° C. until ITE dissolved completely and a clear solution was obtained. The chloroform was then evaporated under nitrogen, leaving a thin film on the inner sides of the glass tubes. The tubes were freeze-dried overnight to remove all traces of chloroform. The dried PEG2000-DSPE/ITE film on the glass wall was hydrated by adding 0.5 ml HEPES buffered saline (HBS; pH 6.5). Complete suspension of lipid film was accomplished by vortexing and briefly sonicating in a bath-type sonicator (FS20D, Fisher Scientific). The resulting micelles were centrifuged at 10,000 g for 10 minutes and passed through 0.2 micron polyethersulfone (PES) filters to remove any unencapsulated or precipitated ITE. Micelles were then characterized with respect to size, polydispersity, and charge using a Malvern Zetasizer. The amount of loaded ITE was determined by dissolving the micelle preparations in methanol:acetic acid (99:1 v/v). ITE absorbs light at 355 nanometers, a wavelength at which lipids do not absorb, enabling spectrophotometric measurement of ITE concentration. A standard curve relating ITE concentration to absorbance at 355 nanometers was produced and used to measure ITE loading. ITE encapsulation was calculated as the fraction of starting ITE (1 mg) encapsulated in micelles. ITE loading was calculated as the percent of the final micelle mass contributed by ITE. Results are summarized in Table 1, below, and illustrated in FIG. 1.

Micelle size did not vary significantly with PEG2000-DSPE concentration, but polydispersity was lower at higher lipid concentrations. Visual observation showed that higher PEG2000-DSPE concentrations were able to carry more ITE, as there was visible ITE precipitation in batch 1 but not in batch 6. ITE measurement confirmed this observation, as batch 1 micelles (15 mM lipid) had the lowest encapsulation efficiency (11.3%) while batch 4 (30 mM lipid) had the highest encapsulation efficiency (29.8%), as shown in FIG. 1.

Method 2: TPGS Micelles

D-α-Tocopherol polyethylene glycol 1000 succinate (TPGS-1000; Millipore-Sigma cat. #57668) was dissolved in 0.5 ml chloroform in borosilicate glass tubes at concentrations of 15, 25, 35, 45, 55, 65 and 75 mg/ml (batches 1-7, respectively). One milligram of ITE was added to each tube, yielding a ratio of ITE:TPGS-1000 varying from 1.33% to 6.67% (w/w), as shown in Table 2, below. ITE and TPGS were dissolved in chloroform by vortexing. Chloroform was evaporated under a nitrogen stream, depositing a thin film of ITE and lipid on the walls of the glass tubes. Samples were freeze-dried overnight to remove any traces of chloroform. Samples were rehydrated with 1 ml HBS by vortexing, intermittent heating, and sonication to fully dissolve the film. Samples were incubated at 50° C. for 45 min. Micelles were centrifuged at 10,000 g for 10 min, then filtered through 0.22μ PES filters to remove any unencapsulated ITE. Micelles were characterized for size, charge and ITE loading as in Method 1.

TABLE 2

Encapsulation of ITE in TPGS-1000 micelles

| Batch | TPGS-1000 conc. | TPGS-1000 (mg): ITE (mg) | Encapsulated ITE (mg/mL) | Encapsulated ITE (%) | Micelle diameter (nm) ± SD | PDI |
|---|---|---|---|---|---|---|
| 1 | 9.9 mM | 15:1 | 0.087 | 8.7 | 16.8 ± 4.7 | 0.340 |
| 2 | 16.5 mM | 25:1 | 0.132 | 13.2 | 13.8 ± 3.7 | 0.246 |
| 3 | 23.1 mM | 35:1 | 0.226 | 22.6 | 12.8 ± 4.4 | 0.087 |
| 4 | 29.7 mM | 45:1 | 0.330 | 33.0 | 14.3 ± 5.7 | 0.176 |
| 5 | 36.4 mM | 55:1 | 0.381 | 38.1 | 13.9 ± 5.8 | 0.159 |
| 6 | 43.0 mM | 65:1 | 0.474 | 47.4 | 12.6 ± 3.4 | 0.039 |
| 7 | 49.6 mM | 75:1 | 0.703 | 70.3 | 12.5 ± 3.2 | 0.026 |

Figure 2:
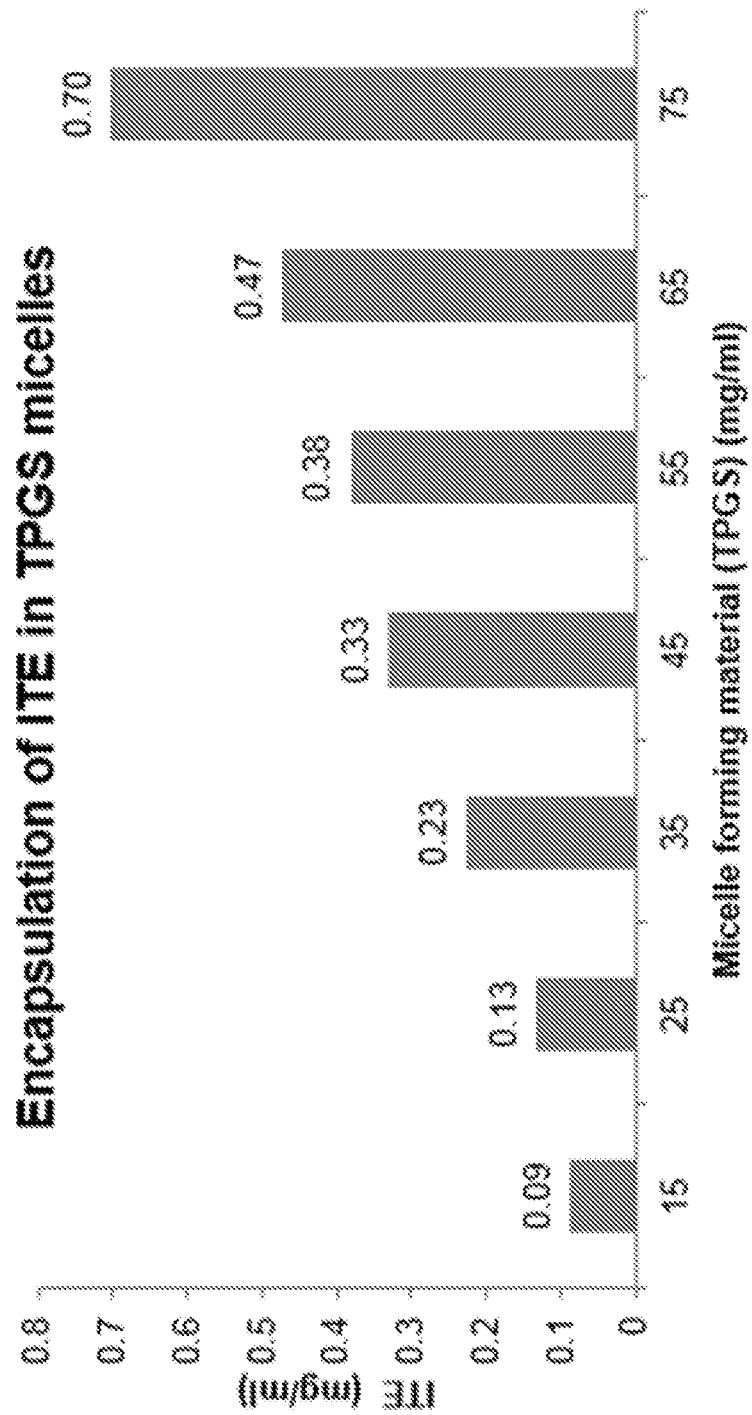
FIG. 2 is a graph showing ITE encapsulation efficiency in TPGS micelles over various concentrations of TPGS.

Micelle size (~12.5-17 nm diameter) did not change significantly with TPGS-1000 concentration or ITE loading, however polydispersity decreased with increasing TPGS-1000 concentration, as shown in Table 2. As shown in FIG. 2, both the amount and percent of ITE loaded in micelles increased progressively with TPGS-1000 concentration. At the highest tested TPGS-1000 concentration (75 mg/mL; 49.6 mM) 703 micrograms of ITE was loaded (70.3% of the starting amount).

TABLE 1

Encapsulation of ITE in PEG2000-DSPE micelles

| Batch | PEG2000-DSPE concentration | Starting [ITE] (mg/mL) | Encapsulated ITE (mg/mL) | Encapsulated ITE (%) | Micelle diameter (nm) ± SD | Polydispersity Index (PDI) |
|---|---|---|---|---|---|---|
| 1 | 15 mM | 2 | 0.226 | 11.3 | 13.9 ± 4.8 | 0.10 |
| 2 | 20 mM | 2 | 0.282 | 14.1 | 15.2 ± 3.6 | 0.32 |
| 3 | 25 mM | 2 | 0.504 | 25.2 | 14.6 ± 4.8 | 0.23 |
| 4 | 30 mM | 2 | 0.596 | 29.8 | 13.2 ± 5.2 | 0.15 |
| 5 | 35 mM | 2 | 0.383 | 19.1 | 12.7 ± 5.0 | 0.19 |
| 6 | 40 mM | 2 | 0.514 | 25.9 | 11.2 ± 3.3 | 0.049 |

The overall characteristics of TPGS-1000 micelles (size, ITE loading) were similar to PEG2000-DSPE micelles. However, the top TPGS-1000 lipid concentration yielded the highest ITE loading of any micelle formulation and had the lowest dispersity.

Method 3: Mixed Micelles

The two lipids used in methods 1 and 2 (PEG2000-DSPE and TPGS-1000) were combined in various ratios to synthesize mixed micelles. Total lipid concentration was fixed at 50 mg/mL of micelles. The following PEG2000-DSPE:TPGS-1000 ratios (w/w) were prepared: 0.1, 0.25, 0.5, 1, 1.5 and 2. First, the two lipids were weighed and dissolved in 0.5 mL chloroform in glass tubes. Next, 1 mg ITE was added to the chloroform solution and dissolved with vigorous vortexing, intermittent heating to 50° C., and sonication as necessary. Once ITE was completely dissolved, the chloroform was evaporated at room temperature under a stream of nitrogen gas and dry glass tubes were freeze-dried overnight to remove any remaining traces of chloroform. The lipid/ITE film was rehydrated in 1.0 mL HBS as above. After one hour, preparations were centrifuged at 10,000 g for 10 minutes and filtered through 0.22 µm PES filters. Micelle characterization was performed as described above.

Size and dispersity did not vary significantly among the batches, as shown in Table 3, below. There was a trend towards greater ITE loading in micelles with higher fractional TPGS-1000. The two highest loadings (40.1% and 37%) were achieved at the top two TPGS-1000 levels (batches 1 and 2).

TABLE 3

Encapsulation of ITE in mixed micelles

| Batch | Molar ratio PEG 2000-DSPE to TPGS-1000 | Amounts (50 mg total) | Encapsulated ITE (mg/mL) | Encapsulated ITE (%) | Micelle diameter (nm) ± SD | PDI |
|---|---|---|---|---|---|---|
| 1 | 0.1 | 8 + 42 | 0.370 | 37.0 | 17.4 ± 11.7 | 0.189 |
| 2 | 0.25 | 16 + 34 | 0.401 | 40.1 | 14.0 ± 5.1 | 0.173 |
| 3 | 0.5 | 24 + 26 | 0.308 | 30.8 | 20.4 ± 10.9 | 0.175 |
| 4 | 1 | 32.5 + 17.5 | 0.294 | 29.4 | 15.2 ± 7.8 | 0.170 |
| 5 | 1.5 | 36.8 + 13.2 | 0.274 | 27.6 | 14.7 ± 6.1 | 0.146 |
| 6 | 2 | 39.4 + 10.6 | 0.251 | 25.1 | 14.5 ± 6.2 | 0.164 |

Mixed micelles composed of PEG2000-DSPE and TPGS-1000 were not substantially different from their single-lipid counterparts. Taking into account the lipid concentration (50 mg/ml), however, micelles composed of two (or more) lipids provide increased flexibility in optimizing pharmaceutical properties such as, for example, in vivo half-life, rate of drug release, drug release into different cell compartments (e.g. cytosol vs. endosomes), and interaction with the surface of dendritic cells.

Example 2. ITE-Loaded Liposomes Using Micelle Transfer

Encapsulation of ITE in liposomes composed of saturated lipids (e.g. DMPC:cholesterol, or DSPC:cholesterol) did not yield satisfactory results because ITE, an aggregation-prone molecule, precipitated on contact with aqueous solution. Even when added in a small volume of DMSO (less than 1% of the final volume), ITE precipitated. A variety of measures for solvating ITE were tested, such as pH variation or addition of bovine serum albumin (as a binding surface for ITE), but none of these methods could solubilize ITE. To circumvent this problem, fusion of ITE-loaded micelles with pre-formed liposomes was attempted.

Micelles were prepared as in Example 1 (batch 6, Table 1). Liposomes were prepared with DSPC:cholesterol (3:2 w/w) using the ethanol injection method, as described in Batzri and Korn, *Biochimica et Biophysica Acta—Biomembranes* 1973, 298(4): 1015-19. Lipids were dissolved in 0.250 mL ethanol. The ethanolic solution was then injected into (2 mL) of HEPES buffered saline, pH 6.5, and stirred for 30 minutes. Resulting multi-lamellar vesicles were sequentially extruded through 400, 200, and 100 nm polycarbonate filters at 65° C. and purified on PD-10 columns. Liposomes were then mixed with ITE-loaded PEG-DSPE micelles at a molar ratio of (PEG:DSPC 12:1) based on lipid concentrations, at 65° C., and incubated for one hour. Liposomes were analyzed for size and charge as in Example 1. ITE content was measured by dissolving liposomes in methanol:acetic acid (99:1 v/v). ITE concentrations were quantified using absorbance at 355 nanometers. The amount of ITE in liposomes was divided by the amount of ITE in the micelles used to make the liposomes, and the fraction was multiplied by 100 to obtain percent ITE transfer (i.e., the efficiency of micelle transfer of ITE to liposomes).

A single population of nanoparticles was observed after micelle transfer into liposomes, having an average size of 133.7±34.5 nm, indicating successful removal of any free micelles after the transfer procedure. The size and size distribution of the liposomes was essentially unchanged by the micelle transfer step. The efficiency of ITE transfer from micelles to liposomes was 97.6%. The charge of liposomes before micelle transfer was −4.28 millivolts (mv) which decreased to −28.2 mv after addition of micelles, indicating the presence of negatively charged PEG on the liposome surface. Results are summarized in Table 4, below.

TABLE 4

Characterization of micelle transfer of ITE to liposomes

| Particles | Diameter (nm) ± SD | PDI | Zeta Potential | % ITE Loaded |
|---|---|---|---|---|
| Liposomes before micelle transfer | 136.4 ± 34.8 | 0.046 | −4.8 ± 6.6 | n/a |
| Liposomes after micelle transfer | 133.7 ± 34.5 | 0.034 | −28.2 ± 8.0 | 97.6% |

Encapsulation of ITE in liposomes composed primarily of saturated lipids is feasible. The ITE precipitation observed when attempting to directly load ITE into such liposomes may reflect the rapid kinetics of ITE self-association vs. the comparatively slow rate of ITE solvation by lipids, a manufacturing hurdle that can be circumvented using micelle transfer.

Example 3. Egg Phosphatidylcholine (PC) Liposomes Loaded with ITE+/−MOG$_{35-55}$ While ITE can be loaded into micelles and into liposomes via the micelle transfer procedure, providing flexibility in lipid selection, a method for directly loading ITE into liposomes would also have advantages. Early experiments in which ITE (1% of lipids by mass) was loaded into liposomes composed primarily (>50% by mass) of fully saturated lipids (e.g., 1,2-dimyristoyl-sn-glycero-3-phosphocholine; DMPC or 1,2-distearoyl-sn-glycero-3-phosphocholine; DSPC) yielded inconsistent ITE loading and frequent ITE precipitation. Egg phosphatidylcholine (egg PC) consists of a heterogeneous population of molecules having two fatty acids, one of which contains an unsaturated carbon-carbon double bond that effects its physicochemical properties. For this reason, liposomes containing egg PC have greater membrane fluidity and tend to be "leakier" than liposomes made with saturated fatty acid chains.

Liposomes were made by ethanol injection using three lipids: egg-PC, cholesterol, and PEG2000-DSPE in the molar ratio 30:15:2. A total of 92.61 mg of lipids in the indicated ratios were weighed (61.61 mg egg-PC, 15.47 mg cholesterol, and 14.96 mg PEG2000-DSPE) and added to a clean, 4 mL glass vial. Absolute ethanol (250 μL) was added to the lipids and the mixture stirred on a hot plate at 37-45° C. using a small magnetic stir bar for about five minutes. The mixture was removed from the hot plate and stirred for another 20-30 minutes. Once the lipids were dissolved, ITE was added in an amount equal to 1% of the total lipid weight (926 μg) by pipetting from a stock solution in DMSO (15.34 μL were added). Maximum DMSO volume did not exceed 8% of the starting ethanol volume (20 μL in this case). The lipid/ITE mixture was heated at 35-40° C. with intermittent agitation for 15 minutes or until ITE was dissolved. While waiting for ITE to dissolve, 2 mL of HEPES buffered saline solution (HBS, pH 6.5) was warmed to 35-40° C.

To co-formulate ITE and $MOG_{35-55}$ in liposomes, $MOG_{35-55}$ (amino acid sequence: MEVGWYRSPFSRVVH-LYRNGK (SEQ ID NO: 82)) was dissolved in HBS at concentrations of 0.05, 0.2, 0.5, and 1 mg/ml to make ITE/$MOG_{35-55}$ liposomes.

The lipid/ITE/ethanol solution was transferred into the warmed HBS (with or without $MOG_{35\_55}$) rapidly with a pre-warmed pasteur pipette while stirring. The mixture was stirred at 37-45° C. for 30 minutes. An extruder (Mini-Extruder, Avanti Polar Lipids) was used to reduce liposomes toward the desired size range of about 100 nm diameter. The liposome solution was passed sequentially through 400, 200, and 100 nm single polycarbonate (PC) membranes, 11 times each, in the warmed extruder (35-40° C.). The extruded liposomes were chilled by immersing in an ice-water bath. After 45 minutes, liposomes were chromatographically purified using a PD-10 column (Sephadex G25M, GE Healthcare), eluting in a final volume of 4 mL HBS. Liposomes were sterile-filtered through 0.2 μm PES filters and stored at 4° C. in HBS.

Liposomes were characterized for size, size distribution, and charge using the Malvern Zetasizer. Three batches of liposomes were prepared (B1, B2, B3), each including four types of liposomes: blank (plain) liposomes with no ITE or MOG35-55 (abbreviation: PL), ITE loaded liposomes (ITE-L), MOG35-55 loaded liposomes (MOG-L) and ITE plus MOG35-55 loaded liposomes (ITE-MOG-L). Size, size distribution, and charge of the liposomes in batches 1, 2, and 3 were quite similar, as shown in Table 5, below. Particle diameter ranged from 90-110 nm, with a small but consistent reduction in size in the ITE-MOG-L. Zeta potential was also moderately less negative in the liposomes loaded with MOG (−20 to −24 mV in the latter vs. −25 to −32 mV in the former).

TABLE 5

Physical characterization of ITE + $MOG_{35-55}$ liposomes

| Formulation Name | Diameter (nm) ± SD | PDI | Zeta potential (mv) ± SD |
|---|---|---|---|
| PL B1 | 105.7 ± 27.7 | 0.042 | −25.0 ± 8.2 |
| ITE-L B1 | 104.5 ± 28.7 | 0.052 | −31.7 ± 7.9 |
| MOG-L B1 | 105.8 ± 29.4 | 0.050 | −20.5 ± 7.4 |
| ITE-MOG-L B1 | 97.4 ± 28.1 | 0.064 | −21.4 ± 8.3 |
| PL B2 | 108.9 ± 29.1 | 0.045 | −27.0 ± 8.8 |
| ITE-L B2 | 108.6 ± 40.4 | 0.116 | −26.6 ± 9.2 |
| MOG-L B2 | 105.6 ± 27.5 | 0.041 | −23.8 ± 9.4 |
| ITE-MOG-L B2 | 88.5 ± 28.2 | 0.072 | −23.2 ± 9.5 |
| PL B3 | 105 ± 29.6 | 0.054 | −27.0 ± 9.0 |
| ITE-L B3 | 99.3 ± 29.0 | 0.050 | −27.0 ± 8.3 |
| MOG-L B3 | 106.5 ± 27.3 | 0.038 | −21.3 ± 8.2 |
| ITE-MOG-L B3 | 95.6 ± 29.0 | 0.064 | −22.0 ± 9.0 |

To measure loading of payload molecules (ITE, $MOG_{35-55}$), liposomes were dissolved in methanol:acetic acid (99:1 v/v) and ITE was quantitated spectrophotometrically as described in Example 1. $MOG_{35-55}$ concentration was measured using a microBCA kit (ThermoFisher Scientific, cat. number 23235) or a CBQCA Protein Quantitation Kit (ThermoFisher Scientific, cat. number C6667). As shown in Table 6, ITE encapsulation was consistent across batches (17-24% of starting ITE was encapsulated) and co-encapsulation of MOG35-55 did not interfere with ITE loading (average ITE encapsulation in ITE-L: 19.8%; average ITE encapsulation in ITE-MOG-L: 23.5%).

TABLE 6

ITE loading characterization of ITE + $MOG_{35-55}$ liposomes

| Formulation Name | Final [ITE] (μg/mL) | ITE (mg) per 4 ml | % of ITE encapsulated |
|---|---|---|---|
| ITE-L B1 | 45.2 | 0.181 | 19.7 |
| ITE-L B2 | 39.84 | 0.159 | 17.3 |
| ITE-L B3 | 51.18 | 0.205 | 22.3 |
| ITE-MOG-L B1 | 53.76 | 0.215 | 23.4 |
| ITE-MOG-L B2 | 55.67 | 0.223 | 24.2 |
| ITE-MOG-L B3 | 52.41 | 0.210 | 22.8 |

A stability assessment was performed in which liposomes from batch 1 were stored in HBS for one month at 4° C. and re-assayed. As shown in Tables 7 and 8, below, re-analysis of batch 1 liposomes after one month of storage revealed no significant changes in physical parameters.

TABLE 7

Characterization of batch 1 liposomes at time of storage

| Formulation Name | Diameter (nm) ± SD | PDI | Zeta potential (mv ± SD) | ITE loaded (μg/mL) | MOG loaded (μg/mL) |
|---|---|---|---|---|---|
| PL B1 | 105.7 ± 27.7 | 0.042 | −25 ± 8.2 | n/a | n/a |
| MOG-L B1 | 105.8 ± 29.4 | 0.050 | −20 ± 7.4 | n/a | n/a |
| ITE-L B1 | 104.5 ± 28.7 | 0.052 | −31.7 ± 7.9 | 45.2 | 180 |
| ITE-MOG-L B1 | 97.4 ± 28.1 | 0.064 | −21.4 ± 8.3 | 53.8 | 180 |

TABLE 8

Stability assessment of batch 1 liposomes after one-month storage

| Formulation Name | Diameter (nm) ± SD | PDI | Zeta potential (mv ± SD) |
|---|---|---|---|
| PL B1 | 105.2 ± 28.6 | 0.051 | −28.2 ± 8.0 |
| MOG-L B1 | 106.0 ± 27.6 | 0.036 | −19.7 ± 8.3 |
| ITE-L B1 | 103.0 ± 30.0 | 0.057 | −28.9 ± 7.7 |
| ITE-MOG-L B1 | 98.5 ± 27.0 | 0.047 | −25.1 ± 7.5 |

The effect of the starting concentration of ITE on encapsulation efficiency was assessed, and results are provided in Table 9, below.

TABLE 9

ITE encapsulation efficiency

| ITE added (% of lipid weight) | Number of batches | Initial ITE (mg) | ITE loaded (mg) | Average [ITE] in liposomes (μg/mL) ± SD | % ITE encapsulated |
|---|---|---|---|---|---|
| 1.0% | 4 | 0.92 | 0.18 ± 0.05 | 47.5 ± 9.3 | 20.6 ± 4.0 |
| 0.75% | 11 | 0.69 | 0.24 ± 0.05 | 58.8 ± 11.6 | 34.1 ± 6.7 |
| 0.5% | 4 | 0.46 | 0.25 ± 0.02 | 61.4 ± 4.4 | 53.4 ± 3.8 |

Conclusions

Previous attempts to directly encapsulate ITE in liposomes (e.g., using DSPC, DMPC, or HEPC and cholesterol) were unsuccessful because of low efficiency ITE encapsulation (2% or less), often accompanied by ITE precipitation, either during liposome formation or shortly afterwards. The characteristics of egg PC liposomes, however, permit direct formulation of ITE (and $MOG_{35-55}$). The amount of ITE loaded per 100 microliters (i.e., the typical dose volume for a mouse) is above the therapeutic threshold. Further, egg PC liposomes are stable over six months when refrigerated at 2-8° C.

Example 4.
1,2-dioleoyl-sn-glycero-3-phosphocholine (DOPC) Liposomes Loaded with ITE Liposomes made with a at least 50% egg PC have greater membrane fluidity than liposomes made with saturated phospholipids as a result of one unsaturated carbon-carbon double bond in egg PC. To determine if liposomes made using phospholipids having two unsaturated bonds would exhibit even greater fluidity and load ITE more efficiently, 1,2-dioleoyl-sn-glycero-3-phosphocholine (DOPC), which has a single unsaturated bond in each fatty acid chain, was used for liposomes. Liposomes were made by the ethanol injection method using three lipids: 1,2-dioleoyl-sn-glycero-3-phosphocholine (DOPC), cholesterol, and PEG2000-DSPE in the molar ratio 30:15:2) using the methods described in Example 3.

Two batches of DOPC liposomes were prepared with ITE added at 0.5% or 1.0% of the starting lipids (w/w). Two batches of egg PC liposomes were made in parallel to compare ITE loading. More ITE was encapsulated in DOPC liposomes than in egg PC liposomes at both ITE ratios, as shown in Table 10, below. At 0.75% ITE:lipids (w/w), encapsulation efficiency was 34.1% in egg-PC liposomes versus 51.8% in DOPC liposomes. At 0.5% ITE:lipids (w/w), encapsulation efficiency was 54.1% in egg-PC liposomes vs. 66.7% in DOPC liposomes. Thus, the positive influence of membrane fluidity on ITE loading extends beyond the presence of a phospholipid with one mono-unsaturated fatty acid (accounting for >50% of total lipids) to the presence of a phospholipid (accounting for >50% of total lipids) with two mono-unsaturated fatty acid chains.

TABLE 10

ITE loading comparison between DOPC and Egg PC

| Parameter | 0.5% ITE added (% of lipid weight) | | 0.75% ITE added (% of lipid weight) | |
|---|---|---|---|---|
| Main lipid used (+Chol + DSPE − PEG) | DOPC | Egg PC | DOPC | Egg PC |
| Initial amount of ITE (mg) | 0.47 | 0.46 | 0.70 | 0.69 |
| Final amount of ITE in liposomes (mg) | 0.313 | 0.25 | 0.363 | 0.236 |
| Final [ITE] in liposomes (μg/mL) | 78.3 | 62.2 | 90.6 | 58.8 |
| ITE encapsulated (% of initial amount) | 66.7 | 54.1 | 51.8 | 34.1 |
| Liposome production method | Rotary Evap. | Rotary Evap. | Rotary Evap. | Ethanol injection |

Subsequent experiments with egg PC as the unsaturated phospholipid show reproducible 60-65% ITE loading efficiency at 0.5% ITE by weight. Also, lipid concentrations of 60 or 65 mM (vs. 40 mM in earlier experiments) now allow production of larger liposome batches.

Example 5. Comparing the Effects of Saturated and Unsaturated Lipids on Encapsulation of ITE in Liposomes The aim of this study was to test various molar ratios within defined lipid concentration ranges and find combinations of egg PC, cholesterol and mPEG2000-PE that yield the best liposome characteristics for drug loading and long term stability. Further, to better understand the effect of using saturated vs. unsaturated lipids on ITE encapsulation, liposomes were prepared using the hydrogenated form of Egg PC (HEPC) (18:0), which differs from egg PC only by the absence of the unsaturated carbon-carbon bond in HEPC (i.e. HEPC has two saturated fatty acid chains vs. one monounsaturated fatty acid in egg PC).

Study Design:
   Lipid ratios were varied in the following range for each lipid:
   Egg PC or HEPC: ~53-72 mol %
   Cholesterol: ~25-44 mol %
   PEG2000-PE: 1.5 to 6.25 mol %
ITE was fixed at 0.5% by weight to the total lipid mass for all the batches tested. ITE was added from a DMSO stock. Batches were observed daily for any signs of precipitation/aggregation

TABLE 11

| Batch # | Lipid ratio (EPC:Chol: PEG2000-PE) | Mol percent in total lipid (EPC/Chol/ PEG2000-PE) | ITE amount (mg) added initially (0.5% w/w) |
|---|---|---|---|
| standard recipe | 3:1.5:0.2 | 63.83/31.91/4.26 | 1.122 mg |
| CL-1 | 3:2.5:0.2 | 52.63/43.86/3.51 | 1.247 mg |

TABLE 11-continued

| Batch # | Lipid ratio (EPC:Chol: PEG2000-PE) | Mol percent in total lipid (EPC/Chol/ PEG2000-PE) | ITE amount (mg) added initially (0.5% w/w) |
|---|---|---|---|
| CL-2 | 3:1.04:0.104 | 72.39/25.10/2.51 | 0.976 mg |
| CL-3 | 3:1.4:0.256 | 64.43/30.07/5.50 | 1.160 mg |
| CL-4 | 3:1.8:0.2 | 60.0/36.0/4.0 | 1.159 mg |
| CL-5 | 3:1.32:0.066 | 68.4/30.10/1.5 | 0.977 mg |
| CL-6 | 3:1.5:0.3 | 62.5/31.25/6.25 | 1.213 mg |
| CL-7 | 3:2:0.24 | 57.25/38.17/4.58 | 1.221 mg |
| CL-8 | 3:1.4:0.14 | 66.08/30.84/3.08 | 1.054 mg |

Methods

To eliminate any effect of additional lipids, HEPC liposomes were formulated using the same molar ratio as the standard recipe (see table) which uses egg PC (HEPC: Cholesterol:PEG2000PE (3:1.5:0.2)) using a lipid concentration of 40 mM. ITE was loaded at 0.5% w/w as for the routine batches that are made using egg PC. HEPC liposomes were made using the LIPEX extruder (3 mL, 40 mM). Following extrusion, polycarbonate membranes were checked for ITE precipitation during extrusion.

Observations

Although the extrusion proceeded smoothly, the majority of the ITE was found precipitated on the polycarbonate membrane. This result was consistent with our previous observations with DSPC and DMPC. In egg PC batches made in the same way there was no evidence of ITE precipitation, even when using lipid concentrations of 60 and 65 mM. Following extrusion, the HEPC liposomes were subjected to PD-10 purification step and finally filtered through 0.22 µm PES filters. In the final filtration step, ITE was found precipitated on the filter when using HEPC liposomes. Again, this did not occur with egg PC liposomes at 0.5% ITE (w/w). Finally, ITE loading in HEPC liposomes was measured. While egg PC batches routinely show around 60% ITE loading, the HEPC liposomes showed only 2.37% loading of ITE. Table 11 shows a summary of the observation.

TABLE 12

Effects of saturated and unsaturated lipids on ITE encapsulation in liposomes

| Lipid | Type | Observation |
|---|---|---|
| EPC (Egg PC) | Unsaturated | No precipitation of ITE on membrane; high loading of ITE in liposome |
| HEPC (Egg PC hydrogenated) | Saturated | High precipitation of ITE on membrane; low loading of ITE in liposome, not stable |
| DSPC | Saturated | High precipitation of ITE on membrane; low loading of ITE in liposome, not stable |
| DMPC | Saturated | High precipitation of ITE on membrane; low loading of ITE in liposome, not stable |

Effect of Cholesterol

The molar ratio of cholesterol influences ITE loading efficiency. The table below shows the cholesterol and egg PC concentrations (molar ratio, expressed as percent) of the nine liposome batches in Table 11.

TABLE 13

Batches ranked from highest to lowest mol % of each component

| Batch | Cholesterol mol % | Batch | EPC mol % | Batch | PEG mol % |
|---|---|---|---|---|---|
| CL-1 | 43.86 | CL-2 | 72.39 | CL-6 | 6.25 |
| CL-7 | 38.17 | CL-5 | 68.4 | CL-3 | 5.5 |
| CL-4 | 36.0 | CL-8 | 66.08 | CL-7 | 4.58 |
| standard recipe | 31.91 | CL-3 | 64.43 | standard recipe | 4.26 |
| CL-6 | 31.25 | standard recipe | 63.83 | CL-4 | 4.0 |
| CL-8 | 30.84 | CL-6 | 62.5 | CL-1 | 3.51 |
| CL-5 | 30.10 | CL-4 | 60.0 | CL-8 | 3.08 |
| CL-3 | 30.07 | CL-7 | 57.25 | CL-2 | 2.51 |
| CL-2 | 25.10 | CL-1 | 52.63 | CL-5 | 1.5 |

Results

TABLE 14

Characterization data of batches (Size, PDI, zeta potential and drug loading)

| Batch # | Mol percent in total lipid (eggPC/Chol/PE G2000-PE) | Size (nm ± SD) | PDI | Charge (mv ± SD) | Initial ITE amount | Final ITE amount (mg ± SD) | Percent Loading (% ± SD) | ITE conc (µg/ml ± SD) |
|---|---|---|---|---|---|---|---|---|
| standard formula | 63.83/31.91/4.26 | 101.6 ± 29.2 | 0.058 | −27.3 ± 9.4 | 1.122 mg | 0.69 ± 0.01 | 61.4 ± 0.6 | 114.8 ± 1.1 |
| CL-1* | 52.63/43.86/3.51 | 103.9 ± 25.5 | 0.031 | −27.3 ± 9.1 | 1.247 mg | 0.59 ± 0.02 | 46.8 ± 1.9 | 97.2 ± 4.0 |
| CL-2 | 72.39/25.10/2.51 | 103.3 ± 28.6 | 0.049 | −22.4 ± 9.0 | 0.976 mg | 0.61 ± 0.01 | 62.8 ± 1.2 | 102.2 ± 1.9 |
| CL-3 | 64.43/30.07/5.50 | 100.7 ± 25.7 | 0.037 | −27.9 ± 8.9 | 1.160 mg | 0.79 ± 0.01 | 67.9 ± 0.0 | 131.3 ± 0.1 |
| CL-4* | 60.0/36.0/4.0 | 101.5 ± 26.5 | 0.040 | −26.6 ± 9.0 | 1.159 mg | 0.70 ± 0.01 | 60.2 ± 0.9 | 116.3 ± 1.7 |
| CL-5 | 68.4/30.10/1.5 | 103.9 ± 27.3 | 0.037 | −18.9 ± 9.2 | 0.977 mg | 0.62 ± 0.01 | 63.4 ± 0.8 | 103.3 ± 1.2 |
| CL-6 | 62.5/31.25/6.25 | 102.2 ± 27.7 | 0.044 | −28.8 ± 9.4 | 1.213 mg | 0.75 ± 0.02 | 61.2 ± 1.8 | 123.9 ± 3.4 |
| CL-7* | 57.25/38.17/4.58 | 99.3 ± 25.9 | 0.044 | −28.9 ± 11 | 1.221 mg | 0.70 ± 0.02 | 57.1 ± 2.1 | 116.1 ± 4.3 |
| CL-8 | 66.08/30.84/3.08 | 102.3 ± 28.5 | 0.050 | −23.1 ± 9.7 | 1.054 mg | 0.64 ± 0.02 | 60.0 ± 2.0 | 105 ± 4.2 |

*Precipitation observed in 2 weeks (CL-1), 3 weeks (CL-7), and 1m (CL-4a) in liposomes stored at 4C.

Figure 1B:
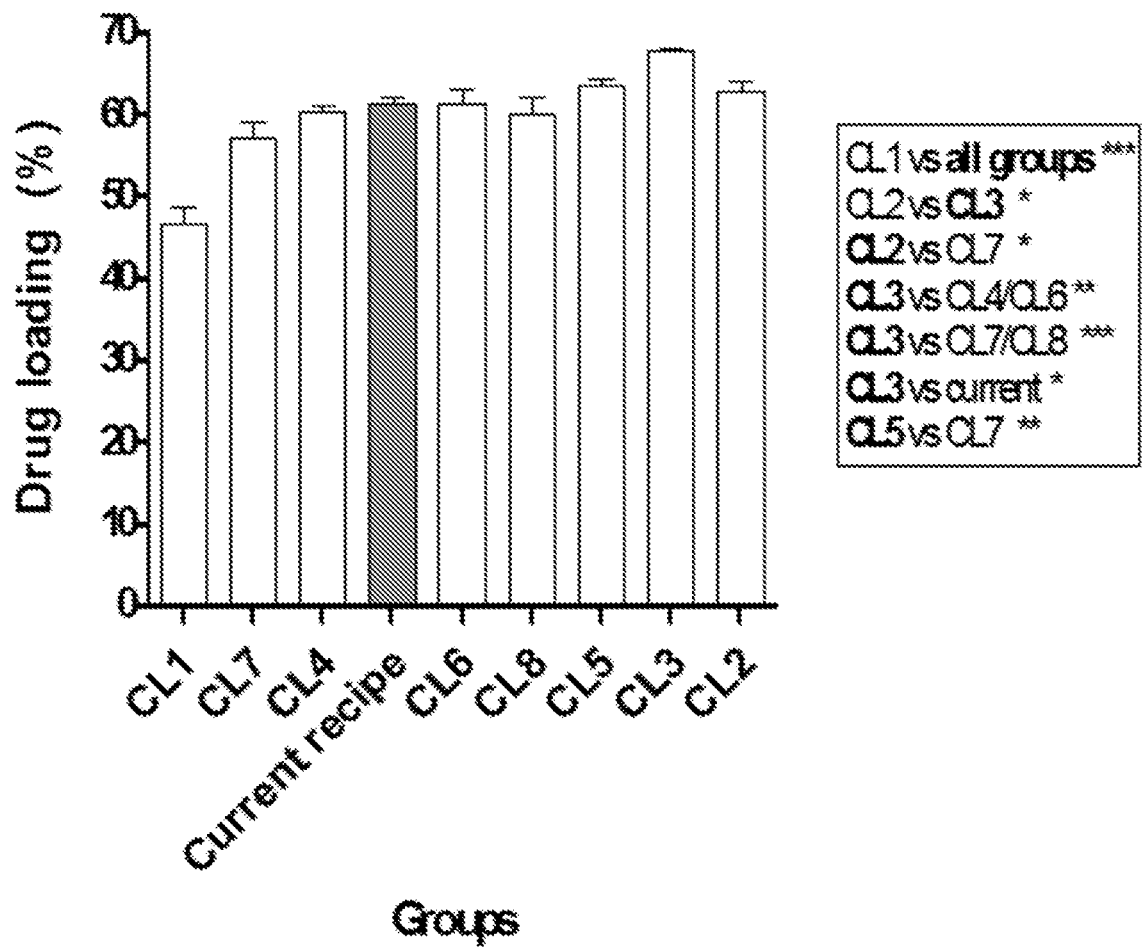
FIG. 1B is a chart showing the effect of varying cholesterol mole percentage and egg PC concentration on ITE loading (see Example 5).

As shown in Table 14 and FIG. 1B, drug loading is highest in the liposome batches with the cholesterol molar percent between 30%-32%, lowest in batch CL-1 with the highest cholesterol mole percent (43.86%), and second lowest in batch CL-7 with the second highest cholesterol mole percent (38.17%). ITE precipitated from both of these liposome batches within one week. The third batch in which ITE precipitated was CL-4, with 36% cholesterol molar ratio. Even though ITE loading was relatively efficient in this batch the high cholesterol limits liposome stability. The most efficient ITE loading was observed in batch CL-3, at 30.07% cholesterol, which was also stable for over 1 month (limit of observation).

Conclusions

As evident from the observation summarized in Table 11, saturated lipids are unfavorable to encapsulation of ITE in liposomes. If the ratios and relative amounts of other lipids in the formulation remain the same, a saturated lipid is preferable for efficient and stable ITE encapsulation.

In addition the cholesterol concentration affects ITE loading efficiency and statibility, with optimal results observed close to 30% cholesterol molar ratio.

Figure 3A:
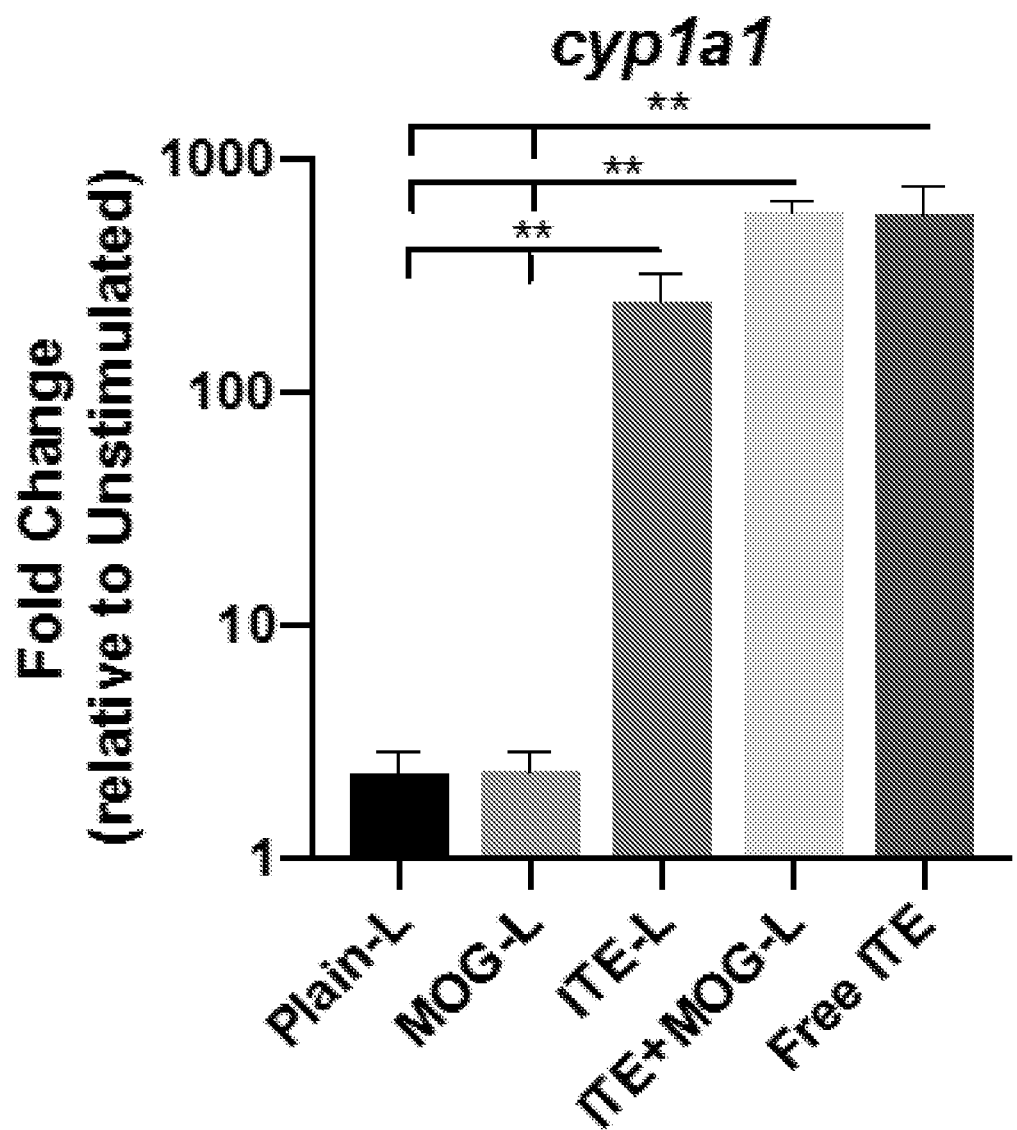
FIGS. 3A and 3B are a set of graphs showing Cyp1a1 mRNA expression (FIG. 4A) and Cyp1b1 mRNA expression (FIG. 4B) induced by ITE from egg PC liposomes or controls in dendritic cells isolated from mouse spleen. Liposomes without ITE were normalized in particle concentration to the ITE liposomes.
Figure 3B:
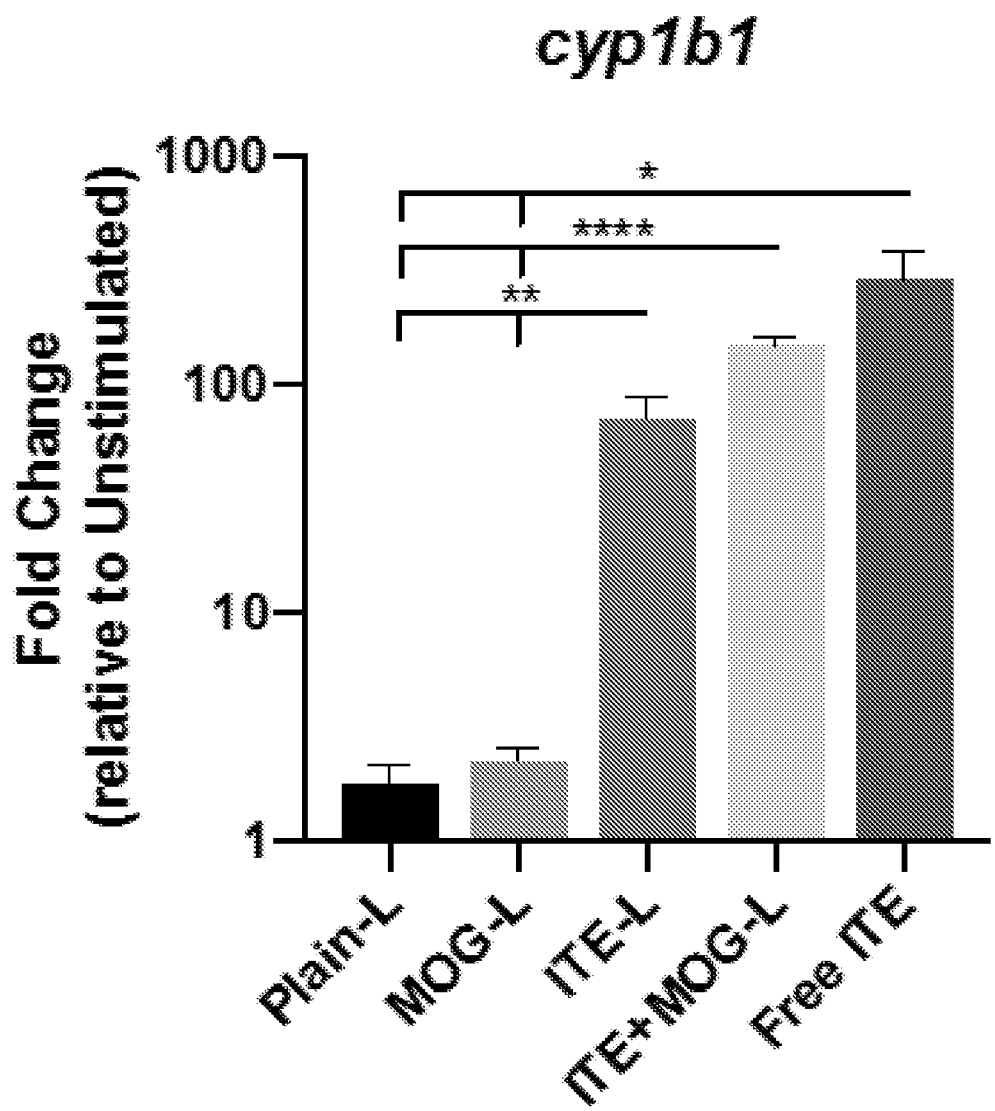

Example 6. Liposomes Loaded with ITE Induce Expression of Aryl Hydrocarbon Receptor (AHR)-Regulated Genes in Dendritic Cells In Vitro Dendritic cells (DCs) were isolated from the total spleen cell population of healthy C57Bl/6J mice using magnetic beads coated with an antibody against CD11c (Pan-DC isolation kit, Miltenyi Biotec). DCs were counted and plated in plastic tissue culture wells at 100,000-200,000 cells per well. Liposomes (blank or ITE loaded), or free ITE were added to the DCs at a concentration of 1 nM ITE and incubated for six hours at 37° C. DCs were then lysed, mRNA was isolated, and expression of Cyp1a1 and Cyp1b1, which are AHR-regulated genes, was measured by RT-PCR. Data show mean of 6 samples±SEM. Results of Egg PC ITE loaded liposomes are shown in FIG. 3.

Example 7. Liposomes Loaded with Peptides Induce T Cell Proliferation In Vitro

Figure 4:
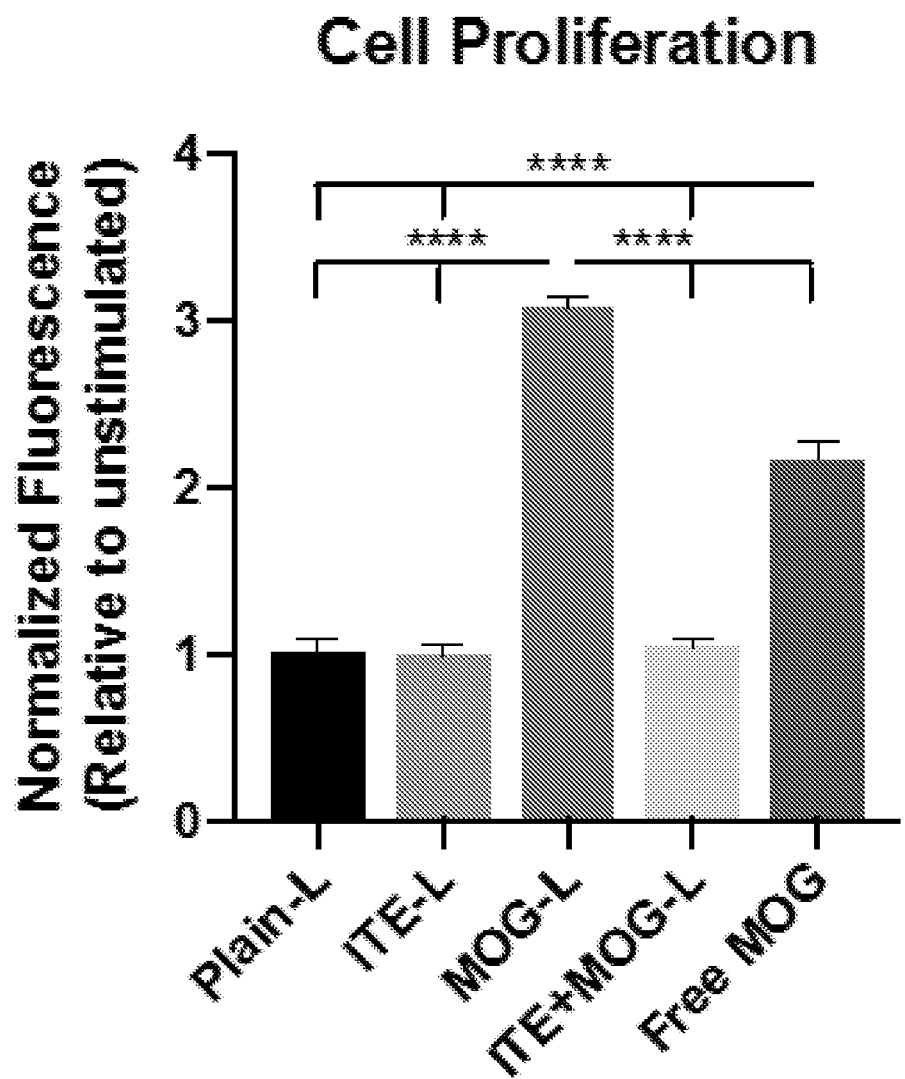
FIG. 4 is a graph showing proliferation of splenocytes of 2D2 mice after stimulation in vitro with MOG-loaded nanoparticles. Liposomes without MOG were normalized in particle concentration to their MOG-carrying counterparts.

Splenocytes were harvested from 2D2 mice, which express a transgenic 2D2 T cell repertoire (TCR) specific for $MOG_{35-55}$ and stimulated in vitro with 10 µg of MOG delivered either freely (Free MOG), loaded in egg-PC liposomes alone (MOG-L) or loaded in egg-PC liposomes and additionally stimulated with ITE-loaded egg-PC liposomes (at a dose of 1 µg ITE). Cell proliferation was assessed after incubation at 37° C. for 72 hours using a Cell Titer Blue cell proliferation assay. Data show mean of 4 samples±SEM. Results are shown in FIG. 4. Splenocytes stimulated with Free MOG or MOG-only liposomes induced 2D2 cell proliferation, indicating presentation of the MOG peptide to T cells. 2D2 splenocytes incubated with MOG liposomes and ITE liposomes did not induce T cell proliferation, indicating that ITE may be suppressing the proliferative T cell response.

Example 8. Treatment of Experimental Autoimmune Encephalomyelitis with Tolerogenic Liposomes Experimental autoimmune encephalomyelitis (EAE) is a mouse model of multiple sclerosis, which shares many pathogenic underpinnings with a broad range of autoimmune disorders. This Example illustrates the treatment of EAE with nanoparticulate liposomes of the present invention and, as discussed in the "Conclusions" section, reveals that the present invention provides unexpected potency against disease progression, as compared to known technologies, by generating immune tolerance characterized by suppression of CD4 T effector cells and induction of regulatory T cells (Tregs) and Tr1 cells.

Methods

Experimental autoimmune encephalomyelitis (EAE) was induced in C57BL/6 mice by subcutaneously injecting 200 µg $MOG_{35-55}$ in complete Freund's adjuvant (CFA). In addition, 200 ng of pertussis toxin (Sigma-Aldrich) was administered intraperitoneally (i.p.) on days 0 and 2.

Egg-PC liposomes (blank, ITE-loaded, or ITE+$MOG_{35-55}$-loaded), suspended in Hepes buffer, were administered intravenously (retro-orbitally) in 150 µL on day 7 to groups of 5 mice. ITE and ITE+MOG loaded liposomes were administered so that 7 µg of ITE was delivered per dose, and the ITE+MOG loaded liposomes contained 4 µg of $MOG_{35-55}$ peptide. Mice were monitored daily, beginning on day 10 and continuing through day 24, the final day of the experiment, for clinical signs of EAE. EAE was scored as follows: 0, no sign of disease; 1, loss of tone in the tail; 2, hind limb paresis; 3, hind limb paralysis; 4, tetraplegia; and 5, moribund. The average score and standard error of the mean were calculated for each group of 5 mice. At the conclusion of the experiment brain, lymph node and spleen were harvested from recently euthanized mice (all mice from each group were analyzed unless noted otherwise) and the following experiments were performed to assess the immunologic effects of the three different liposome formulations:
  (i) The spleens were dissociated into single cell suspensions and stimulated with $MOG_{35-55}$ peptide at concentrations of 1, 10, or 100 µg/mL to measure immunological recall. Cell proliferation was measured after 72 hours using an MTT cell proliferation assay.
  (ii) Brain and spinal cord were harvested and dissociated into single cell suspensions. CD4+ T cells were isolated using magnetic beads, permeabilized and fixed, stained with antibodies against interleukin 17 (IL-17) and interferon gamma (IFNγ), and analyzed by flow cytometry. Cells from 4-5 mice per group were analyzed.
  (iii) Brain and spinal cord-derived CD4+ T cells from (ii) above were stained with $MOG_{35-55}$-specific tetramers (multimerized MHCII proteins loaded with $MOG_{35-55}$) and with antibodies against FoxP3, CD25, Lag3 and CD49b, and analyzed by flow cytometry. Cells from 4-5 mice per group were analyzed.

Results

Figure 5:
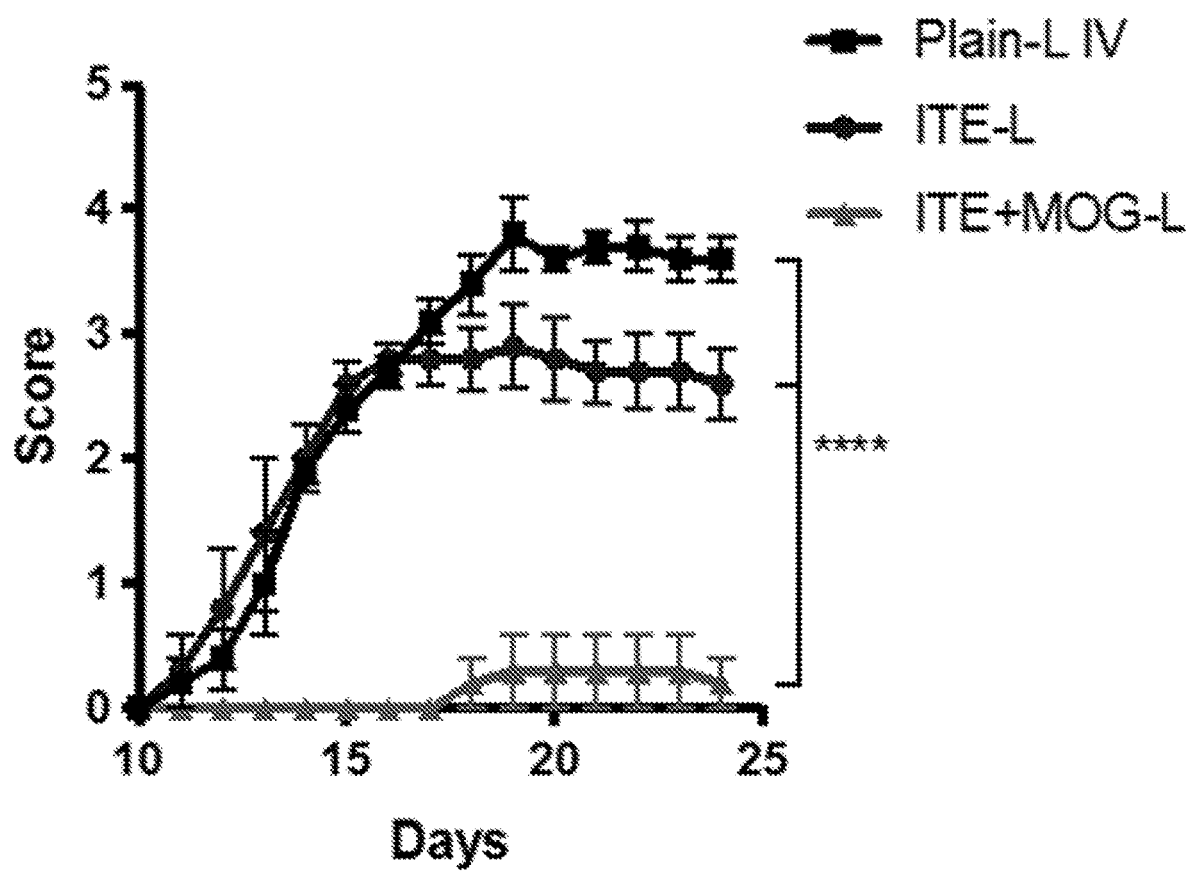
FIG. 5 is a graph showing progression of EAE in mice treated with empty (i.e., plain) egg PC liposomes (black circles); egg PC liposomes carrying ITE (blue squares); or egg PC liposomes carrying ITE and MOG (green triangles), as described in Example 6. Briefly, liposomes were suspended in Hepes buffer and administered intravenously (retro-orbitally) in 150 µL on day 7 to groups of 5 mice. ITE-loaded liposomes contained 7 µg of ITE per dose. MOG35-55-loaded liposomes contained 4 µg of peptide per dose. Mice were monitored daily, beginning on day 10 and continuing through day 24, the final day of the experiment, for clinical signs of EAE. EAE was scored as follows: 0, no sign of disease; 1, loss of tone in the tail; 2, hind limb paresis; 3, hind limb paralysis; 4, tetraplegia; and 5, moribund. The average score and standard error of the mean were calculated for each group of 5 mice.
Figure 6:
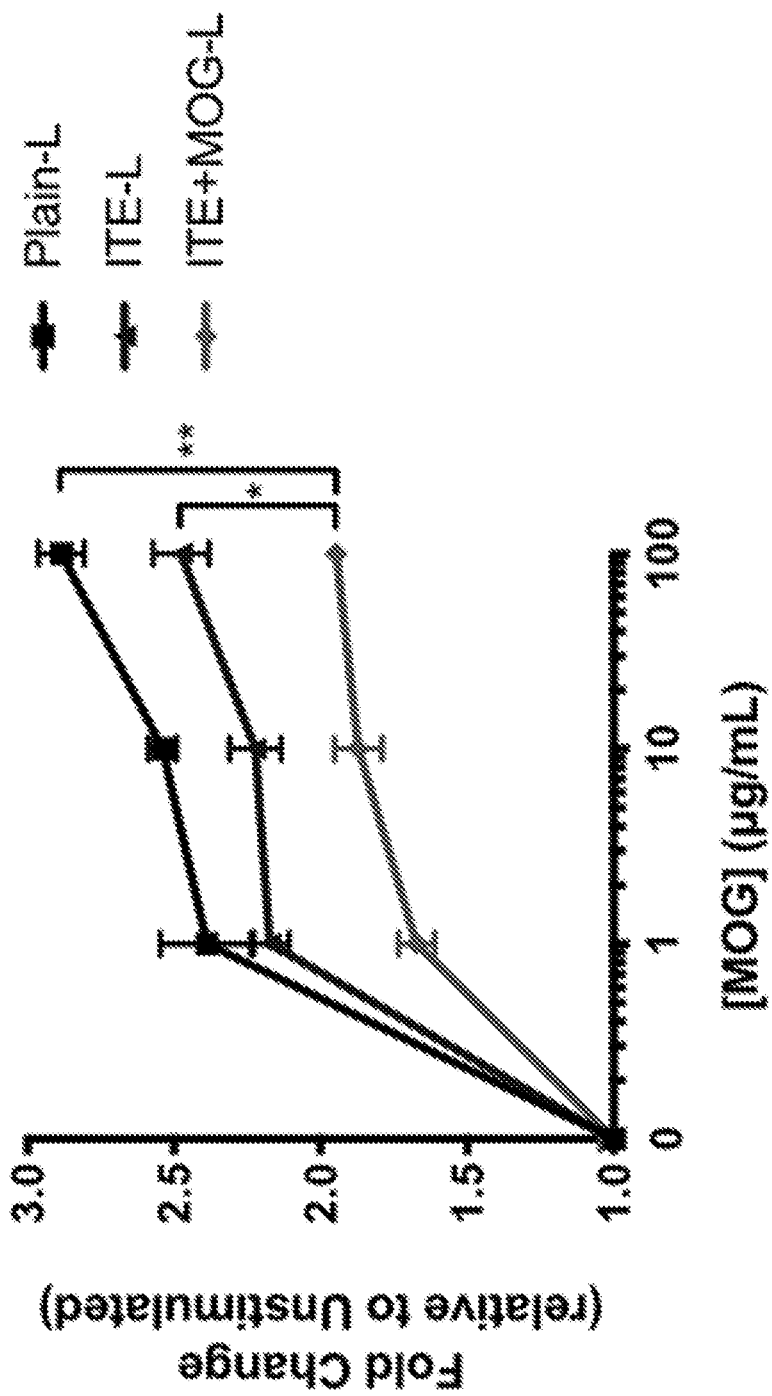
FIG. 6 shows proliferation of cells from spleen upon ex vivo re-stimulation with $MOG_{35-55}$ after in vivo treatment with empty egg PC liposomes (black circles), egg PC liposomes carrying ITE (blue squares); or egg PC liposomes carrying ITE and MOG (green triangles), as described above and in Example 6.

As shown in FIG. 5, treatment with ITE liposomes alone showed only a minor effect, while treatment with ITE+MOG liposomes significantly ameliorated symptoms of EAE, compared to mice treated with empty liposomes (Plain-L). To confirm tolerance of adaptive immune cells in the mice treated with ITE and $MOG_{35-55}$-loaded liposomes, lymphocytes from spleen and lymph nodes were harvested and re-stimulated ex vivo with $MOG_{35-55}$ peptide. As shown in FIG. 6, splenocytes harvested from mice treated with ITE and $MOG_{35-55}$-loaded liposomes proliferated less than lymphocytes from mice treated with control liposomes.

Figure 7A:
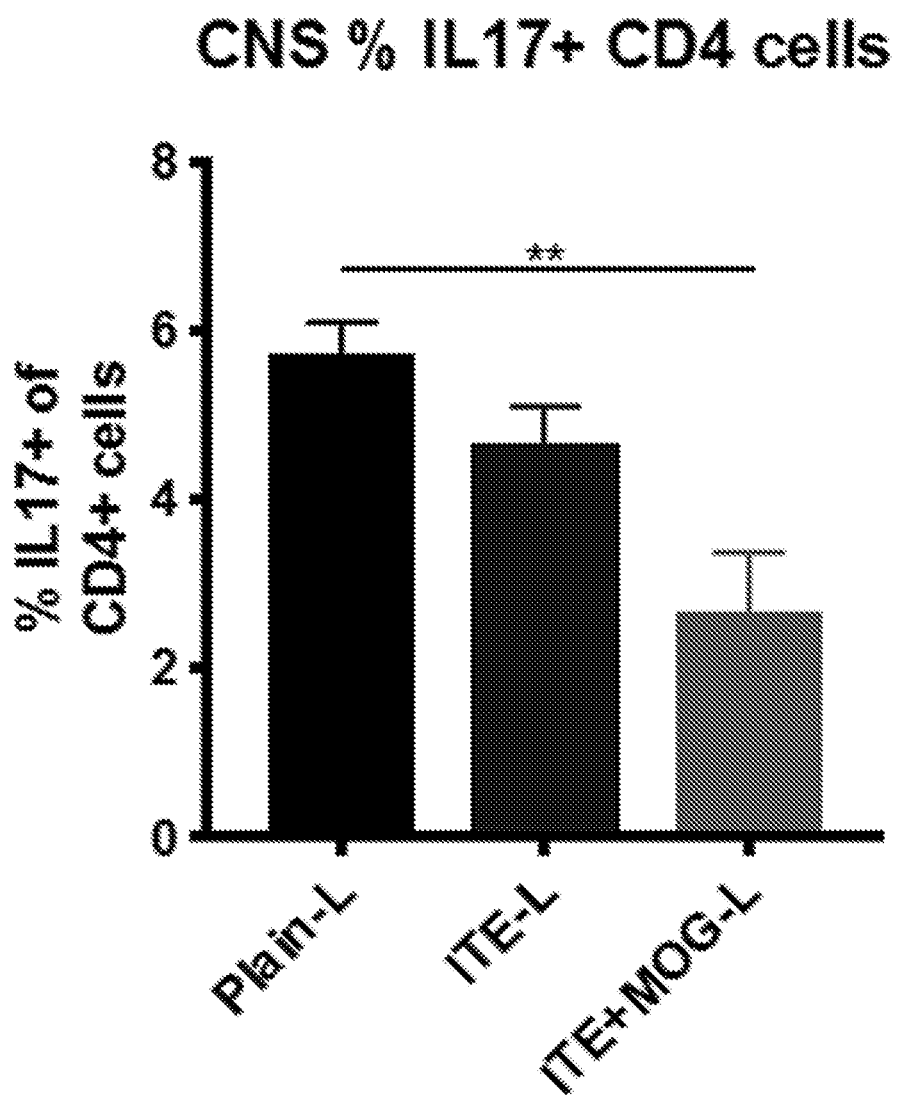
FIGS. 7A and 7B are a set of graphs showing the effect of treatment described in Example 6 on effector T cell infiltration into the CNS, as measured by percent of IL-17-positive T cells (FIG. 7A) and IFNγ-positive T cells (FIG. 7B).
Figure 7B:
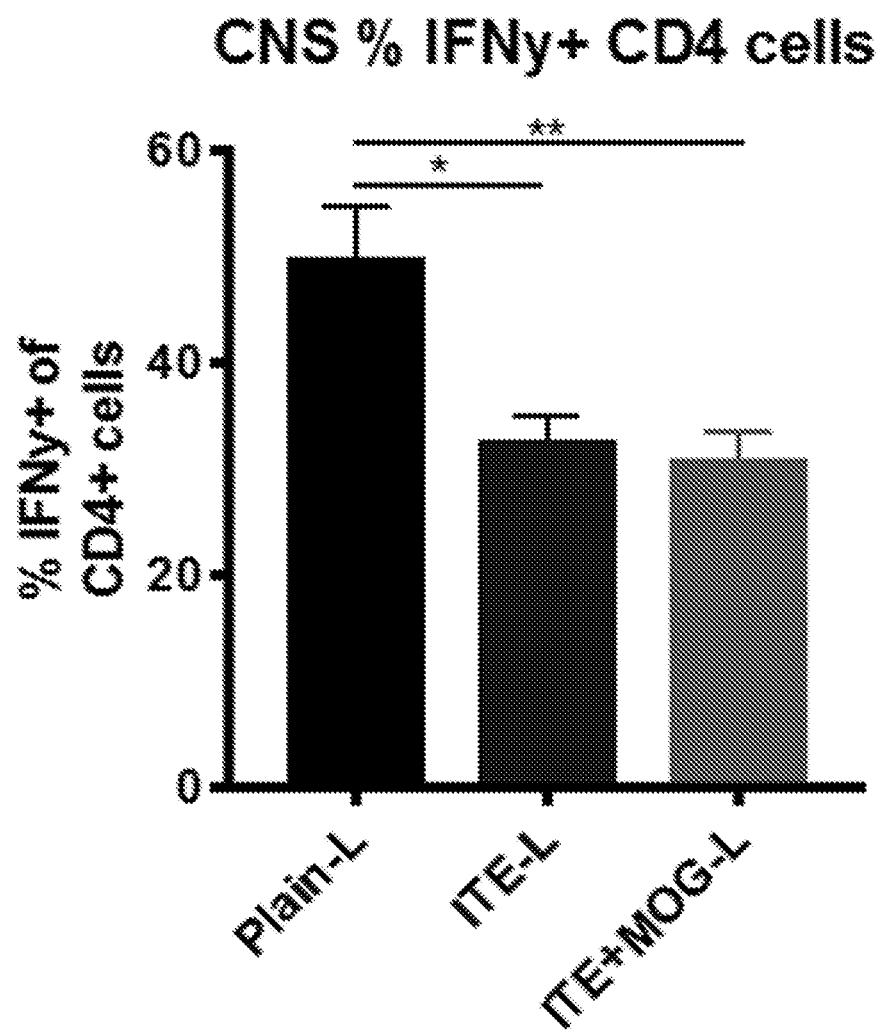
Figure 8A:
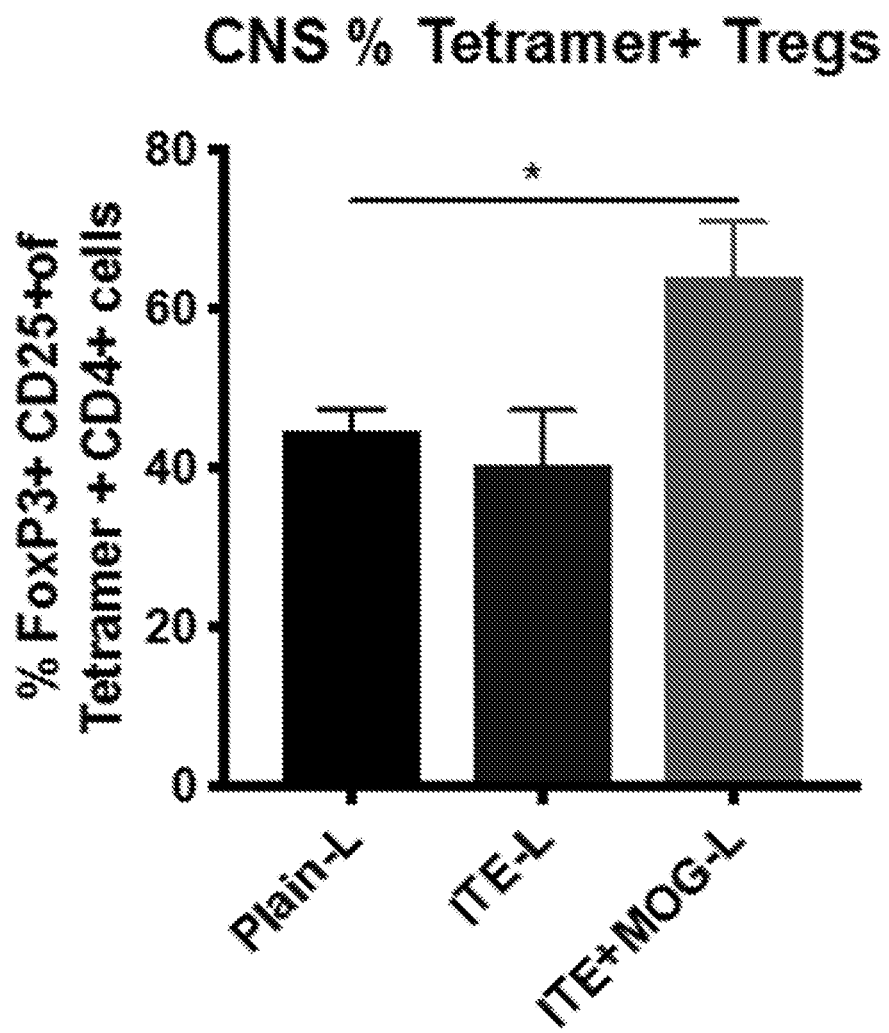
FIGS. 8A and 8B are a set of graphs showing an increase in antigen-specific Tregs (FIG. 10A) and Tr1 cells (FIG. 10B) in the CNS of mice treated as described in Example 6.
Figure 8B:
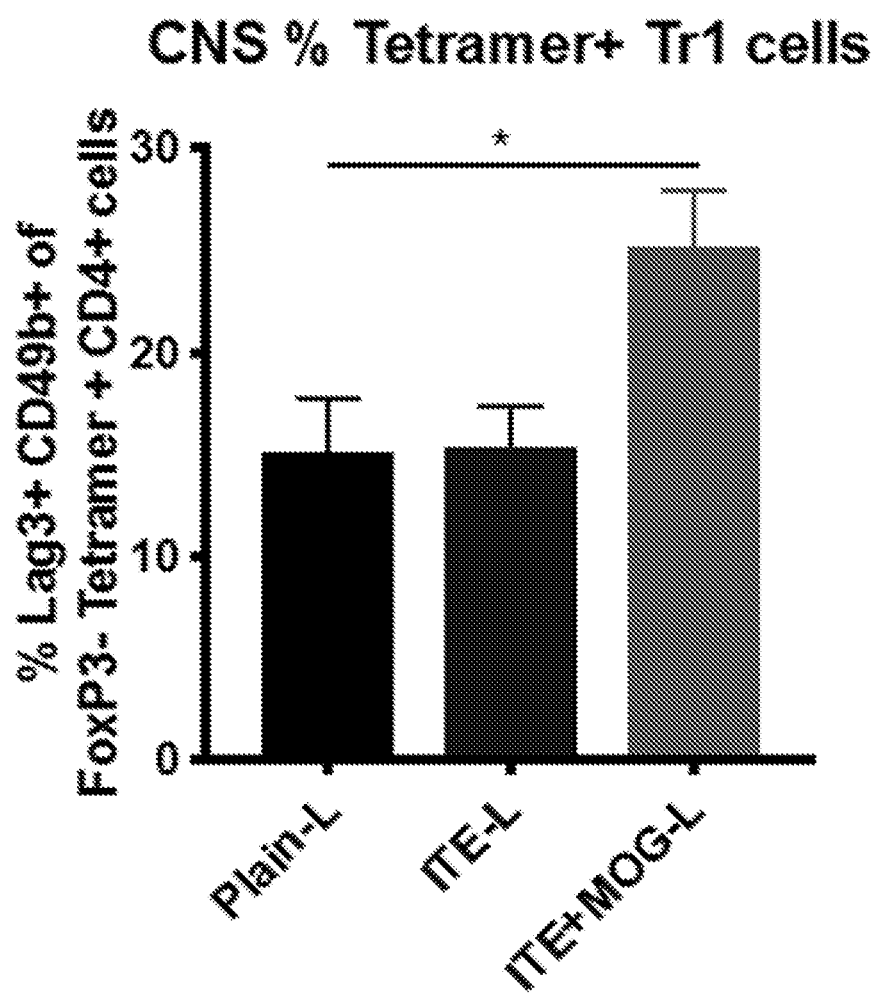

Phenotypes of lymphocytes from various tissues were assessed to elucidate whether ITE and $MOG_{35-55}$-loaded liposomes skewed the lymphocyte profile from an effector to a regulatory phenotype. Mice treated with ITE and $MOG_{35-55}$-loaded liposomes showed a significant reduction in the infiltration of effector $IL-17^+$ and $IFN\gamma^+$ T cells into the CNS, compared to empty liposome-treated mice and ITE-loaded liposome-treated mice (FIGS. 7A and 7B). Further, mice treated with ITE and $MOG_{35-55}$-loaded liposomes showed an expansion of antigen-specific $FoxP3^+$ regulatory T cells and $FoxP3^-$ Tr1 regulatory T cells in the brain and spinal cord.

Conclusions

Liposomes loaded with ITE and $MOG_{35-55}$ ameliorated symptoms of EAE in mice associated with suppression of effector T cell infiltration and expansion of T regulatory cells in the central nervous system. Encapsulation of ITE in liposomes was substantially more potent than the gold nanoparticles previously described. Yeste et al. (PNAS 2012) used ITE and $MOG_{35-55}$-loaded gold nanoparticles to treat EAE. Also, Quintana et al. (PNAS 2010) showed that EAE was ameliorated in the same mouse model by daily administration of 200 μg of ITE per mouse (i.p. or orally), a 28-fold higher dose than that presently used. Finally, Quintana et al. (Nature 2008) showed that 2,3,7,8-tetrachlorodibenzo-p-dioxin (TCDD), the most potent known AHR agonist, ameliorated EAE at a dose of 1 μg, but not at 100 ng. In most in vivo studies comparing ITE to TCDD, the latter is ~1,000-fold more potent. Therefore, the ~10 fold greater potency of liposomal ITE vs. unformulated TCDD is also surprising and highlights the potency of the present liposomal formulation.

Example 9. Prevention of Collagen-Induced Arthritis in Mice by Administration of Tolerogenic Nanoparticles Collagen-induced arthritis is an animal model of human rheumatoid arthritis, widely used because of its simplicity and reproducibility. Animals are immunized with type II collagen (CII) (normally expressed in joint cartilage; bovine CII was used in the experiments described below). This model recapitulates many of the innate and adaptive immune mechanisms that characterize human rheumatoid arthritis, and has been used to test treatments (like tumor necrosis factor antibodies) subsequently developed as human therapies.

Methods

The disease prevention model of arthritis was induced in C57/B16 mice in three steps. On day 0 mice were immunized with bovine CII (bCII) in complete Freund's adjuvant, administered subcutaneously (s.c.). A second s.c. immunization with bCII suspended in incomplete Freund's adjuvant followed on day 21, and on day 24 lipopolysaccharide (25 micrograms) was administered via intraperitoneal injection. The disease therapy model of arthritis was induced in C57/B16 mice in two steps. On day 0 mice were immunized with bovine CII (bCII) in complete Freund's adjuvant, administered subcutaneously (s.c.). A second s.c. immunization with bCII suspended in incomplete Freund's adjuvant followed on day 21.

Four groups of 8-10 mice (unless otherwise noted) were dosed twice per week via tail vein injection with plain liposomes, liposomes loaded with bCII only, liposomes loaded with ITE only, and liposomes loaded with ITE and bCII (group E). Naïve mice were not immunized with CII and received no treatment. Treatment was started on day −1 (disease prevention experiment) or on day 30-35, after 20% to 30% mice had developed arthritis (disease therapy experiment).

Mice were evaluated for the presence of disease (incidence per group) and cumulative disease score daily. Mice were weighed once per week for the first three weeks, and then starting on day 24 twice a week. Paw thickness was measured twice a week. The same measures were collected in both experiments.

In the disease prevention experiment mice were euthanized on day 46 and in the disease treatment experiment mice were euthanized on day 88. Blood, lymph nodes, spleen and joints were harvested for histolopathology and immunological analyses including titer of anti-CII antibodies in blood, level of FoxP3 expression in joints and number of Tr1 (T regulatory) cells detecting CII peptide (measured by combined staining for CII tetramer and Tr1 markers).

Statistically significant differences between groups (based on one-way ANOVA) are marked with asterisks. One asterisk indicates significance at the $P<0.05$ level. Two asterisks indicate significance at the $P<0.01$ level and three asterisks significance at the $P<0.001$ level.

Results

Figure 9B:
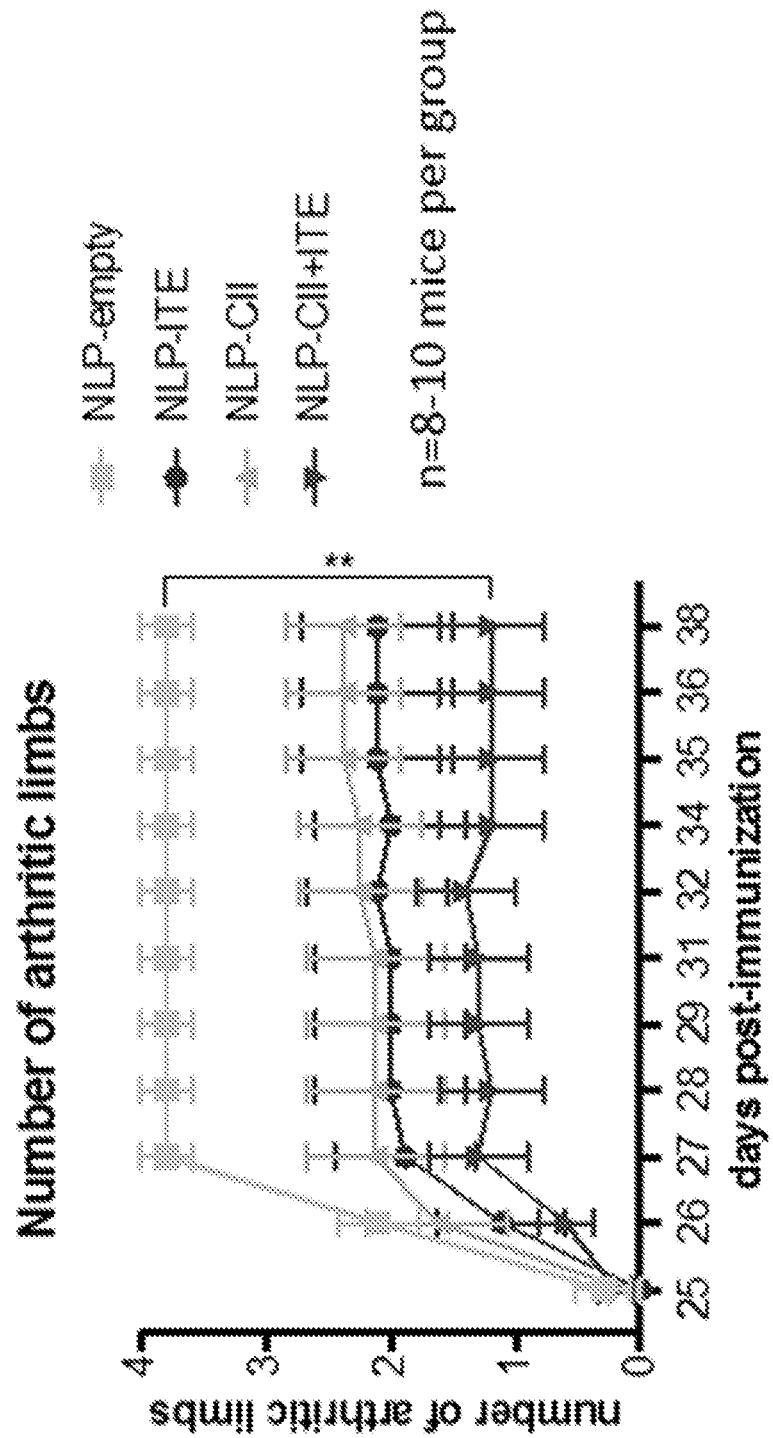
Figure 10A:
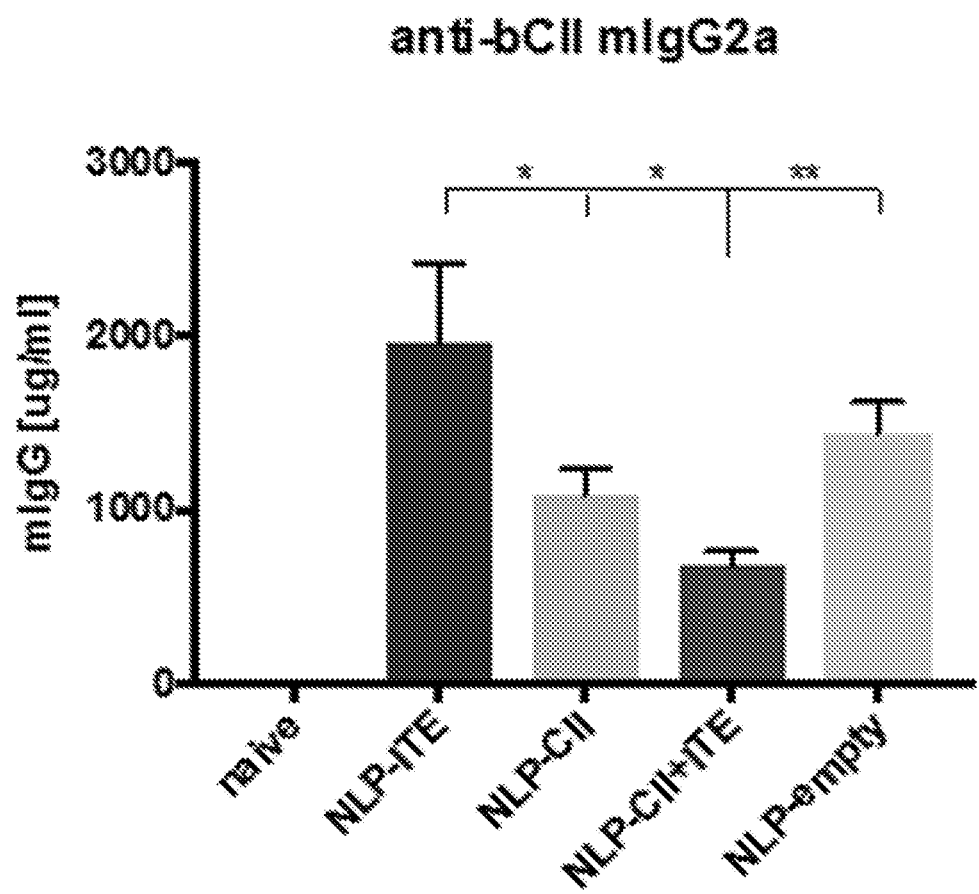
FIGS. 10A, 10B, 10C, and 10D are a set of graphs showing respectively the effects of the treatment with liposomes loaded with ITE+CII on anti-collagen type II IgG2a antibodies titers in the sera, the mRNA expression levels of FoxP3 and IL10 quantified by qPCR in the joints, and the frequencies of CII-reactive $CD4^+$ effector T cells in the spleen in mice treated on day −1 of disease initiation (disease prevention model).
Figure 10B:
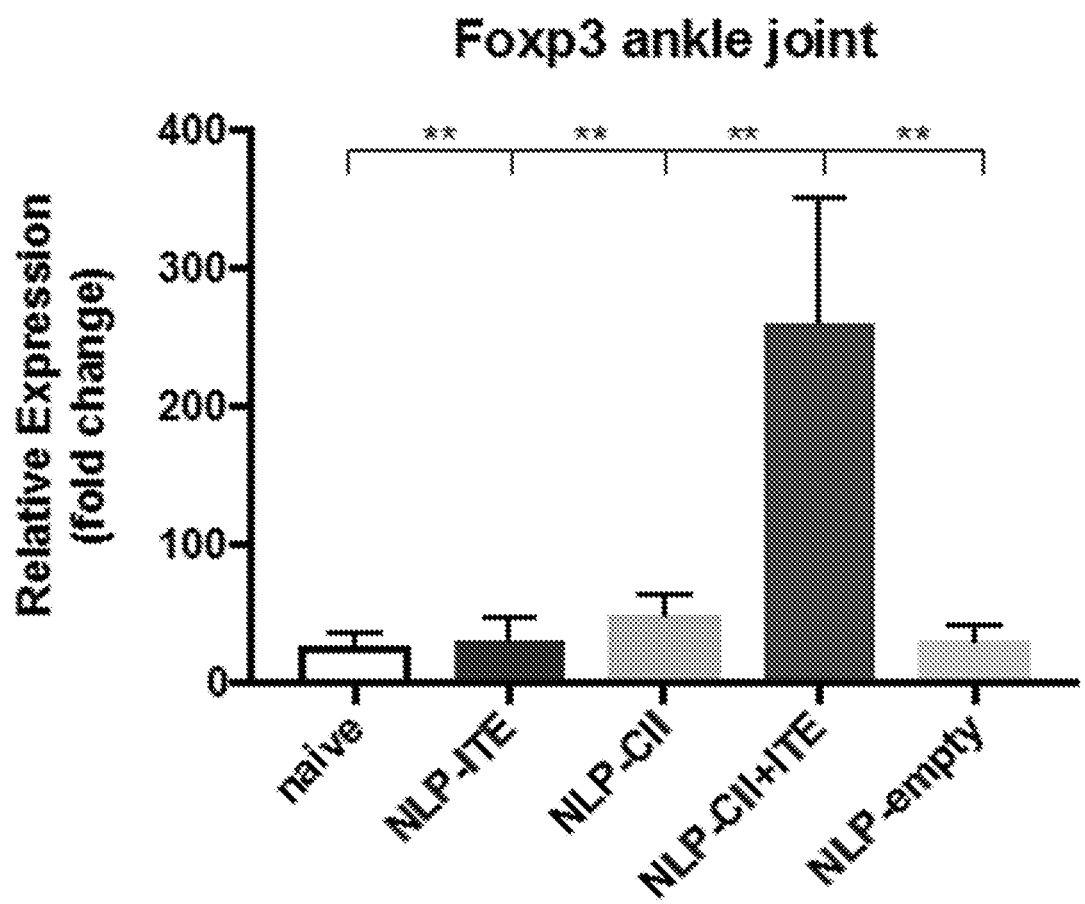
Figure 10C:
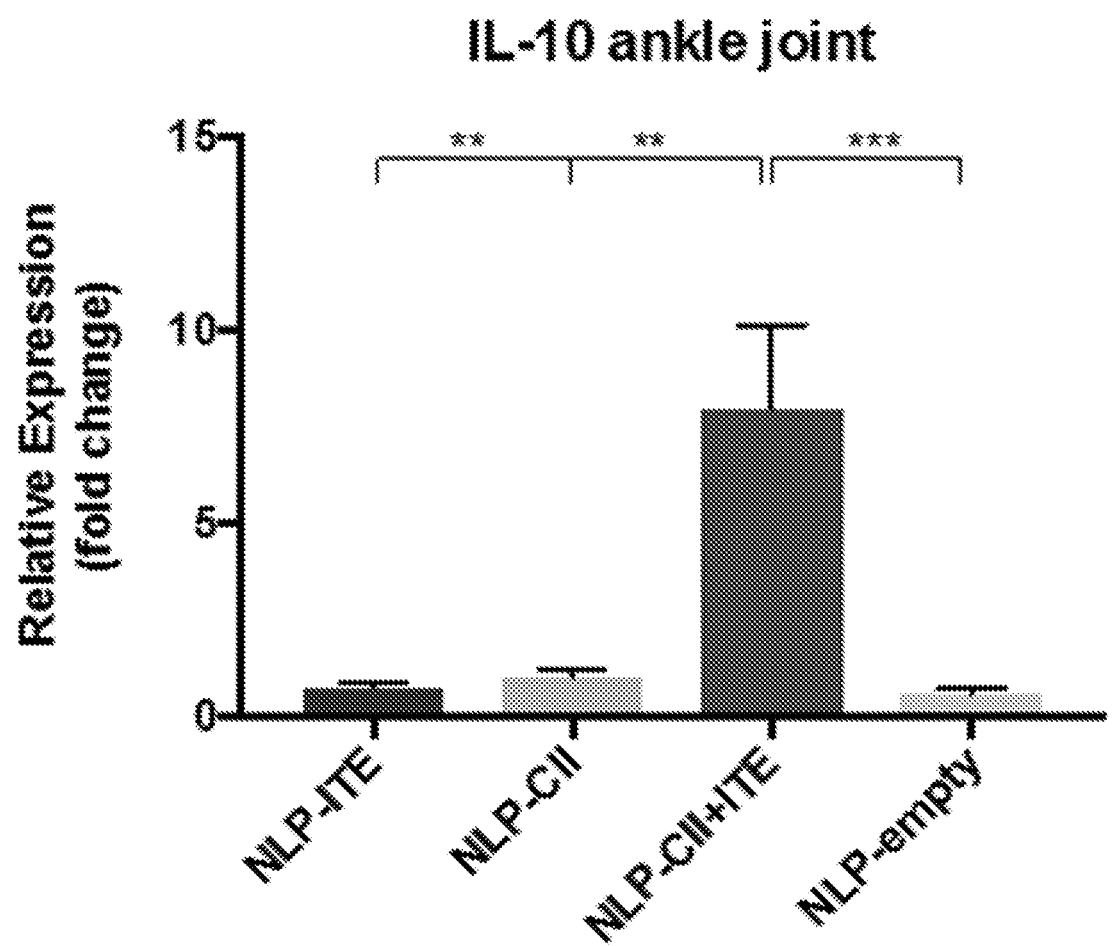
Figure 10D:
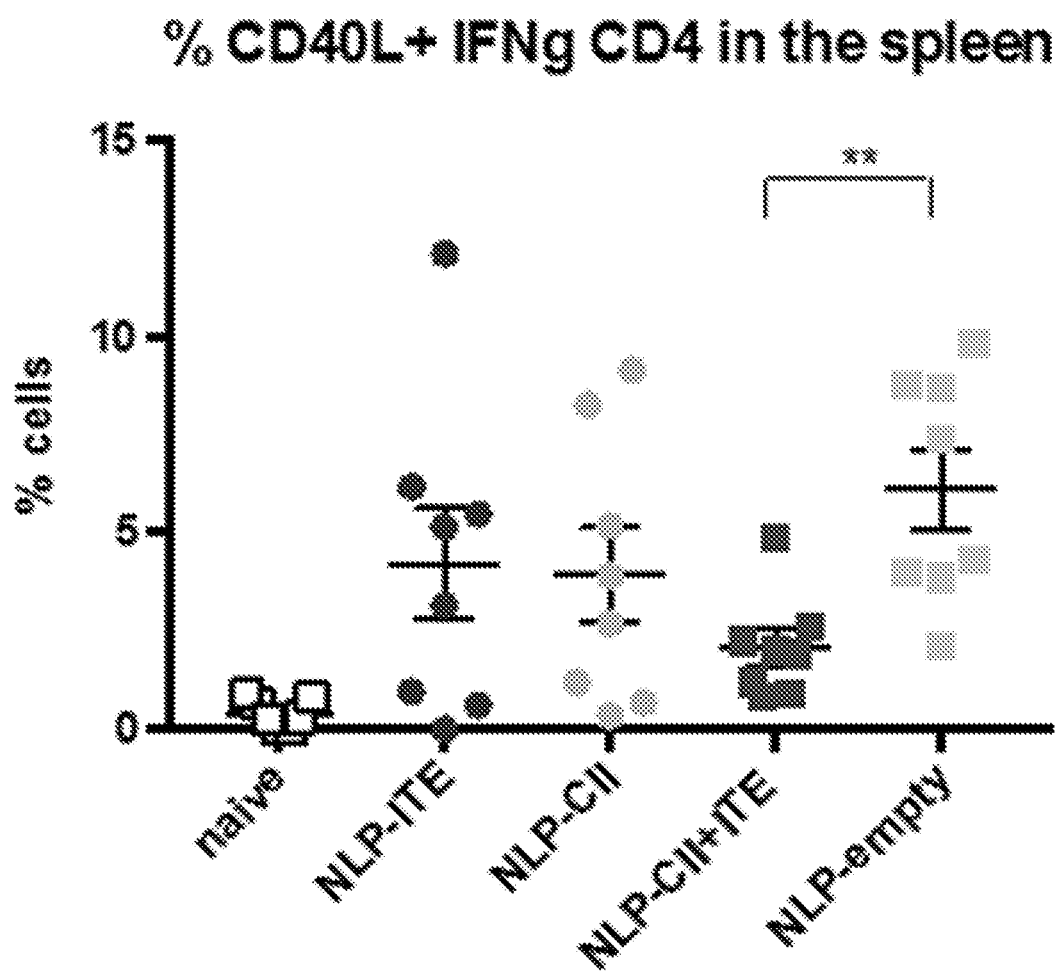

In the disease prevention model mice treated with liposomes loaded with ITE and CII experienced the least cumulative score and number of arthritic limbs (statistically significant at all measurement intervals) (FIGS. 9A and 9B). Mice treated with liposomes loaded with ITE and CII also showed lower titers of IgG2a antibodies than other treatment groups (FIG. 10A), and increased expression of FoxP3 and IL10 mRNA in the joints (FIGS. 10B and 10C). The frequencies of CII-responsive effector $CD4^+$ T cells was also reduced in the spleen of mice treated with liposomes loaded with ITE and CII as compared to empty liposomes (FIG. 10D).

Figure 11B:
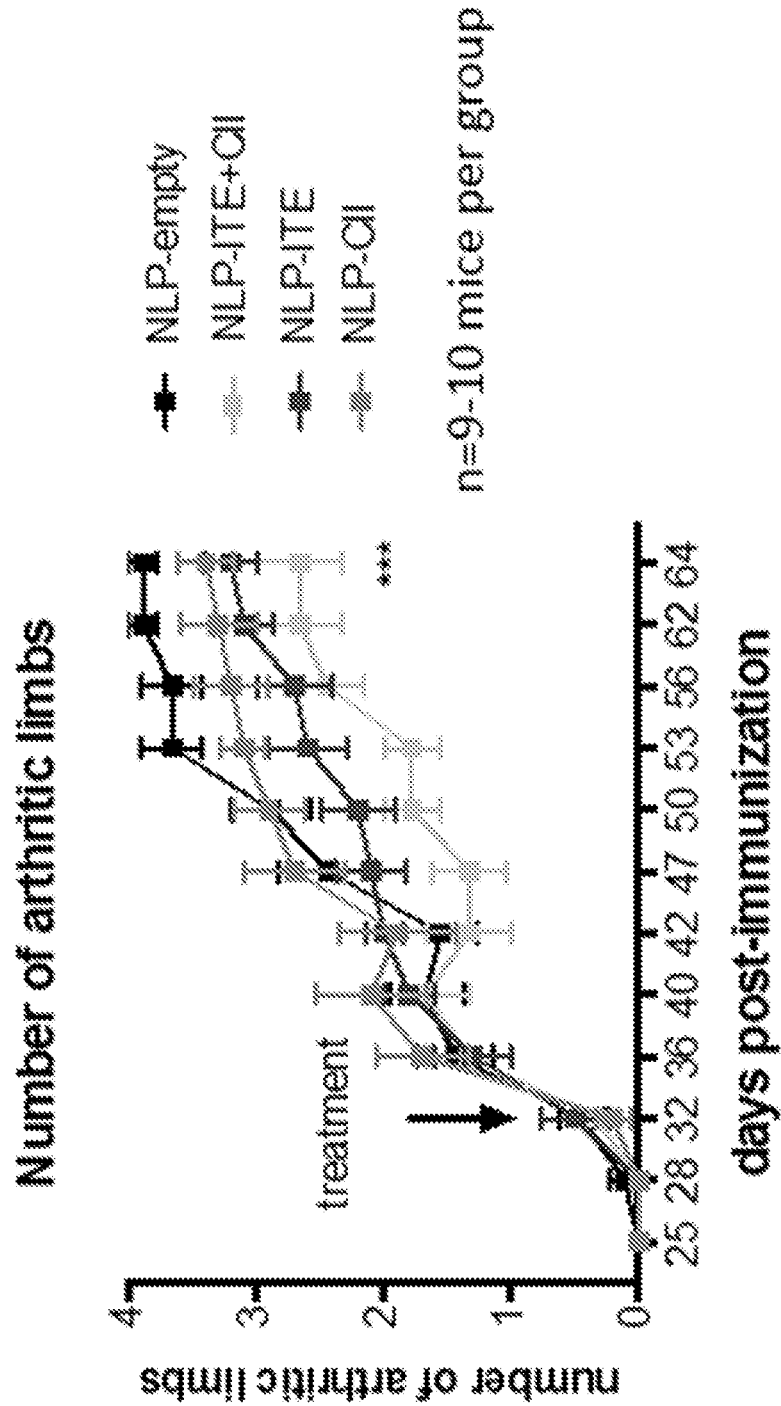
Figure 11C:
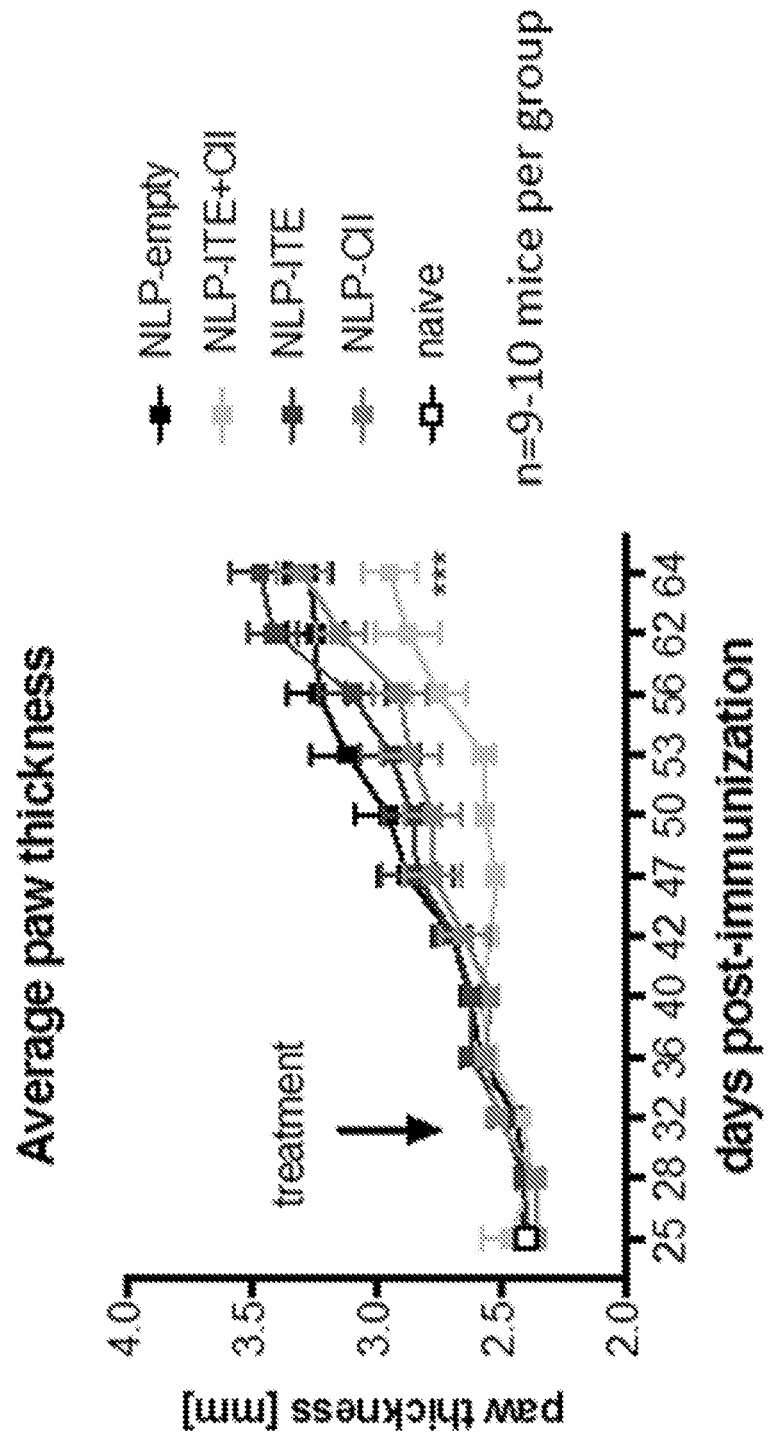
Figure 12A:
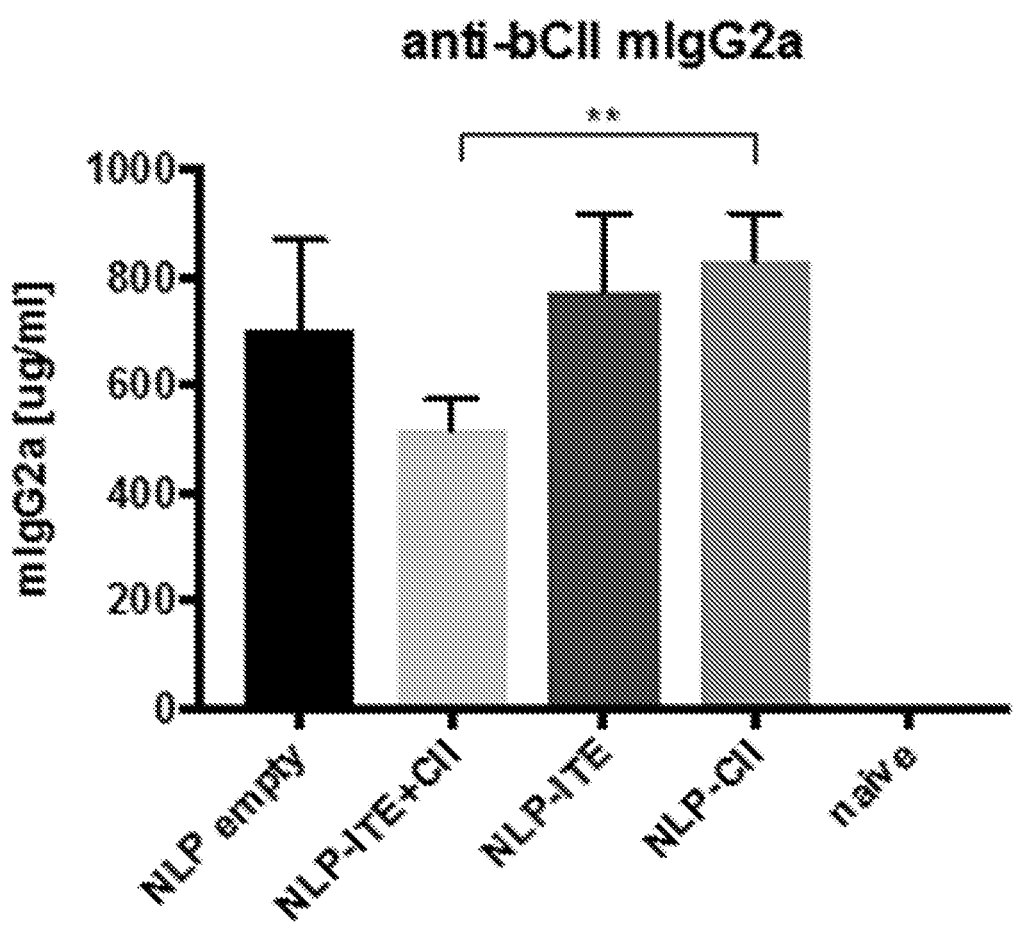
FIGS. 12A and 12B are a set of graphs showing the effects of the treatment with liposomes loaded with ITE+CII on anti-collagen type II IgG2a and IgG2b antibodies titers in the sera of mice treated from day 32 post disease initiation (disease therapy model).
Figure 12B:
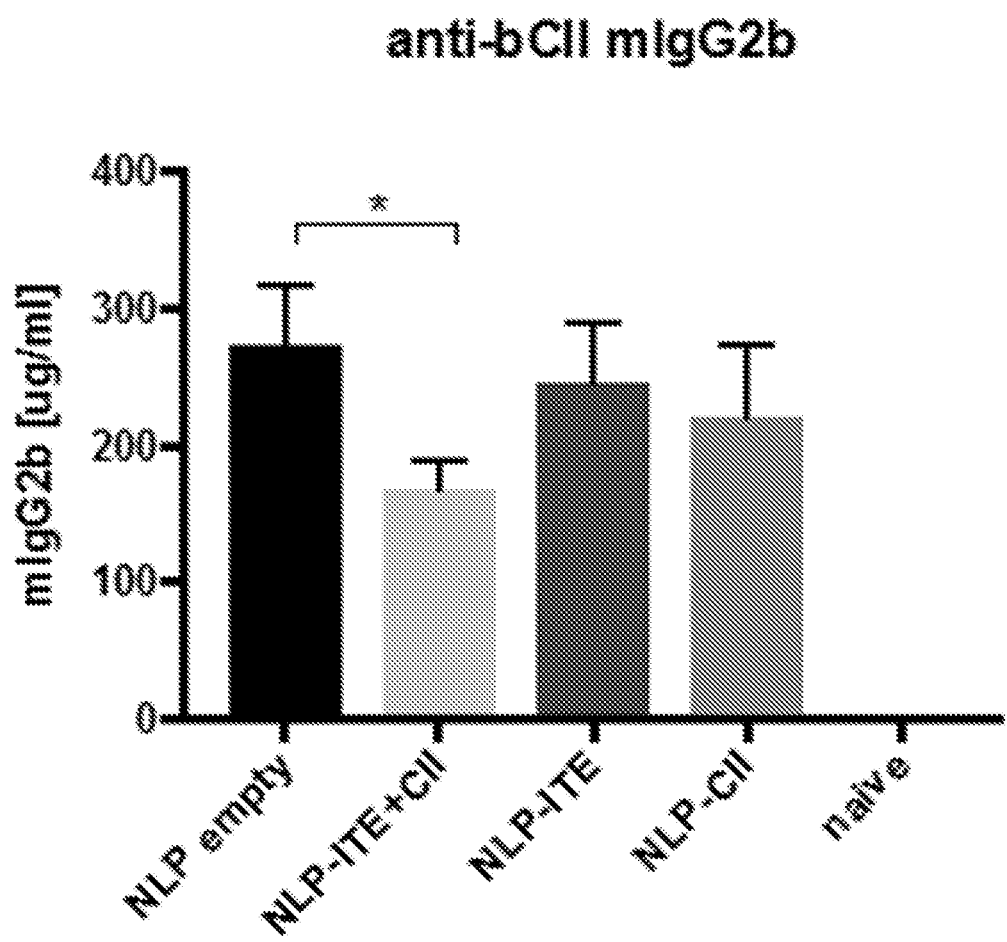

In the therapy model treatment began after 20-30% of the mice developed arthritis. As with the prevention model, treatment with liposomes loaded with ITE and CII ameliorate on-going collagen-induced arthritis. Specifically, mice treated with liposomes loaded with ITE and CII displayed a lower cumulative severity score (FIG. 11A), number of arthritic limbs (FIG. 11B) and average paw thickness (FIG. 11C). Mice treated with liposomes loaded with ITE and CII also showed lower titers of IgG2a and IgG2b antibodies than other treatment groups (FIGS. 12A and 12B).

Conclusions

Liposomes loaded with ITE and CII were effective in disease prevention and therapy models of collagen-induced arthritis. The mechanism of action involved stimulation of T regulatory cells, suppression of T effector cells and of autoantibody levels.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and can be applied to the essential features hereinbefore set forth, and follows in the scope of the claims.

Other embodiments are within the claims.

What is claimed is:

1. A composition comprising a population of liposomes having an average diameter from 50 to 250 nanometers (nm), wherein the population of liposomes comprises:
   (i) a lipid mixture comprising (a) at least 50% of egg phosphatidylcholine or 1,2-dioleoyl-sn-glycero-3-phosphocholine (DOPC); (b) between 26 mole percentage and 34 mole percentage cholesterol; and (c) a saturated poly(ethylene glycol) (PEG) derivatized lipid;
   (ii) an average from 200-15,000 molecules of 2-(1H-Indol-3-ylcarbonyl)-4-thiazolecarboxylic acid methyl ester (ITE), or salt thereof, per liposome.

2. The composition of claim 1, wherein the lipid mixture comprises egg phosphatidylcholine and cholesterol, wherein the egg phosphatidylcholine accounts for at least 50% of the lipid mixture and the cholesterol accounts for 30-32 mole percentage of the mixture.

3. The composition of claim 1 wherein the lipid mixture comprises 1,2-dioleoyl-sn-glycero-3-phosphocholine (DOPC) and cholesterol, wherein the DOPC accounts for at least 50% of the lipid mixture and the cholesterol accounts for 30-32 mole percentage of the mixture.

4. The composition of claim 1, wherein the saturated PEG derivatized lipid is PEG2000-DSPE.

5. The composition of claim 1, wherein the population of liposomes further comprises an antigen at a mass ratio of antigen-to-ITE from 1:10 to 100:1.

6. The composition of claim 5, wherein the antigen is a peptide antigen comprising an amino acid sequence selected from the group consisting of SEQ ID NOs: 1-81.

7. The composition of claim 5, wherein the antigen is associated with an autoimmune disorder.

8. The composition of claim 5, wherein the antigen comprises a therapeutic agent, wherein the therapeutic agent is:
   (i) a therapeutic protein or peptide;
   (ii) a virus or capsid protein or peptide; and/or
   (iii) a polynucleotide encoding (i) and/or (ii).

9. The composition of claim 1, wherein the population of liposomes has an average zeta potential from −10 to −50 mv.

* * * * *